United States Patent
Vega et al.

(10) Patent No.: US 7,647,184 B2
(45) Date of Patent: Jan. 12, 2010

(54) HIGH THROUGHPUT DIRECTED EVOLUTION BY RATIONAL MUTAGENESIS

(75) Inventors: Manuel Vega, Vigneux-sur-Seine (FR); Lila Drittanti, Vigneux-sur-Seine (FR)

(73) Assignee: Hanall Pharmaceuticals, Co. Ltd, Daejeon (KR)

(*) Notice: Subject to any disclaimer, the term of this patent is extended or adjusted under 35 U.S.C. 154(b) by 0 days.

(21) Appl. No.: 10/022,249

(22) Filed: Dec. 17, 2001

(65) Prior Publication Data

US 2003/0134351 A1 Jul. 17, 2003

Related U.S. Application Data

(60) Provisional application No. 60/315,382, filed on Aug. 27, 2001.

(51) Int. Cl.
*G01N 33/48* (2006.01)
(52) U.S. Cl. .......................................... 702/19
(58) Field of Classification Search .................. 702/19; 435/6, 5
See application file for complete search history.

(56) References Cited

U.S. PATENT DOCUMENTS

| | | | |
|---|---|---|---|
| 3,171,820 A | 3/1965 | Volz et al. ...................... | 521/61 |
| 4,797,368 A | 1/1989 | Carter et al. .................. | 435/320 |
| 5,096,815 A | 3/1992 | Ladner et al. | |
| 5,139,941 A | 8/1992 | Muzyczka et al. ........ | 435/172.3 |
| 5,223,409 A | 6/1993 | Ladner et al. .............. | 435/69.7 |
| 5,571,698 A | 11/1996 | Ladner et al. .............. | 435/69.7 |
| 5,723,323 A | 3/1998 | Kauffman et al. ......... | 435/172.3 |
| 5,753,500 A | 5/1998 | Shenk et al. ............... | 435/320.1 |
| 5,763,239 A | 6/1998 | Short et al. ............... | 435/172.1 |
| 5,770,434 A | 6/1998 | Huse ..................... | 435/252.33 |
| 5,779,434 A | 7/1998 | De Long .................... | 415/104 |
| 5,798,208 A | 8/1998 | Crea ............................ | 435/6 |
| 5,798,390 A | 8/1998 | Weber et al. ................ | 514/634 |
| 5,837,500 A | 11/1998 | Ladner et al. .............. | 435/69.7 |
| 5,862,514 A | 1/1999 | Huse et al. ................... | 702/22 |
| 5,871,974 A | 2/1999 | Huse ....................... | 435/69.7 |
| 5,925,565 A * | 7/1999 | Berlioz et al. .............. | 435/325 |
| 6,001,574 A | 12/1999 | Short et al. ................... | 435/6 |
| 6,013,478 A | 1/2000 | Wells et al. ................ | 435/69.1 |
| 6,057,103 A | 5/2000 | Short ............................ | 435/6 |
| 6,096,548 A | 8/2000 | Stemmer ................... | 435/440 |
| 6,117,679 A | 9/2000 | Stemmer ................... | 435/440 |
| 6,127,175 A | 10/2000 | Vigne et al. ................. | 435/325 |
| 6,132,970 A | 10/2000 | Stemmer ....................... | 435/6 |
| 6,156,509 A | 12/2000 | Schellenberger .............. | 435/6 |
| 6,165,793 A | 12/2000 | Stemmer ................... | 435/440 |
| 6,171,820 B1 | 1/2001 | Short ........................ | 435/69.1 |
| 6,174,673 B1 | 1/2001 | Short et al. .................... | 435/6 |
| 6,180,406 B1 | 1/2001 | Stemmer ................... | 435/440 |
| 6,238,884 B1 | 5/2001 | Short et al. ................ | 435/69.1 |
| 6,258,530 B1 | 7/2001 | Huse ............................. | 435/6 |
| 6,548,640 B1 | 4/2003 | Winter ..................... | 530/387.1 |
| 2002/0081574 A1 * | 6/2002 | Collett et al. ................... | 435/5 |
| 2003/0129203 A1 | 7/2003 | Vega et al. ................ | 424/233.1 |
| 2003/0129584 A1 | 7/2003 | Vega ............................. | 435/5 |
| 2003/0175694 A1 | 9/2003 | Vega et al. ..................... | 435/5 |
| 2003/0224404 A1 | 12/2003 | Vega et al. ..................... | 435/6 |
| 2004/0132977 A1 | 7/2004 | Gantier et al. .............. | 530/351 |
| 2005/0202438 A1 | 9/2005 | Gantier et al. | |
| 2006/0020116 A1 | 1/2006 | Gantier et al. | |
| 2006/0020396 A1 | 1/2006 | Gantier et al. | |
| 2006/0094655 A1 | 5/2006 | Guyon et al. | |
| 2006/0195268 A1 | 8/2006 | Vega ........................... | 702/19 |
| 2006/0247170 A1 | 11/2006 | Guyon et al. ................. | 514/12 |
| 2006/0251619 A1 | 11/2006 | Borrelly et al. ............ | 424/85.6 |
| 2007/0172459 A1 | 7/2007 | Gantier et al. ............. | 424/85.5 |
| 2007/0224665 A1 | 9/2007 | Gantier et al. ........... | 435/69.51 |
| 2007/0249532 A9 | 10/2007 | Guyon et al. ................. | 514/12 |
| 2007/0254838 A1 | 11/2007 | Gantier et al. ................ | 514/12 |

FOREIGN PATENT DOCUMENTS

| | | |
|---|---|---|
| EP | 0 240 224 | 10/1987 |
| EP | 1022335 | 7/2000 |
| FR | 2802645 | 12/1999 |
| WO | 95/23813 | 9/1995 |
| WO | 9738723 | 10/1997 |
| WO | 98/13487 | 4/1998 |
| WO | 9832880 | 7/1998 |
| WO | 99/07833 | 2/1999 |
| WO | 9911764 | 3/1999 |
| WO | 9964582 | 12/1999 |

(Continued)

OTHER PUBLICATIONS

Zlauddin et al. "Microarrays of Cells Expressing Defined cDNAs," Nature (May 2001) vol. 411, pp. 107-110.*

(Continued)

*Primary Examiner*—Jerry Lin
(74) *Attorney, Agent, or Firm*—K & L Gates LLP; Stephanie Seidman

(57) ABSTRACT

Processes and systems for the high throughput directed evolution of peptides and proteins, particularly those that act in complex biological settings, are provided. The proteins and peptides include, but are not limited to, intracellular proteins, messenger/signaling/hormone proteins and viral proteins. Also provided is a rational method for generating protein variants and also a method for titering viruses.

26 Claims, 12 Drawing Sheets

FOREIGN PATENT DOCUMENTS

| WO | 01/25253 | 4/2001 |
|---|---|---|
| WO | 01/25438 | 4/2001 |
| WO | 01/32711 | 5/2001 |
| WO | 01/32844 | 5/2001 |
| WO | 0144809 | 6/2001 |
| WO | 01/61344 | 8/2001 |
| WO | 0186291 | 11/2001 |
| WO | 0216606 | 2/2002 |
| WO | 03/018820 | 3/2003 |
| WO | 03/023032 | 3/2003 |
| WO | 2004/022593 | 3/2004 |
| WO | 2004/022747 | 3/2004 |
| WO | 2006/024547 | 3/2006 |

OTHER PUBLICATIONS

Giver et al. "Directed Evolution of a Thermostable Esterase," PNAS (1998) vol. 95, pp. 12809-12813.*

Persson et al. "Virus-Receptor Interaction in the Adenovirus System: Characterization of the Positive Cooperative Binding of Virions on HeLa Cells," Journal of Virology (1985) vol. 54, No. 1, pp. 92-97.*

Blazquez et al. "Single Amino Acid Replacements at Positions Altered in Naturally Occurring Extended-Spectrum TEM beta-Lactamases," Antimicrobioal, Agents, and Chemotherapy (Jan. 1995) vol. 39, No. 1, pp. 145-149.*

Ashktorab et al., "Identification of Nuclear Proteins That Specifically Interact with Adeno-Associated Virus Type 2 Inverted Terminal Repeat Hairpin DNA", *Journal of Virology*, 63:3034-3039 (1989).

ATCC accession No. VR-646, "Adeno-associated virus 4 deposited as Adeno-associated virus type 4", (accessed on Sep. 5, 2002).

ATCC accession No. VR-1449, "Simian virus 15", (accessed on Sep. 5, 2002).

ATCC accession No. VR-680, "Adeno-associated virus 2 deposited as Adeno-associated virus type 2", (accessed on Sep. 5, 2002).

ATCC accession No. VR-681, "Adeno-associated virus 3 deposited as Adeno-associated virus type 3", (accessed on Sep. 5, 2002).

ATCC accession No. VR-645, "Adeno-associated virus 1 deposited as Adeno-associated (satellite) virus type 1", (accessed on Sep. 5, 2002).

Atkinson et al., "A high-throughput hybridization method for titer determination of viruses and gene therapy vectors", *Nucleic Acids Research.*, 26:2821-2823 (1998).

Altschul et al., "Basic Local Alignment Search Tool", *J. Molec. Biol.*, 215:403-410 (1990).

Batchu et al., "Disassociation of Conventional DNA Binding and Endonuclease Activities by an Adeno-Associated Virus Rep78 Mutant", *Biochemical and Biophysical Research Communications*, 210:717-725 (1995).

Beaton et al., "Expression from the Adeno-Associated Virus p5 and p19 Promoters Is Negatively Regulated in *trans* by the *rep* Protein", *Journal of Virology*, 63:4450-4454 (1989).

Beck-Sickinger et al., "Complete L-alanine scan of neuropeptide Y reveals ligands binding to $Y_1$ and $Y_2$ receptors with distinguished conformations", *Eur. J. Biochem.*, 223:947-958 (1994).

Carrillo et al., "The Multiple Sequence Alignment Problem in Biology", *SIAM J. Applied Math*, 48:1073-1082 (1988).

Cassinotti et al., "Organization of the Adeno-Associated Virus (AAV) Capsid Gene: Mapping of a Minor Spliced mRNA Coding for Virus Capsid Protein 1", *Virology*, 167:176-184 (1988).

Chadeuf et al., "Efficient recombinant adeno-associated virus production by a stable rep-cap HeLa cell line correlates with adenovirus-induced amplification of the integrated rep-cap genome", *J. Gene Med.*, 2:260-268 (2000).

Chejanovsky et al., "Mutation of a Consensus Purine. Nucleotide Binding Site in the Adeno-Associated Virus *rep* Gene Generates a Dominant Negative Phenotype for DNA Replication", *J. Virology*, 64:1764-1770 (1990).

Chejanovsky et al., "Mutagenesis of an AUG Codon in the Adeno-Associated Virus *rep* Gene: Effects on Viral DNA Replication", *J. Virology*, 173:120-128 (1989).

Cullen et al., "Analysis of the Physical State of Different Human Papillomavirus DNAs in Intraepithelial and Invasive Cervical Neoplasm", *Journal of Virology*, 65:606-612 (1991).

Davis et al., "Mutational Analysis of Adeno-Associated Virus Type 2 Rep68 Protein Endonuclease Activity on Partially Single-Stranded Substrates", *Journal of Virology*, 74:2936-2942 (2000).

Davis et al., "Analysis of the Effects of Charge Cluster Mutations in Adeno-Associated Virus Rep68 Protein In Vitro", *Journal of Virology*, 73:2084-2093 (1999).

Deng et al., "Site-Directed Mutagenesis of Virtually Any Plasmid by Eliminating a Unique Site", *Analytical Biochemistry*, 200:81-88 (1992).

Derwent # 013914049, WPI Acc. No. 2001-398262/200142, for French Patent FR 2802645 and PCT Patent Application WO 2001/44809 "Evaluating the performance of complex biological agents in target cells, for selecting gene therapy vectors with optimal properties, comprises constructing a theoretical curve".

Derwent # 014262217, WPI Acc. No. 2002-082915/200211, for PCT Patent Application WO 2001/86291 A1, "Determining titer of biological agent, useful e.g. for gene therapy vectors or vaccines, is based on measuring reaction with cells at constant concentration, over a specified time period".

Devereux et al., "A comprehensive set of sequence analysis programs for the VAX", *Nucleic Acids Research*, 12(1):387-395 (1984).

Drittanti et al., "High throughput production, screening and analysis of adeno-associated viral vectors", *Gene Therapy*, 7:924-929 (2000).

Drittanti et al., "Optimised helper virus-free production of high-quality adeno-associated virus vectors", *The Journal of Gene Medicine*, 3:59-71 (2001).

Du et al., "Efficient transduction of human neurons with an adeno-associated virus vector", *Gene Therapy*, 3:254-261 (1996).

Gavin et al., "Charge-to-Alanine Mutagenesis of the Adeno-Associated Virus Type 2 Rep78/68 Proteins Yields Temperature-Sensitive and Magnesium-Dependent Variants", *Journal of Virology*, 73:9433-9445 (1999).

Genbank accession No. NC_002077, Nucleotide, "Adeno-associated virus 1, complete genome", (accessed on Sep. 5, 2002).

Genbank accession No. NC_001829, Nucleotide, "Adeno-associated virus 4, complete genome", (accessed on Sep. 5, 2002).

Genbank accession No. NC_001863, Nucleotide, "Adeno-associated virus 3B, complete genome", (accessed on Sep. 5, 2002).

Genbank accession No. NC_001401, Nucleotide, "Adeno-associated virus 2, complete genome", (accessed on Sep. 5, 2002).

Genbank accession No. NC_001729, Nucleotide, "Adeno-associated virus 3, complete genome", (accessed on Sep. 5, 2002).

Gibbs et al., "Rational Scanning Mutagenesis of a Protein Kinase Identifies Functional Regions Involved in Catalysis and Substrate Interactions", *Journal of Biology Chemistry*, 266:8923-8931 (1991).

Gribskov et al., "Sigma factors from *E. coli, B. subtilis*, phage SP01, and phage T4 are homologous proteins", *Nucleic Acids Research*, 14:6745-6763 (1986).

Hermonat, P.L., "Down-regulation of the human c-*fos* and c-*myc* proto-oncogene promoters by adeno-associated virus Rep78", *Cancer Letters*, 81:129-136 (1994).

Hermonat et al., "Genetics of Adeno-Associated Virus: Isolation and Preliminary Characterization of Adeno-Associated Virus Type 2 Mutants", *Journal of Virology*, 51:329-339 (1984).

Hill A.V., "The possible effects of the aggregation of the molecules of haemogloblin on its dissociation curves", *Proceedings of the Physiological, Journal of Physiology*, 40:iv-vii (1910).

Hill et al., "XLVII. The Combinations Of Haemoglobin With Oxygen And With Carbon Monoxide", *I. Biochem. J.*, 7:471-480 (1913).

Horer et al., "Mutational Analysis of Adeno-Associated Virus Rep Protein-Mediated Inhibition of Heterologous and Homologous Promoters", *Journal of Virology*, 69:5485-5496 (1995).

Im et al., "Partial Purification of Adeno-Associated Virus Rep78, Rep52, and Rep40 and Their Biochemical Characterization", *Journal of Virology*, 66:1119-1128 (1992).

Im et al., "The AAV Origin Binding Protein Rep68 Is an ATP-Dependent Site-Specific Endonuclease with DNA Helicase Activity", *Cell*, 61:447-457 (1990).

Kechli et al., "Expression of the Human Immunodeficiency Virus Type 1 Primer Binding Sequence Inhibits HIV-1 Replication", *Human Gene Therapy*, 9:587-590 (1998).

Kyostio et al., "Negative Regulation of the Adeno-Associated Virus (AAV) $P_5$ Promoter Involves both the $P_5$ Rep Binding Site and the Consensus ATP-Binding Motif of the AAV Rep68 Protein", *Journal of Virology*, 69:6787-6796 (1995).

Kyostio et al., "Identification of Mutant Adeno-Associated Virus Rep Proteins Which Are Dominant-Negative For DNA Helicase Activity", *Biochemical and Biophysical Research Communications*, 220:294-299 (1996).

Kyostio et al., "Analysis of Adeno-Associated Virus (AAV) Wild-Type and Mutant Rep Proteins for Their Abilities to Negatively Regulate AAV $p_5$ and $p_{19}$ mRNA Levels", *Journal of Virology*, 68:2957-2957 (1994).

Marcello et al., "Adeno-Associated Virus Type 2 Rep Protein Inhibits Human Papillomavirus Type 16 E2 Recruitment of the Transcriptional Coactivator p300", *Journal of Virology*, 74:9090-9098 (2000).

Matsushita et al., "Localization of von Willebrand Factor-binding Sites for Platelet Glycoprotein lb and Botrocetin by Charged-to-Alanine Scanning Mutagenesis", *Journal of Biology Chemistry*, 275:11044-11049 (2000).

McCarty et al., "Analysis of Mutations in Adeno-Associated Virus Rep Protein In Vivo and In Vitro", *Journal of Virology*, 66:4050-4057 (1992).

Mendelson et al., "Identification of the *trans*-Acting Rep Proteins of Adeno-Associated Virus by Antibodies to a Synthetic Oligopeptide", *Journal of Virology*, 60:823-832 (1986).

Mittereder et al., "Evaluation of the Concentration and Bioactivity of Adenovirus Vectors for Gene Therapy", *Journal of Virology*, 70:7498-7509 (1996).

Needleman et al., "A General Method Applicable to the Search for Similarities in the Amino Acid Sequence of Two Proteins", *Journal of Molec. Biol.*, 48:443 (1970).

Nelson et al., "Characterization of Diverse Viral Vector Preparations, Using a Sample and Rapid Whole-Virion Dot-Blot Method", *Hum. Gene Ther.*, 9:2401-2405 (1998).

Ni et al., "In Vitro Replication of Adeno-Associated Virus DNA", *Journal of Virology*, 68:1128-1138 (1994).

Owens et al., "Identification of a DNA-Binding Domain in the Amino Terminus of Adeno-Associated Virus Rep Proteins," *J. Virology*, 67(2):997-1005 (1993).

Owens et al., "In Vitro Resolution of Adeno-Associated Virus DNA Hairpin Termini by Wild-Type Rep Protein Is Inhibited by a Dominant-Negative Mutant of Rep", *Journal of Virology*, 66:1236-1240 (1992).

Owens et al, "Adeno-Associated Virus Rep Proteins Produced in Insect and Mammalian Expression Systems: Wild-Type and Dominant-Negative Mutant Proteins Bind to the Viral Replication Origin", *Journal of Virology*, 184:14-22 (1991).

Pearson et al., "Improved tools for biological sequence comparison", *Proc. Natl. Acad. Sci. USA*, 85:2444 (1988).

Press Release 11; "Nautilus Biotech granted patent covering molecular fitness analysis with key applications in directed evolution and functional genomics target identification"; Paris- Feb. 6, 2002; http://www.nautilusbiotech.com/news-pressrelease11.php3, accessed on (Feb. 28, 2002).

Press Release 10; "Nautilus Biotech and Microbix Biosystems, Inc. (TSE: MBX) sign a distribution agreement for rAAV high-producer cells"; Paris- Jan. 11, 2002; http://www.nautilusbiotech.com/news-pressrelease10.php3, accessed on (Feb. 28, 2002).

Press Release 7; "Nautilus Biotech optimizes the AAV rep protein to increase rAAV productivity"; Paris- Sep. 21, 2001; http://www.nautilusbiotech.com/news-pressrelease7.php3, accessed on (Feb. 28, 2002).

Press Release 6; "Nautilus Biotech S.A. Files a Key Patent Application in the U.S."; Paris- Sep. 14, 2001; http://www.nautilusbiotech.com/news-pressrelease6.php3, accessed on (Feb. 28, 2002).

Ropp et al., "*Aequorea* Green Fluorescent Protein Analysis by Flow Cytometry", *Cytometry*, 21:309-317 (1995).

Ruffing et al., "Mutations in the carboxy terminus of adeno-associated virus 2 capsid proteins affect viral infectivity: lack of an RGD integrin-binding motif", *J. Gen. Virol.*, 75:3385-3392 (1994).

Ryan et al., "Sequence Requirements for Binding of Rep68 to the Adeno-Associated Virus Terminal Repeats", *Journal of Virology*, 70:1542-1553 (1996).

Salvetti et al., "Factors Influencing Recombinant Adeno-Associated Virus Production", *Hum. Gene Ther.*, 20:695-706 (1998).

Samulski et al., "A Recombinant Plasmid from Which an Infectious Adeno-Associated Virus Genome Can Be Excised In Vitro and Its Use To Study Viral Replication", *Journal of Virology*, 61:3096-3101 (1987).

Schwartz et al., "Matrices for Detecting Distant Relationships", Atlas of Protein Sequence and Structure, National Biomedical Research Foundation, pp. 353-358 (1978).

Smith et al., "Comparison of Biosequences", *Advances in Applied Mathematics*, 2:482-489 (1981).

Smith et al., "Single-step purification of polypeptides expressed in *Escherichia coli* as fusions with glutathione S-transferase", *Gene*, 67:31-40 (1988).

Srivastava et al., "Nucleotide Sequence and Organization of the Adeno-Associated Virus 2 Genome", *Journal of Virology*, 45:555-564 (1983).

Tessier et al., "Characterization of Adenovirus-Induced Inverted Terminal Repeat-Independent Amplification of Integrated Adeno-Associated Virus *rep-cap* Sequences", *Journal of Virology*, 75:375-383 (2001).

Translation of PCT Patent Application WO 01/44809, "Methods for Screening or Assessing the Performance of a Collection of Biological Agents in Living Parget Cells, And Their Applications".

Urabe et al., "Charged-to-Alanine Scanning Mutagenesis of the N-Terminal Half of Adeno-Associated Virus Type 2 Rep78 Protein", *Journal of Virology*, 23:2682-2693 (1999).

Walker et al., "Mutational Analysis of the Adeno-Associated Virus Type 2 Rep68 Protein Helicase Motifs", *Journal of Virology*, 71:6996-7004 (1997).

Walker et al., "Mutational Analysis of the Adeno-Associated Virus Rep68 Protein: Identification of Critical Residues Necessary for Site-Specific Endonuclease Activity", *Journal of Virology*, 71:2722-2730 (1997).

Watson et al., "*Molecular Biology of the Gene*", 4th Ed., The Benjamin/Cummings Pub. Co., p. 224, (1987).

Weitzman et al., "Interaction of Wild-Type and Mutant Adeno-Associated Virus (AAV) Rep Proteins on AAV Hairpin DNA", *Journal of Virology*, 70:2240-2248 (1996).

Weitzman et al., "Recruitment of Wild-Type and Recombinant Adeno-Associated Virus into Adenovirus Replication Centers", *Journal of Virology*, 70:1845-1854 (1996).

Wu et al., "Mutational Analysis of the Adeno-Associated Virus Type 2 (AAV2) Capsid Gene and Construction of AAV2 Vectors with Altered Tropism", *J. Virol.*, 74:8635-8647 (2000).

Yang et al., "Mutational Analysis of the Adeno-Associated Virus *rep* Gene", *Journal of Virology*, 66:6058-6069 (1992).

Yang et al., "Analysis of the Terminal Repeat Binding Abilities of Mutant Adeno-Associated Virus Replication Proteins", *Journal of Virology*, 67: 4442-4447 (1993).

Yoon et al., "Amino-Terminal Domain Exchange Redirects Origin-Specific Interactions of Adeno-Associated Virus Rep78 In Vitro", *Journal of Virology*, 75:3230-3239 (2001).

Certified English Translation of PCT Patent Application No. WO 01/44809, "Methods for Screening or Assessing the Performance of a Collection of Biological Agents in Living Target Cells, and their Applications."

Certified English Translation of PCT Patent Application No. WO 01/86291, "Method for Determining the Titer of Biological Agents in Living Target Cells."

Certified English Translation of PCT Patent Application No. WO 02/16606, "Method for Massive Directed Mutagenesis."

Xiao et al., "Construction and Screening of a Multi-Point Site-Specific Mutant Library of Subtilisin E with a Set of Oligonucleotides", 40(4):337-344 (1997).

Charbord et al. "Normal human granulomonocytic bone marrow progenitor cells responsiveness to colony stimulating activity" Nouv.l Rev. Fr. Hématol. 22:357-370 (1980).

Davis et al. "High throughput method for creating and screening recombinant adenoviruses" *Gene Therapy* 5(8):1148-1152 (1998).

Gibrat et al "Surprising similarities in structure comparison" Curr. Opionion in Structural Biology 6(3): 377-385 (1996).

Holm et al "Mapping the protein Universe" Science 273(2):8036-8075 (1996).

Kuhn "Structural basis for the positional specificity of lipoxygenases" Prostaglandins and other lipid mediators 62(3): 255-270 (2000).

Lewerenz et al. "Shared receptor components but distinct complexes for alpha and beta interferons" J. Mol. Biol. 282(3):585-599 (1998).

Manetti et al. "Design and realization of a tailor-made enzyme to modify the molecular recognition of 2-arylpropionic esters by Candida rugosa lipase" Biochem. Biophys. Acta 1543(1): 146-158 (2000).

Moullier et al., "Comparative binding of wheat germ agglutinin and its succinylated form on lymphocytes" *European J. Biochem.* 161:197-204 (1986).

Piehler et al "New Structural and functional aspects of the type I interferon-receptor interaction revealed by comprehensive mutational analysis of the binding interface" J. Biol Chem. 275(51): 40425-40433 (2000).

Schumann et al. "Intracellular Ca2+ inhibits smooth muscle L-type Ca2+ channels by activation of protein phosphatase type 2B and by direct interaction with the channel", *J. General Physiology* 110: 503-513 (1997).

Alam et al., "Expression and purification of a mutant human growth hormone that is resistant to proteolytic cleavage by thrombin, plasmin and human plasma in vitro," Journal of Biotechnology 65: 183-190 (1998).

Chiang et al., "In vivo genetic analysis of bacterial virulence," Annu. Rev. Microbiol. 53: 129-154 (1999).

European Examination Report, issued Dec. 6, 2006, in connection with corresponding European Patent Application No. 02798018.4.

Jones et al., "The rapid generation of mutation data matrices from protein sequences," CABIOS 8:275-282 (1992).

Martin, P., "Beyond the Next Generation of Therapeutic proteins," Oct. 2006, http://www.biotech-online.com/artimg/a20062123243425.PDF (accessed on Jan. 11, 2007) (3 pages).

Media Release: "Nautilus Biotech: Next Generation Biopharmaceuticals (NGB)," Paris, France, Jun. 21, 2004, http://www.prnewswire.co.uk/cgi/news/release?id=125241 (accessed on Jan. 8, 2007) (1 page).

Stabach et al., "Site-directed mutagenesis of alpha II spectrin at codon 1175 modulates its mu-calpain susceptibility," Biochemistry 36:57-65 (1997).

Chang et al., "Identification of functionally important residues of the epidermal growth factor-2 domain of factor IX by alanine-scanning mutagenesis. Residues Asn(89)-Gly(93) are critical for binding factor VIIIa." *J Biol Chem* 277:25393-25399 (2002).

Tomii, K. and M. Kanehisa, "Analysis of amino acid indices and mutation matrices for sequence comparison and structure prediction of proteins," *Protein Engineering*, 9(1):27-36 (1996).

International Search Report, issued Jun. 13, 2008, in connection with co-owned International Application No. PCT/US2007/014219.

Communication from European Patent Office, issued Apr. 14, 2008, in connection with corresponding European Patent Application No. 02798018.4.

Office Action, issued Sep. 16, 2008, in connection with U.S. Appl. No. 10/658,355.

Office Action, issued Dec. 24, 2008, in connection with U.S. Appl. No. 11/707,014.

European Examination Report, issued Jul. 31, 2007, in connection with European Patent Application No. 02798018.4.

U.S. Office Action, issued May 9, 2006, in connection with U.S. Appl. No. 10/658,355.

U.S. Office Action, issued Mar. 12, 2007, in connection with U.S. Appl. No. 10/658,355.

U.S. Office Action, issued Dec. 10, 2007, in connection with U.S. Appl. No. 10/658,355.

European Examination Report, issued Aug. 2, 2005, in connection with European Patent Application No. 03748392.2.

European Examination Report, issued Jun. 2, 2006, in connection with European Patent Application No. 03748392.2.

* cited by examiner

```
        10         20         30         40         50         60
1  MPGFYEIVIKVPSDLDEHLPGISDSFVSWVAEKEWELPPDSDMDLNLIEQAPLTVAEKLQ    60
2  MPGFYEIVIKVPSDLDEHLPGISDSFVNWVAEKEWELPPDSDMDLNLIEQAPLTVAEKLQ    60
3  MPGFYEIVLKVPSDLDEHLPGISNSFVNWVAEKEWELPPDSDMDPNLIEQAPLTVAEKLQ    60
4  MPGFYEIVLKVPSDLDEHLPGISNSFVNWVAEKEWELPPDSDMDPNLIEQAPLTVAEKLQ    60
5  MPGFYEIVLKVPSDLDEHLPGISDSFVSWVAEKEWELPPDSDMDLNLIEQAPLTVAEKLQ    60
6  MPGFYEIVIKVPSDLDGHLPGISDSFVNWVAEKEWELPPDSDMDLNLIEQAPLTVAEKLQ    60
7  MATFYEVIVRVPFDVEEHLPGISDSFVDWVTGQIWELPPESDLNLTLVEQPQLTVADRIR    60
C  MFYE:*VP*D*HLPGIS+SFV:WV*WELPP*SD**+*L*EQLTVA**

70         80         90        100        110        120
1  RDFLVQWRRVSKAPEALFFVQFEKGESYFHLHILVETTGVKSMVLGRFLSQIRDKLVQTI  120
2  RDFLVQWRRVSKAPEALFFVQFEKGESYFHLHILVETTGVKSMVLGRFLSQIRDKLVQTI  120
3  REFLVEWRRVSKAPEALFFVQFEKGETYFHLHVLIETIGVKSMVVGRYVSQIKEKLVTRI  120
4  REFLVEWRRVSKAPEALFFVQFEKGETYFHLHVLIETIGVKSMVVGRYVSQIKEKLVTRI  120
5  REFLVEWRRVSKAPEALFFVQFEKGDSYFHLHILVETVGVKSMVVGRYVSQIKEKLVTRI  120
6  RDFLTEWRRVSKAPEALFFVQFEKGESYFHMHVLVETTGVKSMVLGRFLSQIREKLIQRI  120
7  RVFLYEWNKFSKQ-ESKFFVQFEKGSEYFHLHTLVETSGISSMVLGRYVSQIRAQLVKVV  119
C  R:FL++W*SKE**FFVQFEKG+:YFH*H:L+ET:G**SMV:GR::SQI::*L*:*

130        140        150        160        170        180
1  YRGIEPTLPNWFAVTKTRNGAGGGNKVVDECYIPNYLLPKTQPELQWAWTNMEEYISACL  180
2  YRGIEPTLPNWFAVTKTRNGAGGGNKVVDECYIPNYLLPKTQPELQWAWTNMEEYISACL  180
3  YRGVEPQLPNWFAVTKTRNGAGGGNKVVDDCYIPNYLLPKTQPELQWAWTNMDQYLSACL  180
4  YRGVEPQLPNWFAVTKTRNGAGGGNKVVDDCYIPNYLLPKTQPELQWAWTNMDQYLSACL  180
5  YRGVEPQLPNWFAVTKTRNGAGGGNKVVDDCYIPNYLLPKTQPELQWAWTNMDQYISACL  180
6  YRGIEPTLPNWFAVTKTRNGAGGGNKVVDECYIPNYLLPKTQPELQWAWTNMEQYLSACL  180
7  FQGIEPQINDWVAITKVKK--GGANKVVDSGYIPAYLLPKVQPELQWAWTNLDEYKLAAL  177
C  G:EP:*W*A*TK****GG*NKVVD:*YIP*YLLPK*QPELQWAWTN*::Y:*A*L 190        200        210        220        230        240
1  NLAERKRLVAQHLTHVSQTQEQNKENLNPNSDAPVIRSKTSARYMELVGWLVDRGITSEK  240
2  NLAERKRLVAHDLTHVSQTQEQNKENLNPNSDAPVIRSKTSARYMELVGWLVDRGITSEK  240
3  NLAERKRLVAQHLTHVSQTQEQNKENQNPNSDAPVIRSKTSARYMELVGWLVDRGITSEK  240
4  NLAERKRLVAQHLTHVSQTQEQNKENQNPNSDAPVIRSKTSARYMELVGWLVDRGITSEK  240
5  NLAERKRLVAQHLTHVSQTQEQNKENQNPNSDAPVIRSKTSARYMELVGWLVDRGITSEK  240
6  NLTERKRLVAQHLTHVSQTQEQNKENQNPNSDAPVIRSKTSARYMELVGWLVDKGITSEK  240
7  NLEERKRLVAQFLAESSQRS-QEAASQREFSADPVIKSKTSQKYMALVNWLVEHGITSEK  236
C  NL+ERKRLVA*+L*SQ*Q**+*S**PVI*SKTS**YM*LV*WLV*+GITSEK 250        260        270        280        290        300
1  QWIQEDQASYISFNAASNSRSQIKAALDNAGKIMALTKSAPDYLVGPAPPADIKTNRIYR  300
2  QWIQEDQASYISFNAASNSRSQIKAALDNAGKIMALTKSAPDYLVGPAPPADIKTNRIYR  300
3  QWIQEDQASYISFNAASNSRSQIKAALDNASKIMSLTKTAPDYLVGSNPPEDITKNRIYQ  300
4  QWIQEDQASYISFNAASNSRSQIKAALDNASKIMSLTKTAPDYLVGSNPPEDITKNRIYQ  300
5  QWIQEDQASYISFNAASNSRSQIKAALDNASKIMSLTKTAPDYLVGQNPPEDISSNRIYR  300
6  QWIQEDQASYISFNAASNSRSQIKAALDNAGKIMSLTKTAPDYLVGQQPVEDISSNRIYK  300
7  QWIQENQESYLSFNSTGNSRSQIKAALDNATKIMSLTKSAVDYLVGSSVPEDISKNRIWQ  296
C  QWIQE*Q*SY*SFN***NSRSQIKAALDNA:KIM+LTK:A*DYLVG::**+DI::NRI*:

310        320        330        340        350        360
1  ILELNGYEPAYAGSVFLGWAQKRFGKRNTIWLFGPATTGKTNIAEAIAHAVPFYGCVNWT  360
2  ILELNGYDPAYAGSVFLGWAQKRFGKRNTIWLFGPATTGKTNIAEAIAHAVPFYGCVNWT  360
3  ILELNGYDPQYAASVFLGWAQKKFGKRNTIWLFGPATTGKTNIAEAIAHAVPFYGCVNWT  360
4  ILELNGYDPQYAASVFLGWAQKKFGKRNTIWLFGPATTGKTNIAEAIAHAVPFYGCVNWT  360
5  ILEMNGYDPQYAASVFLGWAQKKFGKRNTIWLFGPATTGKTNIAEAIAHAVPFYGCVNWT  360
6  ILELNGYDPQYAASVFLGWATKKFGKRNTIWLFGPATTGKTNIAEAIAHTVPFYGCVNWT  360
7  IFEMNGYDPAYAGSILYGWCQRSFNKRNTVWLYGPATTGKTNIAEAIAHTVPFYGCVNWT  356
C  I*E*NGY*P:YA:S***GW****:F*KRNT*WL*GPATTGKTNIAEAIAH+VPFYGCVNWT
```

FIG. 5A

```
            370       380       390       400       410       420
1  NENFPFNDCVDKMVIWWEEGKMTAKVVESAKAILGGSKVRVDQKCKSSAQIDPTPVIVTS   420
2  NENFPFNDCVDKMVIWWEEGKMTAKVVESAKAILGGSKVRVDQKCKSSAQIDPTPVIVTS   420
3  NENFPFNDCVDKMVIWWEEGKMTAKVVESAKAILGGSKVRVDQKCKSSAQIEPTPVIVTS   420
4  NENFPFNDCVDKMVIWWEEGKMTAKVVESAKAILGGSKVRVDQKCKSSAQIEPTPVIVTS   420
5  NENFPFNDCVDKMVIWWEEGKMTAKVVESAKAILGGSKVRVDQKCKSSAQIDPTPVIVTS   420
6  NENFPFNDCVDKMVIWWEEGKMTAKVVESAKAILGGSKVRVDQKCKSSAQIDPTPVIVTS   420
7  NENFPFNDCVDKMLIWWEEGKMTNKVVESAKAILGGSKVRVDQKCKSSVQIDSTPVIVTS   416
C  NENFPFNDCVDKM*IWWEEGKMT*KVVESAKAILGGSKVRVDQKCKSS*QI+*TPVIVTS 430       440       450       460       470       480
1  NTNMCAVIDGNSTTFEHQQPLQDRMFKFELTRRLEHDFGKVTKQEVKEFFRWAQDHVTEV   480
2  NTNMCAVIDGNSTTFEHQQPLQDRMFKFELTRRLEHDFGKVTKQEVKEFFRWAQDHVTEV   480
3  NTNMCAVIDGNSTTFEHQQPLQDRMFKFELTRRLDHDFGKVTKQEVKDFFRWASDHVTDV   480
4  NTNMCAVIDGNSTTFEHQQPLQDRMFKFELTRRLDHDFGKVTKQEVKDFFRWASDHVTDV   480
5  NTNMCAVIDGNSTTFEHQQPLQDRMFKFELTKRLEHDFGKVTKQEVKDFFRWASDHVTEV   480
6  NTNMCAVIDGNSTTFEHQQPLQDRMFKFELTRRLDHDFGKVTKQEVKDFFRWAKDHVVEV   480
7  NTNMCVVVDGNSTTFEHQQPLEDRMFKFELTKRLPPDFGKITKQEVKDFFAWAKVNQVPV   476
C  NTNMC*V*DGNSTTFEHQQPL*DRMFKFELT+RL:*DFGK*TKQEVK+FF*WA:***+:V 490       500                          510       520
1  AHEFYVRKGGANKRPAPDDADKSEPKRA-------------------CPSVADPSTSDAEG   522
2  AHEFYVRKGGANKRPAPDDADKSEPKRA-------------------CPSVADPSTSDAEG   522
3  AHEFYVRKGGAKKRPASNDADVSEPKRQ-------------------CTSLAQPTTSDAEA   522
4  AHEFYVRKGGAKKRPASNDADVSEPKRQ-------------------CTSLAQPTTSDAEA   522
5  THEFYVRKGGARKRPAPNDADISEPKRA-------------------CPSVAQPSTSDAEA   522
6  EHEFYVKKGGAKKRPAPSDADISEPKRV-------------------RESVAQPSTSDAEA   522
7  THEFKVPRELAGTKGAEKSLKRPLGDVTNTSYKSLEKRARLSFVPETPRSSDVTVDPAPL   536
C  :HEF*V+*A:*A::*.***:                   +:*:*:*:***A*:

530       540       550       560       570       580
1  APVDFADRYQNKCSRHAGMLQMLFPCKTCERMNQNFNICFTHGTRDCSECFP--GVSESQ   580
2  APVDFADRYQNKCSRHAGMLQMLFPCKTCERMNQNFNICFTHGTRDCSECFP--GVSESQ   580
3  P-ADYADRYQNKCSRHVGMNLMLFPCKTCERMNQISNVCFTHGQRDCGECFPGMSESQPV   581
4  P-ADYADRYQNKCSRHVGMNLMLFPCKTCERMNQISNVCFTHGQRDCGECFPGMSESQPV   581
5  P-VDYADRYQNKCSRHVGMNLMLFPCRQCERMNQNVDICFTHGVMDCAECFP-VSESQPV   580
6  S-INYADRYQNKCSRHVGMNLMLFPCRQCERMNQNSNICFTHGQKDCLECFP--VSESQP   579
7  RPLNWNSRYDCKCDYHAQFDNISNKCDECEYLNRGKNGCICHNVTHCQICHG-------   588
C  ::+:RYKCH:::**C::CEN*:*:C**H::*C.*C**..::+:::

590       600       610       620
1  PVVRKRTYRKLCAIHHLLGRAPEIACSACDLVNVDLDDCVSEQ                    623
2  PVVRKRTYRKLCAIHHLLGRAPEIACSACDLVNVDLDDCVSEQ                    623
3  SVVKKKTYQKLCPIHHILGRAPEIACSACDLANVDLDDCVSEQ                    624
4  SVVKKKTYQKLCPIHHILGRAPEIACSACDLANVDLDDCVSEQ                    624
5  SVVRKRTYQKLCPIHHIMGRAPEVACSACELANVDLDDCDMEQ                    623
6  VSVVKKAYQKLCYIHHIMG-KVPDACTACDLVNVDLDDCIFEQ                    621
7  ------------------IPPWEKENLSDFGDFDDANKEQ                       610
C  :+*:*:+*:***:***::*++++:**:***+:**D*DD*::EQ
```

HIGH THROUGHPUT DIRECTED EVOLUTION BY RATIONAL MUTAGENESIS

RELATED APPLICATIONS

Benefit of priority under 35 U.S.C. §119(e) is claimed to U.S. provisional application Ser. No. 60/315,382, filed Aug. 27, 2001, to Manuel Vega, Lila Drittanti and Marjorie Flaux, entitled "HIGH THROUGHPUT DIRECTED EVOLUTION BY RATIONAL MUTAGENESIS." The subject matter of this application is incorporated in its entirety by reference thereto.

FIELD OF INVENTION

Processes and systems for the high throughput directed evolution of peptides and proteins, particularly those that act in complex biological settings, are provided. The proteins and peptides include, but are not limited to, intracellular proteins, messenger/signaling/hormone proteins and viral proteins.

BACKGROUND

Directed evolution refers to biotechnological processes for optimizing the activity of proteins by means of random changes introduced into selected respective genes. Directed evolution involves the creation of a library of mutated genes, and then selection of the mutants that encode proteins having desired properties. The process can be an iterative one in which gene products that have improvement in a desired property are subjected to further cycles of mutation and screening. Directed evolution provides a way to adapt natural proteins to work in new chemical or biological environments, and/or to elicit new functions. The potential plasticity of proteins is such that chances exist that for every new challenge, such as a new environment and desired new or altered activity, it should be possible, given a sufficient pool of modified proteins (or encoding nucleic acids), that an appropriately 'evolved' protein could be found that would have a desired activity. The problem is in generating and then identifying the appropriate sequence.

There have been practical approaches to this problem (see, e.g., U.S. Pat. Nos. 6,096,548; 6,117,679; 6,165,793; 6,180,406; 6,132,970; 6,171,820; 6,238,884; 6,174,673; 6,057,103; 6,001,574; 5,763,239; 5,837,500; 5,571,698; 6,156,509; 5,723,323; 5,862,514; 5,871,974; 5,779,434 and others). Typically theses approaches are of two types. One is a purely "rational" approach that is based on the assumption that the optimized proteins can be rationally designed. This, however, requires sufficient information regarding the laws that govern protein folding, molecular interactions, intra-molecular forces and other dynamics of protein activity. This rational approach is extremely dependent on a number of variables and parameters that are not known. Consequently, although useful in some specific cases and applications, the rational approach intended to 'predict' protein structure remains limited in applicability.

In contrast to the rational approach, random approaches have also been employed. One random approach requires synthesis of all possible protein sequences or a statistically sufficient large number of proteins and then screening them to identify proteins having the desired activity or property. Since the resources to synthesize all possible theoretical sequences of a single protein is not possible, this approach is impracticable. Other random approaches are based on gene shuffling methods, which are PCR-based methods that generate random rearrangements between two or more sequence-related genes to randomly generate variants of the gene.

The development and scope of directed evolution, thus, has been limited, and its potential remains to be exploited. In order to exploit the potential of directed evolution, alternative approaches for generating and identifying evolved proteins are needed. It is an object herein to provide methods and products to exploit the potential of directed evolution.

SUMMARY

Provided herein are methods for performing directed evolution for the optimization of proteins that function in complex biological settings. Methods of high throughput directed evolution of proteins are provided. In practicing the methods, each molecule is individually designed, produced, processed, screened and tested in a high throughput format. Neither random or combinatorial methods nor mixtures of molecules are used.

The methods provided herein include the steps of identifying a protein target of interest; obtaining nucleic acids that encode the target, which may be from any source, such as a natural library, a collection generated by known gene shuffling techniques and related methods, and, then creating variants of the proteins using methods for rational mutagenesis provided herein. Whatever method is used to select or generate the nucleic acids encoding the protein targets, each molecule is processed and screened separately in a high throughput format.

The nucleic acids encoding each variant are individually screened. They can be screened in any suitable assay, including cell-based assays and biochemical assays. For cell based assays, each nucleic acid molecule is introduced into an expression vector for expression in a bacterial cell or into a vector for expression in a eukaryotic host cell. In all instances, the nucleic acids of interest are introduced into host cells in an expression vector, such as by transfection for bacterial hosts and transduction with viral vectors into eukaryotic hosts with viral vectors.

Each variant is introduced into a host and the resulting cells are maintained separately, such as in an addressable array of wells in a microtiter plate or other substrate with discrete locations for performing reactions or retaining molecules of interest. Typical formats are 96 loci, and multiples thereof (384, 1536, 3072, . . . 96×n, where n is 1 to any number desired, such as 10, 20, 30, 50 . . . 100), although any convenient number of loci may be employed.

Since the process is conducted in a high throughput format, for many embodiments, it is often important to assess the relative numbers of transformed, transduced or transfected cells. Hence the relative (or actual) titer of the vector, such as the recombinant viral vector, must be known to permit analysis of results. For high throughput formats, it is important to assess the relative or actual concentration of the viral vector (or plasmid) so that results can be compared among all cells and variants. Methods for titering (determining the concentration) of the nucleic acid encoding the variant and/or the recombinant virus are also provided.

The processes require accurate titering of the viruses in a collection or among collections (libraries) so that the activities of the screened mutant proteins can be compared. Provided are general methods for the quantitative assessment of the parameters of activity corresponding to the individual variants in the library, based upon intracellular serial dilution generated by precise titering with the gene transfer viral vectors. Any method that permits accurate titering may be used, including that described in International PCT application No.

PCT/FR01/01366, based on French application no 0005852, filed 9 May 2000, and published as International PCT application No. WO 01/186291. A method of titering, designated Tagged Replication and Expression Enhancement Technology (TREE™) is provided herein.

Each of the different cells is separately screened by a suitable assay, and the results analyzed. Methods for assessing the interactions in biological systems, such as a Hill-based analysis (see, published International PCT application No. WO 01/44809 based on PCT/FR00/03503, December, 2000, and the description herein), or a second order polynomial or other algorithm that describes the interaction between cells and biological agents to select variants that have a desired property are employed in the processes herein.

A semi-rational method for evolution of proteins that is particularly designed for use in the methods herein or in any method that uses "evolved" proteins is also provided. The method, which is based on an amino-acid scanning protocol, is for rationally designing the variants for use in the directed evolution and selection method, and can employ iterative processing of the steps of the high throughput methods provided herein. In this method, once the target protein or domain is identified, nucleic acid molecules encoding variants are prepared. Each variant encoded by the nucleic acid molecules has a single amino acid replaced with another selected amino acid, such as alanine (Ala), glycine (Gly), serine (Ser) or any other suitable amino acid, typically one selected to have a neutral effect on secondary and tertiary structure. The resulting series of variants are separately screened in the high throughput format provided herein, and those that have a change in the target activity are selected and the modified amino acids are designated "hits." Nucleic acid molecules encoding proteins in which each hit position is replaced by the eighteen remaining amino acids then are synthesized and the resulting collection of molecules is screened, such by introduction into host cells, and the proteins that result in an improvement of a targeted activity, are identified. Such proteins are designated "leads." Leads may be further modified by producing proteins that have combinations of the mutations identified in the leads. This method, which does not require any knowledge of the structure of a target protein, permits precise control of locations where changes are introduced and also the amount of change that is introduced.

The high throughput directed evolution processes provided herein include the use of virus libraries containing mutant versions of a gene; viral libraries of such mutant genes are also provided.

Reporter cells are infected with the titered viruses that encode the mutant genes. The mutant genes are expressed and read-out data from either biochemical or cell-based assays, while isolating each mutant/virus physically from the others (i.e. one-by-one analysis), are collected and analyzed. Serial dilution assays (i.e. a series of dilutions for each individual mutant/virus in the library) are used and the biochemical/cell-based assays are performed on each single dilution for each individual mutant/virus. Analysis of the serial dilution read-out-data can be performed using any method of analysis that permits one-by-one comparisons. Hill-based analysis (see, published International PCT application No. WO 01/44809 based on PCT/FR00/03503, December, 2000, and the description herein) are employed for analysis of the data.

Protein/protein domain variants identified using the methods are also provided. Also provided are nucleic acid molecules and proteins and polypeptides produced by the methods and viruses and cells that contain the nucleic acid molecules and proteins.

In an exemplary embodiment of methods provided herein, the process of rational directed evolution provided herein is applied to the AAV rep gene. The resulting recombinant rep protein variants and rAAV are also provided. Among the rep proteins are those that result in increased rAAV production in rAAV that encode such mutants, thereby, among a variety of advantages, offering a solution to the need in the gene therapy industry to increase the production therapeutic vectors without up-scaling manufacturing.

Thus, for exemplification, some methods provided herein have been used to identify amino acid "hit" positions in adeno-associated virus (AAV) rep proteins that are relevant for AAV or rAAV production. Those amino acid positions are such that a change in the amino acid leads to a change in protein activity either to lower activity or to higher activity compared to native-sequence Rep proteins. The hit positions were then used to generate further mutants designated "leads." Provided herein are the resulting mutant rep proteins that result in either higher or lower levels of AAV or rAAV virus compared to the wild-type (native) Rep protein(s).

In addition to enhancing AAV production, among the rep mutants are those that inhibit papillomavirus (PV) and PV-associated diseases, including certain cancers and human immunodeficiency virus (HIV) and HIV-associated diseases.

Systems and computer controlled systems for performing the high throughput processes are also provided.

DESCRIPTION OF THE FIGURES

FIG. 1A depicts an embodiment of the process in which an amino acid scan is employed to generate a library of mutants, which are then introduced into viral vectors, such as an adeno-associated viral vector (AAV), a herpes virus, such as herpes simplex virus (HSV) and other herpes virus vectors, a vaccinia virus vector, retroviral vectors, such as MuMLV, MoMLV, feline leukemia virus, and HIV and other lentiviruses, adenovirus vectors and other suitable viral vector, each member of the library is individually tested and phenotypically characterized to identify HITS. FIG. 1B summarizes round 2 in which LEADS are developed by mutagenesis at and/or surrounding the positions identified as HITS; FIG. 1C summarizes the optional next round in which recombination among LEADS is performed to further optimize the LEADS; FIG. 1D depicts the process in mammalian cells; and FIG. 1E depicts the process in bacterial cells.

FIGS. 5A and 5B show the alignment of amino acid sequences of Rep78 among AAV-1; AAV-6; AAV-3; AAV-3B; AAV-4; AAV-2; AAV-5 sequences, respectively; the hit positions with 100 percent homology among the serotypes are bolded italics, where the position is different (compared to AAV-2, no. 6 in the Figure) in a particular serotype, it is in bold; a sequence indicating relative conservation of sequences among the serotypes is labeled "C".

Figure 1A:
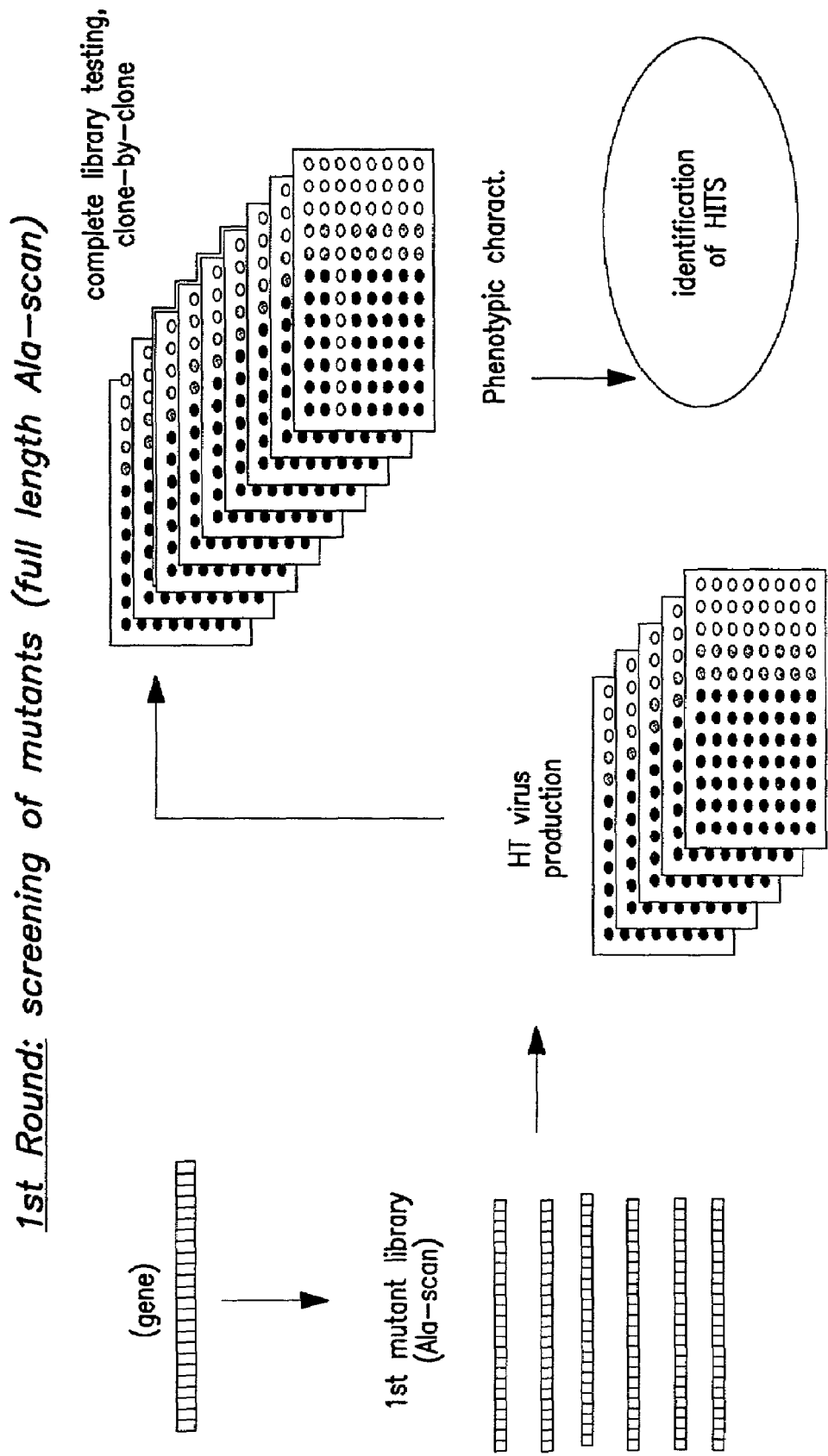
FIGS. 1A-1E summarize various exemplary embodiments of the high throughput processes provided herein.
Figure 1B:
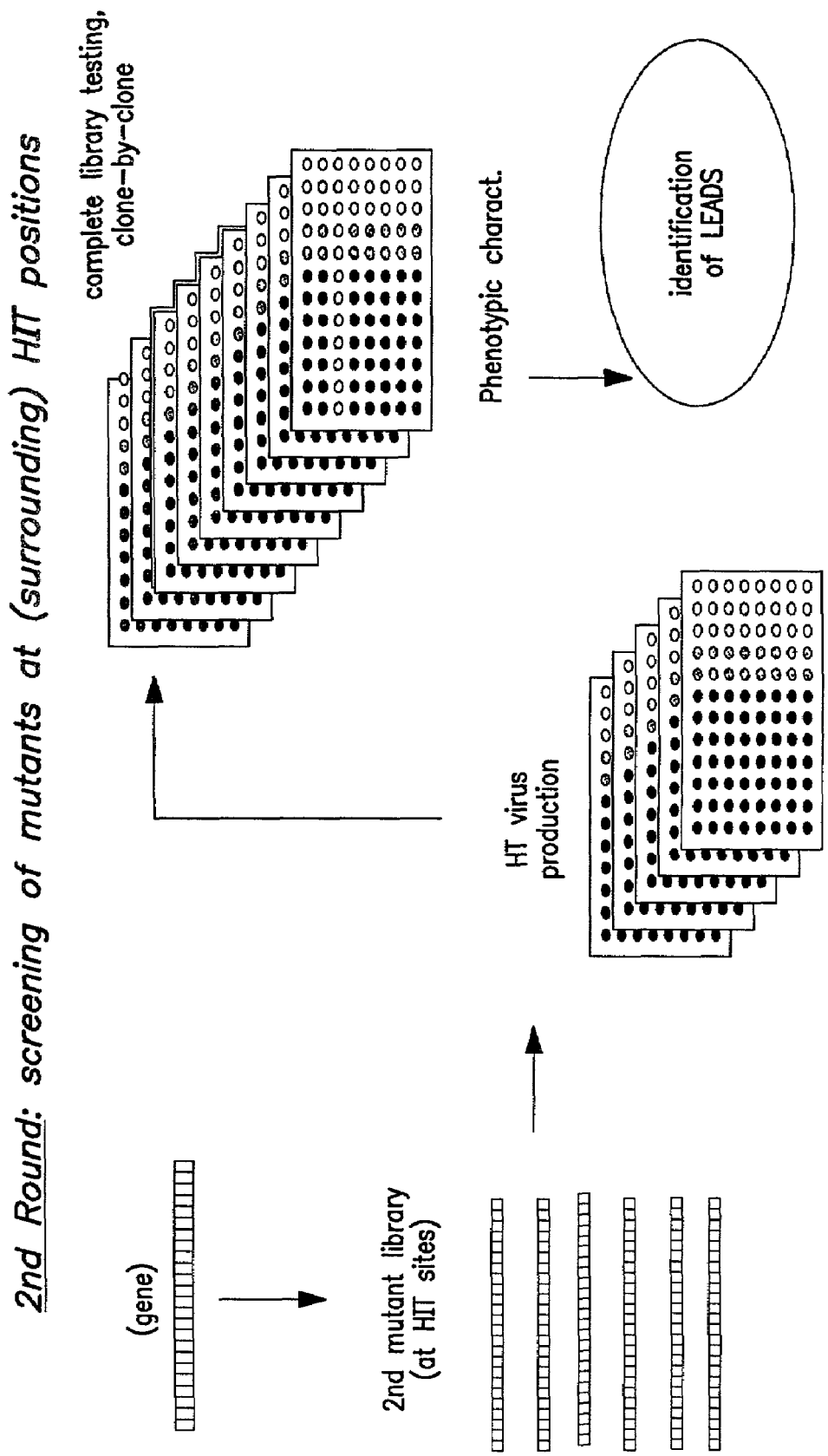
Figure 1C:
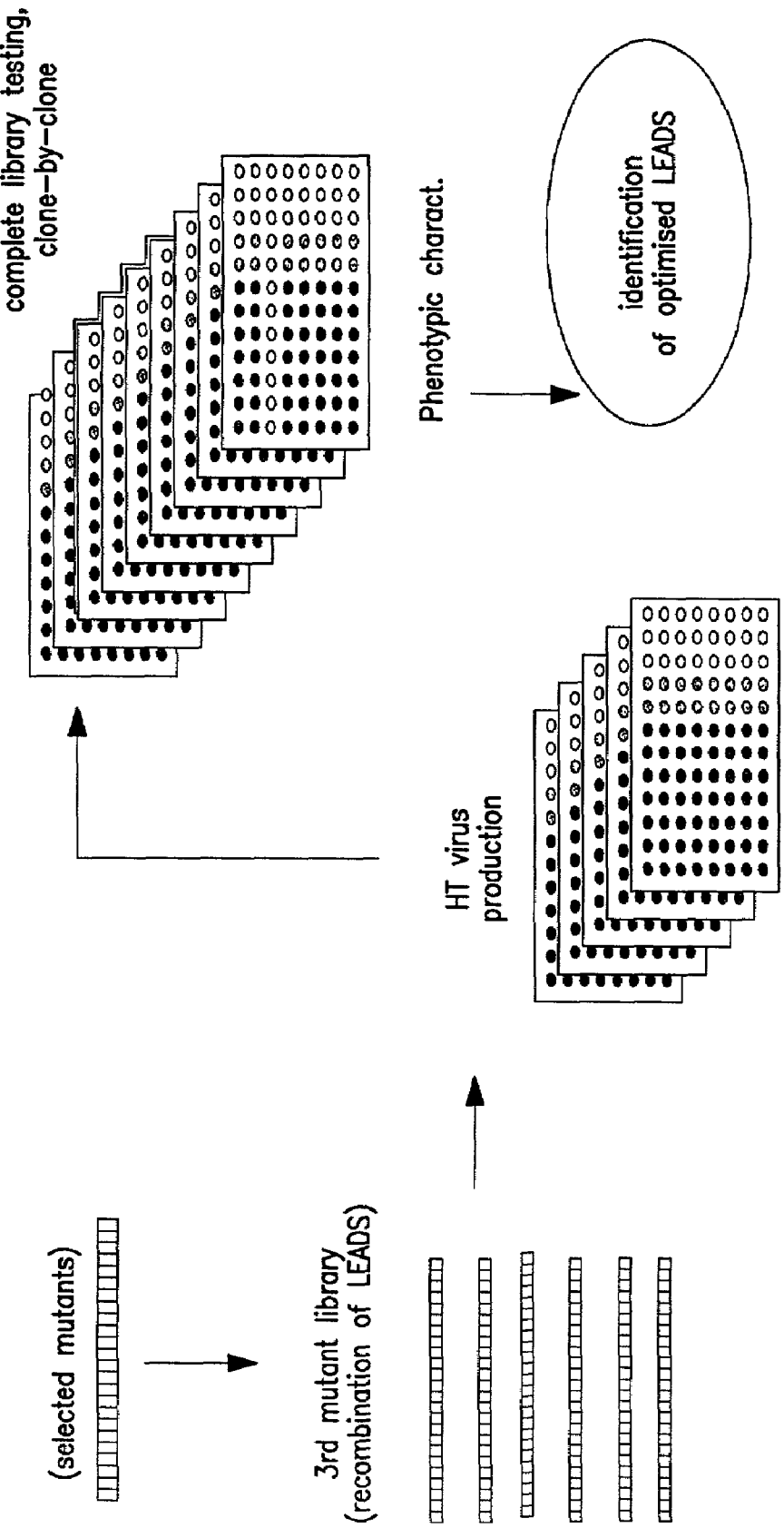
Figure 1D:
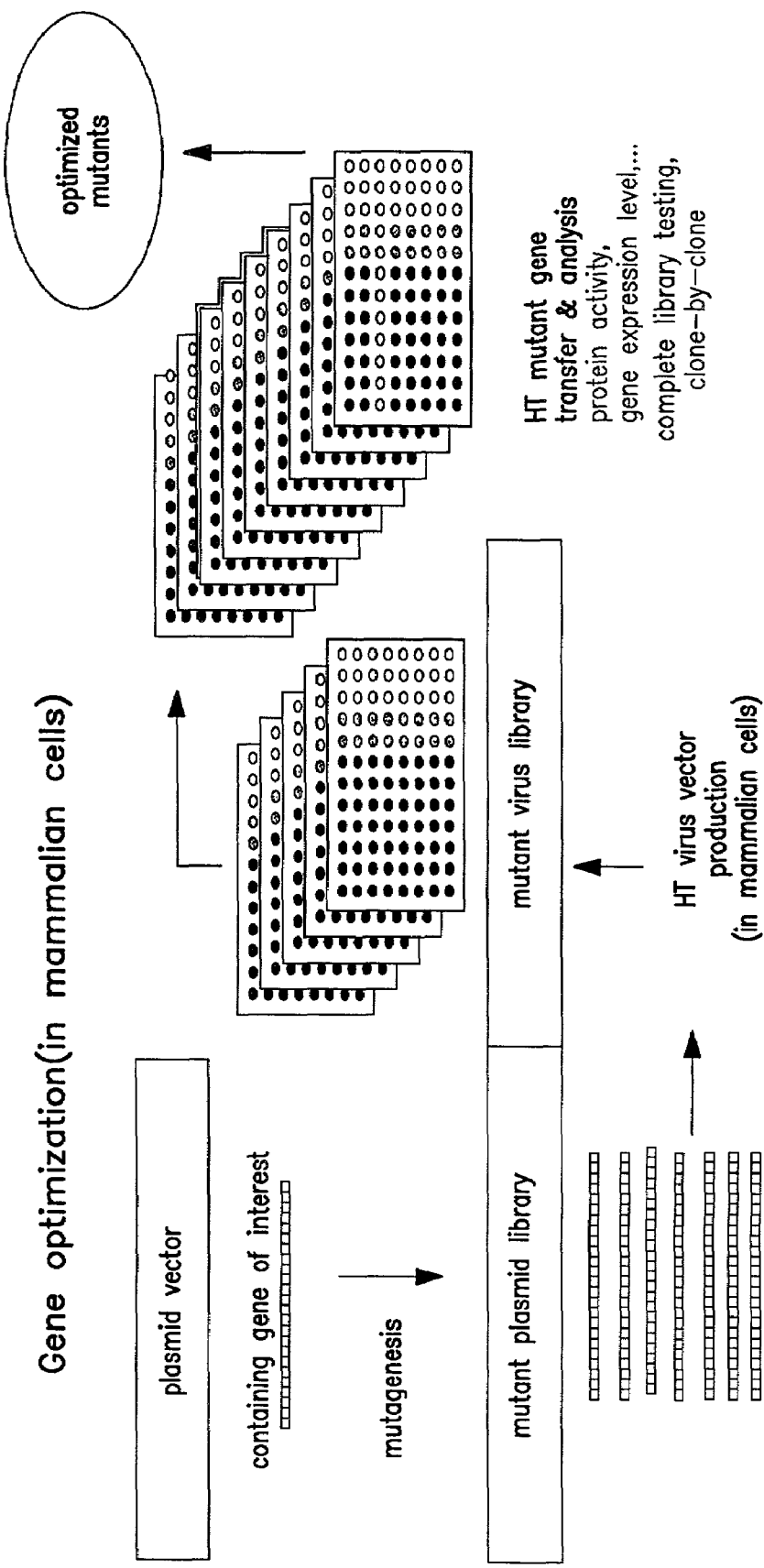
Figure 1E:
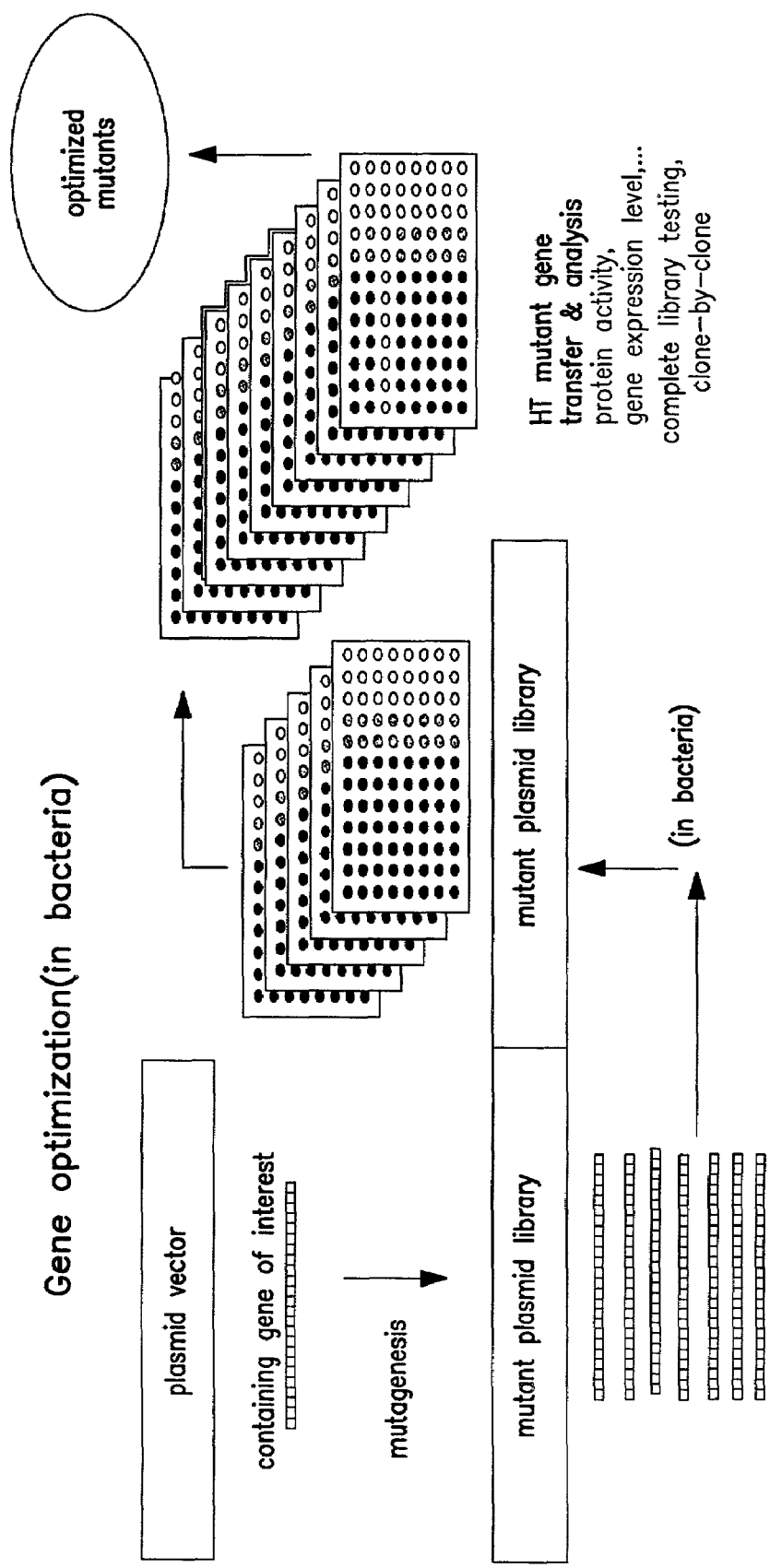

LEGEND 1 is AAV-1; 2 is AAV-6, 3 is AAV-3, 4 is AAV-3B,
5 is AAV-4, 6 is AAV-2, and 7 is AAV-5;
"." where the amino acid is present ≧20%;
":" where the amino acid is present ≧40%;
"+" where the amino acid is present ≧60%;
"*" where the amino acid is present ≧80%; and
where the amino acid is the same amongst all serotypes depicted it is represented by its single letter code.

DETAILED DESCRIPTION

A. Definitions

Unless defined otherwise, all technical and scientific terms used herein have the same meaning as is commonly understood by one of skill in the art to which this invention belongs. All patents, patent applications, published applications and publications, Genbank sequences, websites and other published materials referred to throughout the entire disclosure herein are, unless noted otherwise, incorporated by reference in their entirety. In the event that there are a plurality of definitions for terms herein, those in this section prevail.

As used herein, directed evolution refers to methods that adapt natural proteins or protein domains to work in new chemical or biological environments and/or to elicit new functions. It is more a more broad-based technology than DNA shuffling.

As used herein, high-throughput screening (HTS) refers to processes that test a large number of samples, such as samples of test proteins or cells containing nucleic acids encoding the proteins of interest to identify structures of interest or to identify test compounds that interact with the variant proteins or cells containing them. HTS operations are amenable to automation and are typically computerized to handle sample preparation, assay procedures and the subsequent processing of large volumes of data.

As used herein, DNA shuffling is a PCR-based technology that produces random rearrangements between two or more sequence-related genes to generate related, although different, variants of given gene.

As used herein, "hits" are mutant proteins that have an alteration in any attribute, chemical, physical or biological property in which such alteration is sought. In the methods herein, hits are generally generated by systematically replacing each amino acid in a protein or a domain thereof with a selected amino acid, typically Alanine, Glycine, Serine or any amino acid, as long as each residue is replaced with the same residue. Hits may be generated by other methods known to those of skill in the art and tested by the high throughput methods herein. For purposes herein a Hit typically has activity with respect to the function of interest that differs by at least 10%, 20%, 30% or more from the wild type or native protein. The desired alteration, which is generally a reduction in activity, will depend upon the function or property of interest.

As used herein, "leads" are "hits" whose activity has been optimized for the particular attribute, chemical, physical or biological property. In the methods herein, leads are generally produced by systematically replacing the hit loci with all remaining 18 amino acids, and identifying those among the resulting proteins that have a desired activity. The leads may be further optimized by replacement of a plurality of "hit" residues. Leads may be generated by other methods known to those of skill in the art and tested by the highthroughput methods herein. For purposes herein a lead typically has activity with respect to the function of interest that differs from the native activity, by a desired amount and by at least 10%, 20%, 30% or more from the wild type or native protein. Generally a Lead will have an activity that is 2 to 10 or more times the native protein for the activity of interest. As with hits, the change in the activity is dependent upon the activity that is "evolved." The desired alteration will depend upon the function or property of interest.

As used herein, MOI is multiplicity of infection.

As used herein, ip, with reference to a virus or recombinant vector, refers to a titer of infectious particles.

As used herein, pp refers to the total number of vector (or virus) physical particles As used herein, biological and pharmacological activity includes any activity of a biological pharmaceutical agent and includes, but is not limited to, biological efficiency, transduction efficiency, gene/transgene expression, differential gene expression and induction activity, titer, progeny productivity, toxicity, cytotoxicity, immunogenicity, cell proliferation and/or differentiation activity, anti-viral activity, morphogenetic activity, teratogenetic activity, pathogenetic activity, therapeutic activity, tumor suppressor activity, ontogenetic activity, oncogenetic activity, enzymatic activity, pharmacological activity, cell/tissue tropism and delivery.

As used herein, "output signal" refers to parameters that can be followed over time and, if desired, quantified. For example, when a virus infects a cell, the infected cell undergoes a number of changes. Any such change that can be monitored and used to assess infection, is an "output signal," and the cell is referred to as a "reporter cell." Output signals include, but are not limited to, enzyme activity, fluorescence, luminescence, amount of product produced and other such signals. Output signals include expression of a viral gene or viral gene product, including heterologous genes (transgenes) inserted into the virus. Such expression is a function of time ("t") after infection, which in turn is related to the amount of virus used to infect the cell, and, hence, the concentration of virus ("s") in the infecting composition. For higher concentrations the output signal is higher. For any particular concentration, the output signal increases as a function of time until a plateau is reached. Output signals may also measure the interaction between cells, expressing heterologous genes, and biological agents As used herein, adeno-associated virus (AAV) is a defective and non-pathogenic parvovirus that requires co-infection with either adenovirus or herpes virus for its growth and multiplication, able of providing helper functions. A variety of serotypes are known, and contemplated herein. Such serotypes include, but are not limited to: AAV-1 (Genbank accession no. NC002077; accession no. VR-645); AAV-2 (Genbank accession no. NC001401; accession no. VR-680); AAV-3 (Genbank accession no. NC001729; accession no. VR-681); AAV-3b (Genbank accession no. NC001863); AAV-4 (Genbank accession no. NC001829; ATCC accession no. VR-646); AAV-6 (Genbank accession no. NC001862); and avian associated adeno-virus (ATCC accession no. VR-1449). The preparation and use of AAVs as vectors for gene expression in vitro and for in vivo use for gene therapy are well known (see, e.g., U.S. Pat. Nos. 4,797,368, 5,139, 941, 5,798,390 and 6,127,175; Tessier et al. (2001) *J. Virol.* 75:375-383; Salvetti et al. (1998) *Hum Gene Ther* 20:695-706; Chadeuf et al. (2000) *J Gene Med* 2:260-268).

As used herein, the activity of a Rep protein or of a capsid protein refers to any biological activity that can be assessed. In particular, herein, the activity assessed for the rep proteins is the amount (i.e., titer) of AAV produced by a cell.

As used herein, the Hill equation is a mathematical model that relates the concentration of a drug (i.e., test compound or substance) to the response being measured $$y = \frac{y_{max}[D]^x}{[D]^n + [D_{50}]^n},$$

where y is the variable being measured, such as a response, signal, $y_{max}$ is the maximal response achievable, [D] is the molar concentration of a drug, $[D_{50}]$ is the concentration that produces a 50% maximal response to the drug, n is the slope parameter, which is 1 if the drug binds to a single site and with no cooperativity between or among sites. A Hill plot is $\log_{10}$ of the ratio of ligand-occupied receptor to free receptor vs. log [D] (M). The slope is n, where a slope of greater than 1 indicates cooperativity among binding sites, and a slope of less than 1 can indicate heterogeneity of binding. This general equation has been employed for assessing interactions in complex biological systems (see, published International PCT application No. WO 01/44809 based on PCT no PCT/FR00/03503, see, also, EXAMPLES).

As used herein, in the Hill-based analysis (published International PCT application No. WO 01/44809 based on PCT no PCT/FR00/03503), the parameters, π, κ, τ, ε, η, θ, are as follows:

π potency of the biological agent acting on the assay (cell-based) system;

κ constant of resistance of the assay system to elicit a response to a biological agent;

ε is global efficiency of the process or reaction triggered by the biological agent on the assay system;

τ is the apparent titer of the biological agent;

θ is the absolute titer of the biological agent; and

η is the heterogeneity of the biological process or reaction.

In particular, as used herein, the parameters π (potency) or κ (constant of resistance) are used to respectively assess the potency of a test agent to produce a response in an assay system and the resistance of the assay system to respond to the agent.

As used herein, ε(efficiency), is the slope at the inflection point of the Hill curve (or, in general, of any other sigmoidal or linear approximation), to assess the efficiency of the global reaction (the biological agent and the assay system taken together) to elicit the biological or pharmacological response.

As used herein, τ (apparent titer) is used to measure the limiting dilution or the apparent titer of the biological agent.

As used herein, θ (absolute titer), is used to measure the absolute limiting dilution or titer of the biological agent.

As used herein, η (heterogeneity) measures the existence of discontinuous phases along the global reaction, which is reflected by an abrupt change in the value of the Hill coefficient or in the constant of resistance.

As used herein, a library of mutants refers to a collection of plasmids or other vehicles that carry (encode) the gene variants, such that individual plasmids or other vehicles carry individual gene variants. When a library of proteins is contemplated, it will be so-stated.

As used herein, a "reporter cell" is the cell that "reports", i.e., undergoes the change, in response to introduction of the nucleic acid infection and, therefore, it is named here a reporter cell.

As used herein, "reporter" or "reporter moiety" refers to any moiety that allows for the detection of a molecule of interest, such as a protein expressed by a cell. Reporter moieties include, but are not limited to, for example, fluorescent proteins, such as red, blue and green fluorescent proteins; lacZ and other detectable proteins and gene products. For expression in cells, nucleic acid encoding the reporter moiety can be expressed as a fusion protein with a protein of interest or under the control of a promoter of interest.

As used herein, a titering virus increases or decreases the output signal from a reporter virus, which is a virus that can be detected, such as by a detectable label or signal.

As used herein, phenotype refers to the physical or other manifestation of a genotype (a sequence of a gene). In the methods herein, phenotypes that result from alteration of a genotype are assessed.

As used herein, activity refers to the function or property to be evolved. An active site refers to a site(s) responsible or that participates in conferring the activity or function. The activity or active site evolved (the function or property and the site conferring or participating in conferring the activity) may have nothing to do with natural activities of a protein. For example, it could be an 'active site' for conferring immunogenicity (immunogenic sites or epitopes) on a protein.

As used herein, the amino acids, which occur in the various amino acid sequences appearing herein, are identified according to their known, three-letter or one-letter abbreviations (see, Table 1). The nucleotides, which occur in the various nucleic acid fragments, are designated with the standard single-letter designations used routinely in the art.

As used herein, amino acid residue refers to an amino acid formed upon chemical digestion (hydrolysis) of a polypeptide at its peptide linkages. The amino acid residues described herein are presumed to be in the "L" isomeric form. Residues in the "D" isomeric form, which are so-designated, can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in J. Biol. Chem., 243:3552-59 (1969) and adopted at 37 C.F.R. §§ 1.821-1.822, abbreviations for amino acid residues are shown in the following Table:

TABLE 1

Table of Correspondence

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues or to an amino-terminal group such as NH$_2$ or to a carboxyl-terminal group such as COOH.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. co., p. 224).

Such substitutions are preferably made in accordance with those set forth in TABLE 2 as follows:

TABLE 2

| Original residue | Conservative substitution |
| --- | --- |
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Pro (P) | Ala; Gly |
| Ser (S) | Thr |
| Thr (T) | Ser |
| Trp (W) | Tyr |
| Tyr (Y) | Trp; Phe |
| Val (V) | Ile; Leu |

Other substitutions are also permissible and may be determined empirically or in accord with known conservative substitutions.

As used herein, nucleic acids include DNA, RNA and analogs thereof, including protein nucleic acids (PNA) and mixture thereof. Nucleic acids can be single or double stranded. When referring to probes or primers, optionally labeled, with a detectable label, such as a fluorescent or radiolabel, single-stranded molecules are contemplated. Such molecules are typically of a length such that they are statistically unique of low copy number (typically less than 5, preferably less than 3) for probing or priming a library. Generally a probe or primer contains at least 14, 16 or 30 contiguous of sequence complementary to or identical to a gene of interest. Probes and primers can be 10, 14, 16, 20, 30, 50, 100 or more nucleic acid bases long.

As used herein, homologous means about greater than 25% nucleic acid sequence identity, preferably 25% 40%, 60%, 80%, 90% or 95%. The intended percentage will be specified. The terms "homology" and "identity" are often used interchangeably. In general, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, N.J., 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carillo et al. (1988) *SIAM J Applied Math* 48:1073). By sequence identity, the number of conserved amino acids are determined by standard alignment algorithms programs, and are used with default gap penalties established by each supplier. Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

As used herein, a nucleic acid homolog refers to a nucleic acid that includes a preselected conserved nucleotide sequence, such as a sequence encoding a therapeutic polypeptide. By the term "substantially homologous" it is meant having at least 80%, preferably at least 90%, most preferably at least 95% homology therewith or a less percentage of homology or identity and conserved biological activity or function.

The terms "homology" and "identity" are often used interchangeably. In this regard, percent homology or identity may be determined, for example, by comparing sequence information using a GAP computer program. The GAP program uses the alignment method of Needleman and Wunsch (*J. Mol. Biol.* 48:443 (1970), as revised by Smith and Waterman (*Adv. Appl. Math.* 2:482 (1981). Briefly, the GAP program defines similarity as the number of aligned symbols (i.e., nucleotides or amino acids) which are similar, divided by the total number of symbols in the shorter of the two sequences. The preferred default parameters for the GAP program may include: (1) a unitary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps.

Whether any two nucleic acid molecules have nucleotide sequences that are, for example, at least 80%, 85%, 90%, 95%, 96%, 97%, 98% or 99%, "identical" can be determined using known computer algorithms such as the "FAST A" program, using for example, the default parameters as in Pearson and Lipman, *Proc. Natl. Acad. Sci. USA* 85:2444 (1988). Alternatively the BLAST function of the National Center for Biotechnology Information database may be used to determine identity In general, sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, N.J., 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM JApplied Math* 48:1073 (1988). Methods to determine identity and similarity are codified in computer programs. Preferred computer program methods to determine identity and similarity between two sequences include, but are not limited to, GCG program package (Devereux, J., et al., *Nucleic Acids Research* 12(I):387 (1984)), BLASTP, BLASTN, FASTA (Atschul, S. F., et al., *J Molec Biol* 215:403 (1990)), and CLUSTALW. For sequences displaying a relatively high degree of homology, alignment can be effected manually by simply lining up the sequences and manually or visually matching the conserved portions.

Therefore, as used herein, the term "identity" represents a comparison between a test and a reference polypeptide or polynucleotide. For example, a test polypeptide may be defined as any polypeptide that is 90% or more identical to a reference polypeptide.

For the alignments presented herein (see, FIG. 5) for the AAV serotype, the CLUSTALW program was employed with parameters set as follows: scoring matrix BLOSUM, gap open 10, gap extend 0.1, gap distance 40% and transitions/transversions 0.5; specific residue penalties for hydrophobic amino acids (DEGKNPQRS), distance between gaps for which the penalties are augmented was 8, and gaps of extremities penalized less than internal gaps.

As used herein, a "corresponding" position on a protein, such as the AAV rep protein, refers to an amino acid position based upon alignment to maximize sequence identity. For AAV Rep proteins an alignment of the Rep 78 protein from AAV-2 and the corresponding protein from other AAV serotypes (AAV-1, AAV-6, AAV-3, AAV-3B, AAV-4, AAV-2 and AAV-5) is shown in FIG. 5. The "hit" positions are shown in italics.

As used herein, the term at least "90% identical to" refers to percent identities from 90 to 100% relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons may be made between a test and reference polynucleotides. Such differences may be represented as point mutations randomly distributed over the entire length of an amino acid sequence or they may be clustered in one or more locations of varying length up to the maximum allowable, e.g. 10/100 amino acid difference (approximately 90% identity). Differences are defined as nucleic acid or amino acid substitutions, or deletions.

As used herein, it is also understood that the terms substantially identical or similar varies with the context as understood by those skilled in the relevant art.

As used herein, genetic therapy involves the transfer of heterologous nucleic acids to the certain cells, target cells, of a mammal, particularly a human, with a disorder or conditions for which such therapy is sought. The nucleic acid, such as DNA, is introduced into the selected target cells in a manner such that the heterologous nucleic acid, such as DNA, is expressed and a therapeutic product encoded thereby is produced. Alternatively, the heterologous nucleic acid, such as DNA, may in some manner mediate expression of DNA that encodes the therapeutic product, or it may encode a product, such as a peptide or RNA that in some manner mediates, directly or indirectly, expression of a therapeutic product. Genetic therapy may also be used to deliver nucleic acid encoding a gene product that replaces a defective gene or supplements a gene product produced by the mammal or the cell in which it is introduced. The introduced nucleic acid may encode a therapeutic compound, such as a growth factor or inhibitor thereof, or a tumor necrosis factor or inhibitor thereof, such as a receptor therefor, that is not normally produced in the mammalian host or that is not produced in therapeutically effective amounts or at a therapeutically useful time. The heterologous nucleic acid, such as DNA, encoding the therapeutic product may be modified prior to introduction into the cells of the afflicted host in order to enhance or otherwise alter the product or expression thereof. Genetic therapy may also involve delivery of an inhibitor or repressor or other modulator of gene expression.

As used herein, heterologous or foreign nucleic acid, such as DNA and RNA, are used interchangeably and refer to DNA or RNA that does not occur naturally as part of the genome in which it is present or which is found in a location or locations in the genome that differ from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Heterologous DNA and RNA may also encode RNA or proteins that mediate or alter expression of endogenous DNA by affecting transcription, translation, or other regulatable biochemical processes. Examples of heterologous nucleic acid include, but are not limited to, nucleic acid that encodes traceable marker proteins, such as a protein that confers drug resistance, nucleic acid that encodes therapeutically effective substances, such as anti-cancer agents, enzymes and hormones, and DNA that encodes other types of proteins, such as antibodies.

Hence, herein heterologous DNA or foreign DNA, includes a DNA molecule not present in the exact orientation and position as the counterpart DNA molecule found in the genome. It may also refer to a DNA molecule from another organism or species (i.e., exogenous).

As used herein, a therapeutically effective product introduced by genetic therapy is a product that is encoded by heterologous nucleic acid, typically DNA, that, upon introduction of the nucleic acid into a host, a product is expressed that ameliorates or eliminates the symptoms, manifestations of an inherited or acquired disease or that cures the disease.

As used herein, isolated with reference to a nucleic acid molecule or polypeptide or other biomolecule means that the nucleic acid or polypeptide has separated from the genetic environment from which the polypeptide or nucleic acid were obtained. It may also mean altered from the natural state. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as an "isolated polypeptide" or an "isolated polynucleotide" are polypeptides or polynucleotides that have been purified, partially or substantially, from a recombinant host cell or from a native source. For example, a recombinantly produced version of a compounds can be substantially purified by the one-step method described in Smith and Johnson, *Gene* 67:31-40 (1988). The terms isolated and purified are sometimes used interchangeably.

Thus, by "isolated" it is meant that the nucleic is free of the coding sequences of those genes that, in the naturally-occurring genome of the organism (if any), immediately flank the gene encoding the nucleic acid of interest. Isolated DNA may be single-stranded or double-stranded, and may be genomic DNA, cDNA, recombinant hybrid DNA, or synthetic DNA. It may be identical to a native DNA sequence, or may differ from such sequence by the deletion, addition, or substitution of one or more nucleotides.

Isolated or purified as it refers to preparations made from biological cells or hosts means any cell extract containing the indicated DNA or protein including a crude extract of the DNA or protein of interest. For example, in the case of a protein, a purified preparation can be obtained following an individual technique or a series of preparative or biochemical techniques and the DNA or protein of interest can be present at various degrees of purity in these preparations. The procedures may include for example, but are not limited to, ammonium sulfate fractionation, gel filtration, ion exchange change chromatography, affinity chromatography, density gradient centrifugation and electrophoresis.

A preparation of DNA or protein that is "substantially pure" or "isolated" should be understood to mean a preparation free from naturally occurring materials with which such DNA or protein is normally associated in nature. "Essentially pure" should be understood to mean a "highly" purified preparation that contains at least 95% of the DNA or protein of interest.

A cell extract that contains the DNA or protein of interest should be understood to mean a homogenate preparation or cell-free preparation obtained from cells that express the protein or contain the DNA of interest. The term "cell extract" is intended to include culture media, especially spent culture media from which the cells have been removed.

As used herein, receptor refers to a biologically active molecule that specifically binds to (or with) other molecules. The term "receptor protein" may be used to more specifically indicate the proteinaceous nature of a specific receptor.

As used herein, recombinant refers to any progeny formed as the result of genetic engineering.

As used herein, a promoter region refers to the portion of DNA of a gene that controls transcription of the DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerase. These sequences may be cis acting or may be responsive to trans acting factors. Promoters, depending upon the nature of the regulation, may be constitutive or regulated.

As used herein, the phrase "operatively linked" generally means the sequences or segments have been covalently joined into one piece of DNA, whether in single or double stranded form, whereby control or regulatory sequences on one segment control or permit expression or replication or other such control of other segments. The two segments are not necessarily contiguous. For gene expression a DNA sequence and a regulatory sequence(s) are connected in such a way to control or permit gene expression when the appropriate molecules, e.g., transcriptional activator proteins, are bound to the regulatory sequence(s).

As used herein, production by recombinant means by using recombinant DNA methods means the use of the well known methods of molecular biology for expressing proteins encoded by cloned DNA, including cloning expression of genes and methods, such as gene shuffling and phage display with screening for desired specificities.

As used herein, a splice variant refers to a variant produced by differential processing of a primary transcript of genomic DNA that results in more than one type of mRNA.

As used herein, a composition refers to any mixture of two or more products or compounds. It may be a solution, a suspension, liquid, powder, a paste, aqueous, non-aqueous or any combination thereof.

As used herein, a combination refers to any association between two or more items.

As used herein, substantially identical to a product means sufficiently similar so that the property of interest is sufficiently unchanged so that the substantially identical product can be used in place of the product.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form, are not bound to the chromosome. "Plasmid" and "vector" are used interchangeably as the plasmid is the most commonly used form of vector. Other such forms of expression vectors that serve equivalent functions and that become known in the art can be used subsequently hereto.

As used herein, vector is also used interchangeable with "virus vector" or "viral vector". In this case, which will be clear from the context, the "vector" is not self-replicating. Viral vectors are engineered viruses that are operatively linked to exogenous genes to transfer (as vehicles or shuttles) the exogenous genes into cells.

As used herein, transduction refers to the process of gene transfer and expression into mammalian and other cells mediated by viruses. Transfection refers to the process when mediated by plasmids.

As used herein, "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, referred to as a single nucleotide polymorphism (SNP), the identity of which differs in different alleles. A polymorphic region can also be several nucleotides in length.

As used herein, "polymorphic gene" refers to a gene having at least one polymorphic region.

As used herein, "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene can also be a form of a gene containing a mutation.

As used herein, the term "gene" or "recombinant gene" refers to a nucleic acid molecule comprising an open reading frame and including at least one exon and (optionally) an intron sequence. A gene can be either RNA or DNA. Genes may include regions preceding and following the coding region (leader and trailer).

As used herein, "intron" refers to a DNA sequence present in a given gene which is spliced out during mRNA maturation.

As used herein, "nucleotide sequence complementary to the nucleotide sequence set forth in SEQ ID NO: x" refers to the nucleotide sequence of the complementary strand of a nucleic acid strand having SEQ ID NO: x. The term "complementary strand" is used herein interchangeably with the term "complement". The complement of a nucleic acid strand can be the complement of a coding strand or the complement of a non-coding strand. When referring to double stranded nucleic acids, the complement of a nucleic acid having SEQ ID NO: x refers to the complementary strand of the strand having SEQ ID NO: x or to any nucleic acid having the nucleotide sequence of the complementary strand of SEQ ID NO: x. When referring to a single stranded nucleic acid having the nucleotide sequence SEQ ID NO: x, the complement of this nucleic acid is a nucleic acid having a nucleotide sequence which is complementary to that of SEQ ID NO: x.

As used herein, the term "coding sequence" refers to that portion of a gene that encodes an amino acid sequence of a protein.

As used herein, the term "sense strand" refers to that strand of a double-stranded nucleic acid molecule that has the sequence of the mRNA that encodes the amino acid sequence encoded by the double-stranded nucleic acid molecule.

As used herein, the term "antisense strand" refers to that strand of a double-stranded nucleic acid molecule that is the complement of the sequence of the mRNA that encodes the amino acid sequence encoded by the double-stranded nucleic acid molecule.

As used herein, an array refers to a collection of elements, such as nucleic acid molecules, containing three or more members. An addressable array is one in which the members of the array are identifiable, typically by position on a solid phase support or by virtue of an identifiable or detectable label, such as by color, fluorescence, electronic signal (ire. radiofrequency (RF), microwave or other frequency that does not substantially alter the interaction of the molecules of interest), bar code or other symbology, chemical or other such label. Hence, in general the members of the array are immobilized to discrete identifiable loci on the surface of a solid phase or directly or indirectly linked to or otherwise associated with the identifiable label, such as affixed to a microsphere or other particulate support (herein referred to as beads) and suspended in solution or spread out on a surface.

As used herein, a support (also referred to as a matrix support, a matrix, an insoluble support or solid support) refers to any solid or semisolid or insoluble support to which a molecule of interest, typically a biological molecule, organic molecule or biospecific ligand is linked or contacted. Such materials include any materials that are used as affinity matrices or supports for chemical and biological molecule syntheses and analyses, such as, but are not limited to: polystyrene, polycarbonate, polypropylene, nylon, glass, dextran, chitin, sand, pumice, agarose, polysaccharides, dendrimers, buckyballs, polyacrylamide, silicon, rubber, and other materials used as supports for solid phase syntheses, affinity separations and purifications, hybridization reactions, immunoassays and other such applications. The matrix herein can be particulate or can be in the form of a continuous surface, such as a microtiter dish or well, a glass slide, a silicon chip, a nitrocellulose sheet, nylon mesh, or other such materials. When particulate, typically the particles have at least one dimension in the 5-10 mm range or smaller. Such particles, referred collectively herein as "beads", are often, but not necessarily, spherical. Such reference, however, does not constrain the geometry of the matrix, which may be any shape, including random shapes, needles, fibers, and elongated. Roughly spherical "beads", particularly microspheres that can be used in the liquid phase, are also contemplated. The "beads" may include additional components, such as magnetic or paramagnetic particles (see, e.g., Dyna beads (Dynal, Oslo, Norway)) for separation using magnets, as long as the additional components do not interfere with the methods and analyses herein.

As used herein, matrix or support particles refers to matrix materials that are in the form of discrete particles. The particles have any shape and dimensions, but typically have at least one dimension that is 100 mm or less, 50 mm or less, 10 mm or less, 1 mm or less, 100 µm or less, 50 µm or less and typically have a size that is 100 mm$^3$ or less, 50 mm$^3$ or less, 10 mm$^3$ or less, and 1 mm$^3$ or less, 100 µm$^3$ or less and may be order of cubic microns. Such particles are collectively called "beads."

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. High Throughput Process

Provided herein are high throughput processes for the generation of and identification of proteins that exhibit desired phenotypes. The processes include methods that are particularly adapted for high throughput protocols, which require accurate methods for identifying modified proteins.

A general directed evolution process includes the following steps:

1. Generation of diversity at the nucleic acid level, on the gene to be 'evolved'
2. phenotypic characterization of the gene variants generated; and
3. identification of optimized gene variants.

The processes provided herein effect these steps that can be performed in a high throughput format (see, FIG. 1) that is optionally automated. A distinguishing characteristic of the processes provided herein, is that each candidate nucleic acid molecule is separately generated and screened. In an automated process at least some of the steps are performed without human intervention and are generally controlled by software. Most, if not all steps, are performed in addressable formats, such as at discrete locations in or on solid supports, such as microtiter plates or in other addressable formats, such as linked to coded supports. The supports can be electronically, physically, chemically or otherwise identifiable, such as by an identifiable symbology, including a bar code, or can be color coded.

1. Generation of Diversity Using a Semi-Rational Approach

A semi-rational approach to creating diversity or evolving genes is provided herein. The goal is to create diversity but to decrease the number of molecules to be screened. By reducing the numbers, the molecules can be screened in high throughput format molecule-by-molecule (or groups thereof).

Generation of diversity at the nucleic acid level, in principle, can be accomplished by a number of diverse technologies like mutagenesis (either site-directed or random), recombination, shuffling and de-novo synthesis. These different technologies differ in the degree of diversity they generate as well as in the minimal length of the unitary change they can introduce (from single base to large domains). The outcome of step 1 is a collection of diverse, although highly related, molecules that constitutes what is called a 'library'.

This step is crucial, since it provides the initial conditions for the entire process and is determinative of the outcome. The chances of finding an optimized gene version in a library is a function of the total diversity present in the library. In addition, the type of diversity introduced (such as, but not limited to, single point mutations, multiple point mutations, scarce small rearrangements, recombination of large domains, multiple shuffling) condition the outcome, particularly with respect to the generation of new variants compared to the original gene, and the probability that the new variants, not only exhibit the "evolved" function or property, but also work in their natural biological networks where they are expected to act by interacting, recognizing, and/or being recognized, by a large panoply of other proteins and other molecules.

Rapid Discovery of Protein Variants at the Amino Acid Level by Rational Mutagenesis (aa-Scan)

A method, referred to herein as an amino-acid scan method for directed evolution, is provided herein for generating protein variants. This method can be performed on an entire protein or selected domains thereof, or can be used to identify benchmark sequences, such as functional domains, and, for example, recombine them as exchangeable units or restrict the diversity to limited or specific regions of the protein. Not only can this method be used with the processes provided herein, but it also has applications for any methods that use such variants or require generation of such variants, such as, but not limited to, searches for consensus sequences and homology regions that are used in functional genomics, functional proteomics; comparative modeling in protein crystallography and protein modeling; searches for natural diversity, (e.g., directed evolution methods in U.S. Pat. No. 6,171,820, U.S. Pat. No. 6,238,884, U.S. Pat. No. 6,174,673, U.S. Pat. No. 6,057,103, U.S. Pat. No. 6,001,574, U.S. Pat. No. 5,763,239,); exon- or family-shuffling-based diversity (e.g., directed evolution using gene shuffling (see, e.g., U.S. Pat. Nos. 6,096,548, 6,117,679, 6,165,793, 6,180,406, 6,132,970); the optimization of only the CDRs regions (e.g., directed evolution of antibodies see., e.g., U.S. Pat. Nos. 5,723,323, 6,258,530, 5,770,434, 5,862,514) and other methods (see, e.g., U.S. Pat. Nos. 5,837,500, 5,571,698, 6,156,509).

The amino-acid scanning-based method provided herein has advantages that prior methods do not have. For example, prior methods are based upon the underlying assumption that there are parts of the molecule (gene or protein) that are sufficiently adapted to perform their respective function, and further changes are not advantageous. Such methods do not look at total potential plasticity of a given molecule, but at the plasticity still permitted while keeping some basic functions in place. By choosing this route, however, additional potential variation is missed. The potential in the intrinsic plasticity of those regions that are presumed 'preserved' is lost. For instance, methods (e.g., those in U.S. Pat. Nos. 6,171,820, 6,238,884, 6,174,673, 6,057,103, 6,001,574, 5,763,239) that use natural diversity can miss the potential plasticity within those regions that are naturally 'conserved', i.e. there where there is no natural diversity. Methods that rely on exon- or family-shuffling-based diversity can miss the potential plasticity within regions contained in the shuffled fragments, i.e. within the fragments exchanged as a block.

The method provided herein in contrast is sufficiently flexible to create mutants at a variety of levels, including at the single amino acid level; i.e. the method can generate mutants that differ from each other at a single amino and not at a larger block level. The challenge solved by the method herein is to generate diversity at the single amino acid level, without moving too close to a pure 'random' approach, which results in an intractable number of mutants.

The method provided herein is based on the premise that there are single amino acids or small blocks of sequence of amino acids that are either (1) directly involved in the activities that the methods 'evolve' (these amino acids would be at or close to the 'active sites' of the protein); or (2) directly involved in maintaining within the protein the intra-molecular environment that allows the active site(s) to stay active.

Potential plasticity at the amino acid level can be exploited if amino acids or blocks of amino acids directly involved in the active sites for the activity to be evolved are known. Often they are not known. The problem that is solved herein, however, is how to exploit the potential plasticity at the amino acid level when nothing is known about the structure of the protein in question or about the position of its single or numerous active sites.

The technology referred to herein as amino acid-scanning has been used to precisely identify those amino acids directly involved in the active sites of some enzymes and receptors (see, e.g., Becl-Sickinger et al. (1994) *Eur. J. Biochem.* 223: 947-958; Gibbs et al. (1991)*J. Biol. Chem.* 266:8923-8931; Matsushita et al. (2000) *J. Biol. Chem.* 275:11044-11049) but has not been employed for directed evolution or for the generation of diversity. The amino acid scan as practiced in the prior art is used to produce a set of protein mutants, often within the region suspected to contain the active site(s), such that in each individual mutant a selected residue, such as Ala, replaces a different amino acid. Ala or other neutral amino acids generally, although not necessarily, is selected as a replacement amino acid since, except in instances in which the replaced amino acid is directly involved in an active site, it should have a neutral effect on the protein activity and not disturb the native secondary structure of the protein. In instances in which the replaced amino acid is directly involved in an active site the activity of that site will be lost or altered. Amino-acid scanning, such as Ala-scanning, has been successfully applied for the identification of active sites in a number of proteins, and has been performed in computer-based rational drug design methods. Other amino acids, particularly amino acids that have a neutral effect, such as Glycine, can also be used.

The amino acid scanning method is employed herein for the generation of the mutant proteins for screening for identification of sites or loci in a target protein or regions in a protein that alter a selected activity. In performing this method, the amino acids are each replaced, one-by-one along the full-length of the protein, or one-by-one in pre-selected domains, such as domains that possess a desired activity or exhibit a particular function. Once sites of interest are identified other methods for generating diversity from the resulting molecules can be employed or the further steps of the method provided herein can be performed.

The method includes the following steps:

(1) Identification of the active site(s) on the full length protein sequence. In one embodiment a full-length amino acid-scan, typically, although not necessarily, an Ala-scan, or the identification and positioning of the active site(s) on proteins of either known or unknown function. For purposes herein, an active site is not necessarily the natural active site involved in the natural activity of a target protein, but those amino acids involved in the activities of the proteins under 'directed evolution' with the purpose of either gain, improvement or loss of function.

The whole process of the 'identification of the active site(s) on the full length protein sequence requires the following sub-steps:

a. Generation of a mutant library (on the gene to be evolved) in which each individual mutant contains a single mutation located at a different amino acid position and that includes a systematic replacement of the native amino acid by Ala or any other amino acid (always the same throughout the entire protein sequence);
b. phenotypic characterization of the individual mutants, one-by-one and assessment of mutant protein activity;
c. identification of those mutants that display an alteration, typically a decrease, in the selected protein activity, thus, indicating that amino acids directly involved in the active site(s) have been hit. The aa positions whose aa-scan mutations display an alteration, typically a loss or decrease, in activity are named HITS.

The identification of the active site(s) (HITS) is thus, by this method, made in a completely unbiased manner. There are no assumptions about the specific structure of the protein in question nor any knowledge or assumptions about the active site(s). The results of the amino acid scan identify such sites.

Once the active site(s) (the HITS) has(ve) been identified, those amino acids either at or surrounding the active sites, such as within 1, 2, 3, . . . 10, 20 or any selected regions, as the unitary elements of exchange and generate diversity either at or around one of those sites or as a combined diversity at several sites at a time can be assessed. This process includes the following steps:

a. Generation of a new mutant library (on the gene to be evolved) in which each individual mutant contains either single or multiple mutations located at (or surrounding) a specific active site (a HIT) position detected by the precedent aa-scan process. In the example these mutations include replacement, in each individual mutant, of the native amino acid located either at (or surrounding) the HIT position by one of all other possible amino acids, such that, in the library, and at (or surrounding) each HIT position the native amino acid has been replaced by all possible amino acids.
b. Identification of those mutants that display an increase in protein activity, thus indicating that a new sequence at or surrounding an active site has been identified with higher activity compared to the native sequence. These optimized sequences are named LEADS.

The process can be repeated as many times as desired, in search for new combinations of optimal amino acids at (or surrounding) the different HIT sites. Each time, the process includes the steps of generating of a new mutant library (of the gene to be evolved) in which each individual mutant contains either single or multiple mutations located at (or surrounding) a specific active site (a HIT) position; phenotypic characterization of the individual mutants, one-by-one and assessment of mutant protein activity; and identification of those mutants that display an increase in protein activity, thus indicating that a new sequence at or surrounding an active site has been identified with higher activity compared to the native sequence. These optimized sequences are again named LEADS (second generation LEADS).

2. Phenotypic Characterization of the Gene Variants

This step requires the expression of the gene variants in order to allow them to manifest their respective phenotypes. Gene expression can be accomplished by different means: in vitro, in reconstituted systems or in vivo in cellular systems, including bacterial and eukaryotic cells. For all exemplification purposes, reference is made to in vivo systems. Those of skill in the art can readily adapt these methods for in vitro systems, including those using biochemical assays.

This step is a crucial step for several reasons:

(a) Expression system and protein processing.

Depending on the system used (either bacteria or eukaryotic cells), as well as on the specific gene to be 'evolved', the variant proteins may or may not be appropriately processed, especially when post-translational modifications are involved, and therefore be able or not to elicit their potential activity. Consequently, the expression system (bacteria vs. eukaryotic cells) has to be carefully chosen.

(b) Standardization of the expression system.

The technologies available for gene transfer and expression into either bacteria or eukaryotic (let's consider mammalian) cells widely vary in their intrinsic efficiencies. While it is very easy to efficiently transfer and express genes in bacteria by chemical/physical methods (transformation), that is not the case for mammalian cells, where the transformation (here called transfection) process is inefficient and unreliable, especially when reproducibility and robustness are necessary in miniature, large number- and small scale high throughput settings like those necessary to analyze gene variant libraries. Therefore, when transfection is used on mammalian cells, the specific activity measured for the individual variants in the library most probably does not accurately reflect the real specific activity of the molecules involved. As provided herein, transduction, the process of gene transfer and expression into mammalian and other cells mediated by viruses, overcomes the limitations of transfection.

(3) Characterization

A distinction must be made between the 'expression' of the gene variants and their 'phenotypic characterization'. The expression system (either bacteria or mammalian cells) is only the vehicle to convert the gene variants into protein variants. The phenotypic characterization is performed on the protein variants, and may have nothing to do, depending on the specific system under study, with the cellular system used to express the variants. The phenotypic characterization requires the use of specific assays (either biochemical (cell-free) or cell-based assays) in which the activity of the different cell mutants is challenged and assessed. In addition to the implications discussed below, these assays must be designed in such a way that they reflect the final environment in which the 'evolved' protein is expected to act. As an example, when optimizing an enzyme to be used in an artificial industrial setting, the assay should reproduce those conditions (temperature, pH, media composition . . . ) of the real-life industrial reaction mixture, which may be relatively easy to do. When the final destination of the 'evolved' protein is a complex biological setting, such as the intracellular environment, the extra-cellular milieu (example: circulating proteins) or the structure of a virus, the necessary assay(s) may be quite difficult to setup. With a few exceptions, most of the work done so far on directed evolution has been made on simple enzymes for which all the necessary settings are relatively easy to implement.

Methods for Accurately Titering Viruses

Much progress in gene therapy, genomics, biotechnology and, in general, biomedical sciences, depends on the ability to generate and analyze large numbers and small amounts of specific viruses. High throughput technologies are employed in disciplines such as functional genomics and gene therapy in which the use of viruses plays a key role for the efficient transfer and analysis of large collections of genes or libraries. Also, virus samples and biomedical samples containing viruses are routinely analyzed in thousands of hospitals, health centers, academic labs and biotech settings.

Furthermore in processes herein, accurate titration can be important in at least two steps in the process. After preparation of the viruses with the mutated variant, and prior to screening, it is necessary to know the concentration of titer of the viruses in the sample, so that results among the samples can be compared. The methods in this section designated Real Time Virus Titering (RTVT™) and (TREE) are advantageously used.

The methods in this section are also used in data analysis when measuring the output signal. As described below, output signal can be assessed by a Hill analysis or a second order polynomial or other algorithm that describes the interaction of biological molecules in complex system. In addition, where the output signal is actually the number of viral particles or ip produced, the methods in this section RTVT and TREE are advantageously used.

Prior art virus titration methods (RCA, dRA . . . ), for determining the amount of virus present in a biological sample, are based on the assessment of some kind of output signal, such as cytopathic effect, lysis or plaques and cell fusion focuses, induced in a reporter cell following a fixed time after infection with varying concentrations of the sample containing the virus. The lowest concentration of the sample at which no signal can be measured is taken as the titer of the virus in that sample. These approaches are known as "serial dilution" or "limiting dilution" methods. In limiting dilution methods, one single virus concentration, measured at a given time end-point gives rise to a single measurement of the output signal. These methods tend to be destructive in that assessment destroys the reaction so that only a single measurement can be taken on a sample.

Real Time Virus Titering (RTVT™)

When a virus infects a cell, the infected cell undergoes a number of changes that can be followed over time and quantified. Such changes are designated herein as the "output signal". The cell reports an output signal in response to the infection and, therefore, it is named here a reporter cell. One such output signal, is, for example, the expression of the genes carried by the virus (whether they are viral genes or exogenous genes (transgenes)). The output signal (for instance the level of expression of those genes) develops over time and depends, mainly, on two factors: i) the time point ("t") at which its level is measured after infection and ii) the amount of virus infecting the cell; i.e. the concentration of the virus preparation used to infect the cell ("s"). The output signal, at a given time point after infection, will be higher for higher concentrations of the virus infecting the reporter cells; and for any given concentration of virus, the output signal increases with time after infection until it generally reaches a plateau level.

Real Time Virus Titering (RTVT™) published as International POT application No. WO 01/186291, which is based on POT/FR01/01366 and EXAMPLES below) uses non-destructive methods for the assessment of output signal. Real Time Virus Titering is a viral titration method based on the kinetic analysis of the development of the output signal in virus-infected cells, tested at a single concentration of virus or biological sample. Instead of fixing the time point after infection and varying the concentration of the sample as is done in limiting dilution methods, in the Real Time Virus Titering RTVT™ method, a fixed concentration of virus is used and the generation of a signal over time is assessed. Hence the signal is measured as a function of time at a single virus concentration. In this situation, a single virus sample (concentration), whose output signal is measured at a number of time points, can give rise to as many measurements of the output signal as needed, and, eventually to a continuous, over time, assessment of the signal in real time.

Real Time Virus Titering RTVT™ can be advantageously used in high throughput methods in which large numbers of biological samples are analyzed at the same time. This is the case, for instance, when titering viruses in a virus library. Limiting dilution methods rely on the output signal generated by a number of dilutions of each individual sample. If, for example, 10 dilutions (or experimental points) of each virus are used for a titration using a limiting dilution method, the analysis of a library containing 10,000 viruses require analysis of $10^5$ (i.e., 10×10,000) experimental points. The Real Time Virus Titering RTVT™ method requires only one dilution per sample, thereby requiring 10-fold fewer experimental points than a limiting dilution method. For a Real Time Virus Titering RTVT™ titering system, the time (tβ) necessary for the output signal to reach a reference value (β) is a direct function of the concentration of virus. Thus, t/β can be used to directly determine the concentration of the virus.

A limitation of the Real Time Virus Titering RTVT™ limiting dilution titering method, however, is that not all the viruses (nor the genes carried by the viruses) generate a readily measured output signal that can be followed over time using non-destructive methods.

Tagged Replication and Expression Enhancement (TREE)

A method for titering designated Tagged Replication and Expression Enhancement Technology (TREE™) is provided herein. This system includes: i) a cell, ii) a reporter virus carrying a reporter gene, whose activity can be followed over time by a non-destructive method (i.e., fluorescence), iii) the virus (or virus library to be titered), herein referred to as the "titering virus". The elements are employed such that the virus to be titered interferes with any output signal generated by the reporter virus, leading to either decrease or increase in the amount of that signal. The higher the amount of virus to be titered, the higher is the interference with the reporter virus and output signal. In the absence of virus to be titered, the kinetics of the output signal generated by the reporter virus are followed using the Real Time Virus Titering RTVT™ titering method. In the presence of increasing amounts of the virus to be titered the output signal takes longer (or shorter) to develop as a function of the amount of virus to be titered.

Using the TREE™ titering method, tβ, the time necessary for the output signal to reach a reference value (β) is a direct function of the concentration of virus and, therefore, tβ can be used to determine the concentration of the virus to be titered. It is demonstrated herein (see the EXAMPLES) that when using the TREE system for titering, once an appropriate reference value (β) is determined for the output signal generated from the reporter virus, the time tβ is a function of the concentration of the virus being titered (see Example). Therefore, the concentration (titer) of the virus to be titered, can be assessed by assessing the change induced in tβ by an aliquot of the virus to be titered. In a calibrated TREE titering assay, only one aliquot virus to be titered is needed to determine its titer, which is determined by measuring the shift in the tβ of the system. The only condition is that the virus to be titered must "interfere" (i.e., increase or decrease) the output signal of the reporter virus.

A calibration curve representing tβ vs. the amount of virus to be titered is obtained using aliquots of a reference batch of virus of known titer (previously determined using any titering procedure). The calibration curve can then be used to determine the amount of virus in a sample of unknown titer, based on the change caused by an aliquot of the sample on the tβ of the system and the corresponding titer read from the calibration curve.

3. Identification of Gene Variants

There are at least two considerations in this step:

(a) Selection vs. Screening

Depending on the specific protein involved, and under certain and very specific assay conditions, those variants that have been 'evolved' may elicit a selective advantage over the native version. This situation represents the most simple case: the cells (bacteria or mammalian) expressing the library of protein variants, as a pool or mixture, can be simply exposed to the selective conditions which by themselves will allow to put in evidence the best optimized variants. This situation is however very rare and difficult to achieve. It can be hardly believed that for any protein that one may want to optimize, a suitable 'selective' assay could be set up. For the vast majority of the cases, selection will not be possible. Therefore pools of molecules cannot be used, because the specific readouts of the assays could not be attributed to individual variants. When the simplistic selection approach is not possible, then two things are absolutely needed: (a) a 'one-by-one' approach, i.e. each individual variant must be physically separated from the others and its activity tested independently; (b) an accurate and quantitative analysis that can distinguish slight differences in activity among the different variants along a wide range of performance values.

(b) Accurate Quantitative Analytics

When selection is not possible, the optimized variants must be distinguished from the native variant otherwise. The different degrees of optimization among the different variants in the library should, in addition, be distinguished if those variants showing the highest optimization level are to be identified. A powerful quantitative analytical protocol is then mandatory. These analytics should be able to attribute quantitative features (on the activity tested in the specific assay) to each of the variants tested and to rank them according to their individual performance. This requires, in addition, that each variant in the library is assayed individually; the use of pools or mixtures of molecules would hamper the ability to identify the right variants.

For such analysis, the output signal can be assessed by a Hill analysis (see Examples and (published International PCT application No. WO 01/44809 based on PCT no PCT/FR00/03503),.) or a second order polynomial (see, Examples and (Drittanti et al. (2000) Gene Ther. 7: 924-929)) or other algorithm that describes the interaction of biological molecules in complex system, such as the interaction between cells and biological agents. In addition, where the output signal is actually the number of viral particles or ip produced, the methods in this designated Real Time Virus Titering (RTVT™) and Tagged Replication and expression enhancement (TREE™) are advantageously used (for a discussion of RTVT™, see, International PCT application No. PCT/FR01/01366 published as International PCT application No. WO 01/186291 and the EXAMPLES below) or a refinement of that method provide herein and designated Tagged Replication and expression enhancement (TREE™) described above and in the examples.

C. Practice of the Process

In one embodiment, the process provided herein includes the following steps.

1. Generation of Diversity or Source of Existing Diversity

Generation of a plasmid library containing the genetic variants. The genetic variants are physically separated from each other. Any model such as, but not limited to, amino acid scanning, mutagenesis, or recombination may be used to generate the plasmid library.

2. Expression of the Genetic Variants

Any method for expression of variants is contemplated. In particular the following alternatives are particularly suitable for high throughput performance.

a. Expression in Bacterial Hosts

The mutated forms of the nucleic acid are prepared or introduced into plasmids for expression in bacterial cells. The genetic variants are expressed from suitable bacterial cells, which are prepared by transformation of aliquots of the cells with each member of the plasmid library (each genetic variant continues to be physically separated from each other).

b. Expression in Eukaryotic Host Cells

A virus library is generated from the plasmid library. The virus library, in which each different member is separately maintained, is prepared by:

(1) Transfection of the plasmid library into appropriate virus-producer cells (viruses produced, each one carrying a different genetic variant present in the original plasmid library, are physically separated from each other);

(2) Titration of the virus library (of each individual virus present in the library, separately). Titration is effected by any method; but generally by either a method designated Real Time Virus Titering (RTVT™) (see, International PCT application No. PCT/FR01/01366 published as International PCT application No. WO 01/186291 and the EXAMPLES below) or a refinement of that method provided herein and designated Tagged Replication and expression enhancement (TREE™) described above and in the examples;

(3) Standardization of the virus library to equal concentrations of all the individual viruses in the library (individual viruses continue to be physically separated from each other);

(4) Expression of the genetic variants from appropriate mammalian cells by transduction with the virus library (each genetic variant continues to be physically separated from each other and each individual virus is handled separately from the others).

3. Phenotypic Characterization of the Variant Proteins

The variant proteins are expressed (from either plasmids in bacterial cells (step 2) or viruses in mammalian cells (step 4)) and their activity is assessed in one or more appropriate specific assays. The assays can be both types: biochemical (cell-free) assays and/or cell-based assays. The variant proteins in the library are physically separated from each other and their activity is individually assessed on a one-by-one basis.

The assays can be performed in one of a variety of ways, including, but are not limited to:

a. Using a single-point dilution for each individual variant protein, followed by a kinetic analysis (multiple time points) of the read-out by technologies like Tagged Replication and expression enhancement (TREE™), or any other appropriate technology b. Using serial dilutions of each individual variant protein, followed by, for example, the Hill-based analysis of the read-out by technologies or any other appropriate technology. Hill based analyses assess the interaction between cells and biological agents (see, published International PCT application No. WO 01/44809 based on PCT no PCT/FR00/03503).

The goal of these methods is to identify proteins having an evolved function or property.

Lead Identification

Based on the results obtained from the assays described above, each individual protein variant is individually tested for the parameters that assess the activity, property, function or structure of interest. Variants are ranked out according to their activity features. Those variant proteins best suited for the specificities of each individual project and system under study are then selected. The selected leads can be used for the desired purpose or further evolved or mutated to achieve desired activities.

Typically, as for most directed evolution methods, the process is an iterative one, in which mutated variants are produced, screened, the best identified and then selected. The selected variants are then subjected to further evolution and the screening process repeated. This is repeated until the desired goal is achieved.

This further evolution may employ the methods herein or any directed evolution method or combinations thereof. The methods for variant production will include the amino-acid scan method herein, which provides a rational approach to variant generation. Other rounds can include combinations of any other method for directed evolution known and/or combinations thereof.

D. Directed Evolution of a Viral Gene

Recombinant viruses have been developed for use as gene therapy vectors. Gene therapy applications are hampered by the need for development of vectors with traits optimized for this application. The high throughput methods provided herein are ideally suited for development of such vectors. In addition to use for development of recombinant viral vectors for gene therapy, these methods can also be used to study and modify the viral vector backbone architecture, trans-complementing helper functions, where appropriate, regulatable and tissue specific promoters and transgene and genomic sequence analyses. Recombinant AAV (rAAV) is a gene therapy vector that can serve as a model for application of the methods herein for these and other purposes.

Adeno-associated virus (AAV) is a defective and non-pathogenic parvovirus that requires co-infection with either adenovirus or herpes virus, which provide helper functions, for its growth and multiplication. There is an extensive body of knowledge regarding AAV biology and genetics (see, e.g., Weitzman et al. (1996) *J. Virol.* 70: 2240-2248 (1996); Walker et al. (1997) *J. Virol.* 71:2722-2730; Urabe et al. (1999) *J. Virol.* 23:2682-2693; Davis et al. (2000) *J. Virol.* 23:74:2936-2942; Yoon et al. (2001) *J. Virol.* 75:3230-3239; Deng et al. (1992) *Anal Biochem* 200:81-85; Drittanti et al. (2000) *Gene Therapy* 7:924-929; Srivastava et al. (1983) *J. Virol.* 45:555-564; Hermonat et al. (1984) *J. Virol.* 51:329-339; Chejanovsky et al. (1989) *Virology* 173:120-128; Chejanovsky et al. (1990) *J. Virol.* 64:1764-1770; Owens et al. (1991) *Virology* 184:14-22; Owens et al. (1992) *J. Virol.* 66:1236-1240; Qicheng Yang et al. (1992) *J. Virol.* 66:6058-6069; Qicheng Yang et al. (1993) *J. Virol.* 67:4442-4447; Owens et al. (1993) *J. Virol.* 62:997-1005; Sirkka et al. (1994) *J. Virol.* 68:2947-2957; Ramesh et al. (1995) *Biochem. Biophy. Res. Com.* Vol 210 (3), 717-725; Sirkka (1995) *J. Virol* 69:6787-6796; Sirkka et al. (1996) *Biochem. Biophy. Res. Com.* 220:294-299; Ryan et al. (1996) *J. Virol.* 70:1542-1553; Weitzman et al. (1996) *J. Virol.* 70:2440-2448; Walker et al. (1997) *J. Virol.* 71:2722-2730; Walker et al. (1997) *J. Virol.* 71:6996-7004; Davis et al. (1999) *J. Virol.* 73:2084-2093; Urabe et al. (1999) *J. Virol.* 73:2682-2693; Gavin et al. (1999) *J. Virol.* 73:9433-9445; Davis et al. (2000) *J. Virol.* 74:2936-2942; Pei Wu et al. (2000) *J. Virol.* 74:8635-8647; Alessandro Marcello et al. (2000) *J. Virol.* 74:9090-9098). AAV are members of the family Parvoviridae and are assigned to the genus Dependovirus. Members of this genus are small, non-enveloped, icosahedral with linear and single-stranded DNA genomes, and have been isolated from many species ranging from insects to humans.

AAV can either remain latent after integration into host chromatin or replicate following infection. Without co-infection, AAV can enter host cells and preferentially integrate at a specific site on the q arm of chromosome 19 in the human genome.

The AAV genome contains 4975 nucleotides and the coding sequence is flanked by two inverted terminal repeats (ITRs) on either side that are the only sequences in cis required for viral assembly and replication. The ITRs contain palindromic sequences, which form a hairpin secondary structure, containing the viral origins of replication. The ITRs are organized in three segments: the Rep binding site (RBS), the terminal resolution site (TRS), and a spacer region separating the RBS from the TRS.

Regulation of AAV genes is complex and involves positive and negative regulation of viral transcription. For example, the regulatory proteins Rep 78 and Rep 68 interact with viral promoters to establish a feedback loop (Beaton et al. (1989) *J. Virol* 63:4450-4454; Hermonat (1994) *Cancer Lett* 87:129-136). Expression from the p5 and p19 promoters is negatively regulated in trans by these proteins. Rep 78 and 68, which are required for this regulation, bind to inverted terminal repeats (ITRs; Ashktorab et al. (1989) *J. Virol.* 63:3034-3039) in a site- and strand-specific manner, in vivo and in vitro. This binding to ITRs induces a cleavage at the TRS and permits the replication of the hairpin structure, thus, illustrating the Rep helicase and endonuclease activities (Im et al. (1990) *Cell* 61:447-457; and Walker et al. (1997) *J. Virol.* 71:6996-7004), and the role of these non-structural proteins in the initial steps of DNA replication (Hermonat et al. (1984) *J. Virol.* 52:329-339). Rep 52 and 40, the two minor forms of the Rep proteins, do not bind to ITRs and are dispensable for viral DNA replication and site-specific integration (Im et al. (1992) *J. Virol.* 66:1119-112834; Ni et al. (1994) *J. Virol.* 68:1128-1138.

Figure 4:
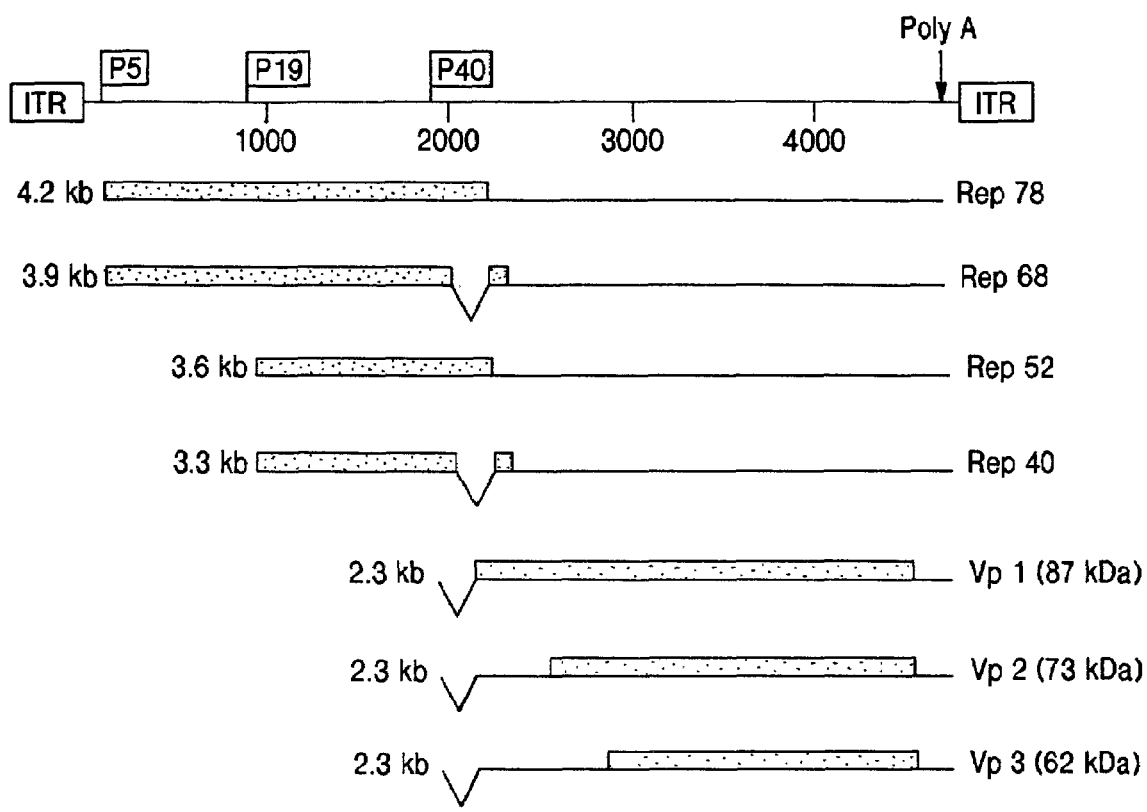
FIG. 4 shows the genetic map of AAV, including the location of promoters, and transcripts; amino acid 1 of the Rep 78 gene is at nucleotide 321 in the AAV-2 genome.

The genome (see, FIG. 4) is organized into two open reading frames (ORFs, designated left and right) that encode structural capsid proteins (Cap) and non-structural proteins (Rep). There are three promoters: p5 (from nucleotides 255 to 261: TATTTAA), p19 (from nucleotide 843 to 849: TATTTAA) and p40 (from nucleotides 1822 to 1827: ATATAA). The right-side ORF (see FIG. 4) encodes three capsid structural proteins (Vp 1-3). These three proteins, which are encoded by overlapping DNA, result from differential splicing and the use of an unusual initiator codon (Cassinoti et al. (1988) *Virology* 167:176-184). Expression of the capsid genes is regulated by the p40 promoter. Capsid proteins VP1, VP2 and VP3 initiate from the p40 promoter. VP1 uses an alternate splice acceptor at nucleotide 2201; whereas VP2 and VP3 are derived from the same transcription unit, but VP2 use an ACG triplet as an initiation codon upstream from the start of VP3. On the left side of the genome, two promoters p5 and p19 direct expression of four regulatory proteins. The left flanking sequence also uses a differential splicing mechanism (Mendelson et al. (1986) *J. Virol* 60:823-832) to encode the Rep proteins, designated Rep 78, 68, 52 and 40 on the basis molecular weight. Rep 78 and 68 are translated from a transcript produced from the p5 promoter and are produced from the unspliced and spliced form, respectively, of the transcript. Rep 52 and 40 are the translation products of unspliced and spliced transcripts from the p19 promoter.

The rep protein is a adeno-associated virus protein involved in a number of biological processes necessary to AAV replication. The production of the rRep proteins enables viral DNA to replicate, encapsulate and integrate (McCarty et al. (1992) *J. Virol* 66:4050-4057; Horer et al. (1995) *J. Virol* 69:5485-5496, Berns et al. (1996) Biology of Adeno-associated virus, in Adeno-associated virus (AAV) Vectors in Gene Therapy, K. I. Berns and C. Giraud, Springer (1996); and Chiorini et al. (1996) The Roles of AAV Rep Proteins in gene Expression and Targeted Integration, from Adeno-associated virus (AAV) Vectors in Gene Therapy, K. I. Berns and C. Giraud, Springer (1996)). A rep protein with improved activity could lead to increased amounts of virus progeny thus allowing higher productivity of rAAV vectors.

AAV and rAAV have many applications, including use as a gene transfer vector, for introducing heterologous nucleic acid into cells and for genetic therapy. Advances in the production of high-titer rAAV stocks to the transition to human clinical trials have been made, but improvement of rAAV production will be complemented with special attention to clinical applications of rAAV vectors as a successful gene therapy approach. Productivity of rAAV (i.e. the amount of vector particles that can be obtained per unitary manufacturing peration) is one of the rate limiting steps in the further development of rAAV as a gene therapy vector. Methods for high throughput production and screening of rAAV have been developed (see, e.g., Drittanti et al. (2000) *Gene Therapy* 7:924-929). Briefly, as with the other steps in methods provided herein, the plasmid preparation, transfection, virus productivity and titer and biological activity assessment are intended to be performed in an automatable high throughput format, such as in a 96 well or loci formats (or other number of wells or multiples of 96, such as 384, 1536 . . . 9600, 9984 . . . well or loci formats).

Since the Rep protein is involved in replication it can serve as a target for increasing viral production. Since it has a variety of functions and its role in replication is complex, it has heretofore been difficult to identify mutations that result in increase viral production. The methods herein, which rely on in vivo screening methods, permit optimization of its activities as assessed by increases in viral production. Provided herein are Rep proteins and viruses and viral vectors containing the mutated Rep proteins that provide such increase. The amino acid positions on the rep proteins that are relevant for rep proteins activities in terms of AAV or rAAV virus production are provided. Those amino acid positions are such that a change in the amino acid leads to a change in protein activity either to lower activity or increase activity. As shown herein, the alanine or amino acid scan revealed the amino acid positions important for such activity (i.e. hits). Subsequent mutations produced by systematically replacing the amino acids at the hit positions with the remaining 18 amino acids produced so-called "leads" that have amino acid changes and result in higher virus production. In this particular example, the method used included the following specific steps.

Amino Acid Scan

Figure 3A:
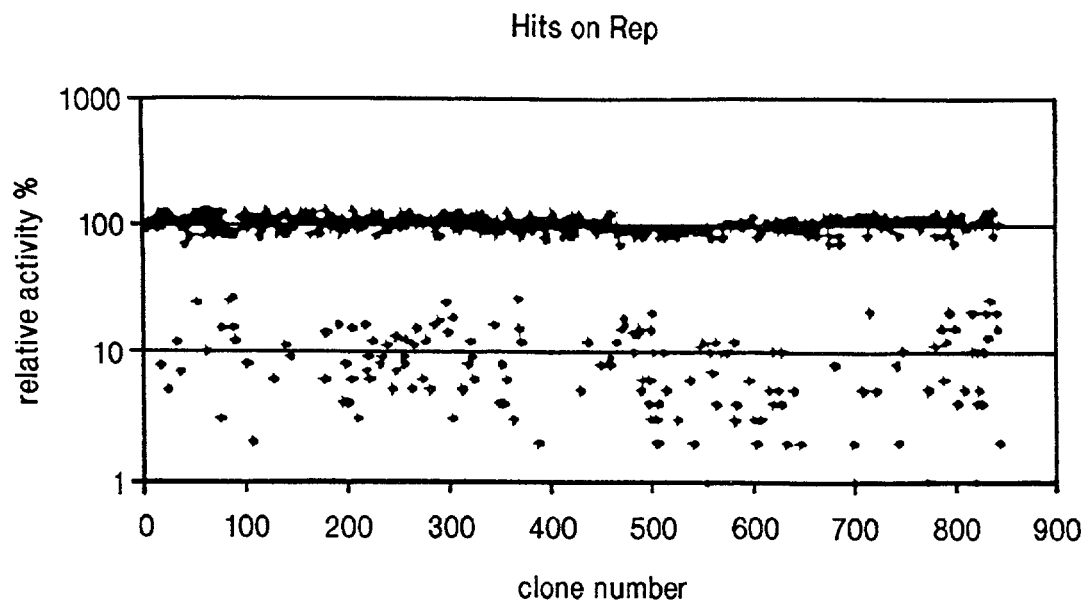
FIGS. 3A and 3B depict "HITS" and "LEADS" respectively for identification of AAV rep mutants "evolved" for increased activity.

In order to first identify those amino acid (aa) positions on the rep protein that are involved in rep protein activity, an Ala-scan was performed on the rep sequence. For this, each aa in the rep protein sequence was individually changed to Alanine. Each resulting mutant rep protein was then expressed and the amount of virus it could produced measured as indicated below. The relative activity of each individual mutant compared to the native protein is indicated in FIG. 3A. HITS are those mutants that produce a decrease in the activity of the protein (in the example: all the mutants with activities below about 20% of the native activity).

In a second experimental round, which included a new set of mutations and phenotypic analysis, each amino acid position hit by the Ala-scan step, was mutated by amino acid replacement of the native amino acid by the remaining 18 amino acids, using site-directed mutagenesis.

In both rounds, each mutant was individually designed, generated and processed separately, and optionally in parallel with the other mutants. Neither combinatorial generation of mutants nor mixtures thereof were used in any step of the method.

Figure 3B:
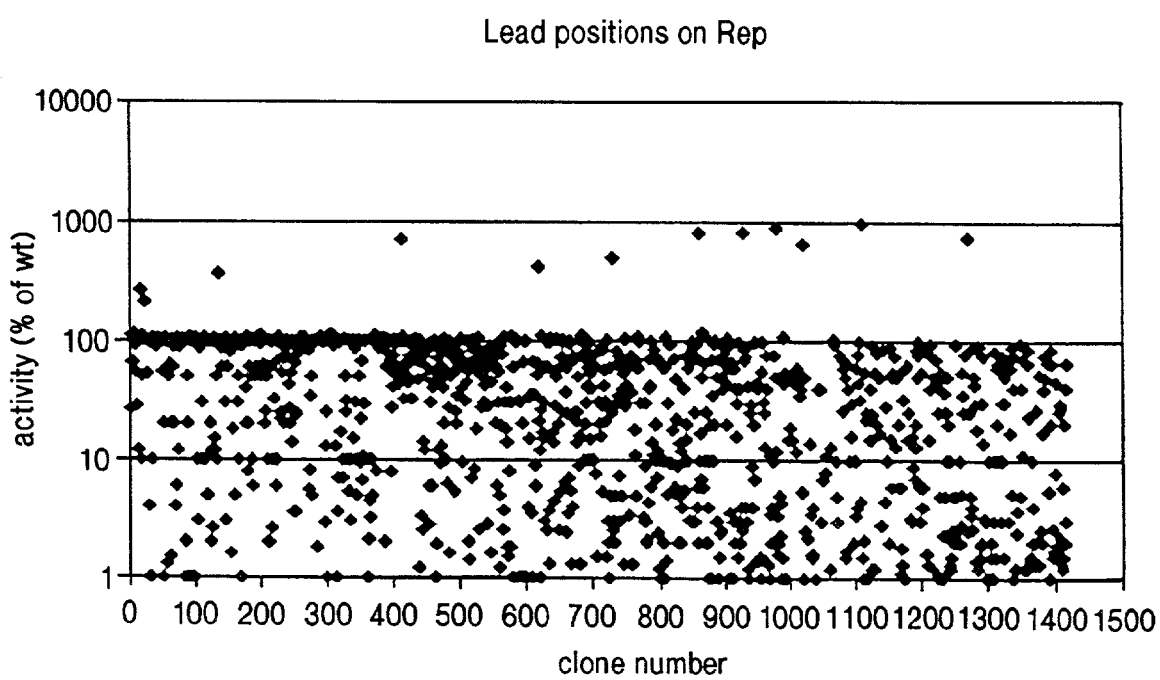

A plasmid library was thus generated in which each plasmid contained a different mutant bearing a different amino acid at a different hit position. Again, each resulting mutant rep protein was then expressed and the amount of virus it could produce measured as indicated below. The relative activity of each individual mutant compared to the native protein is indicated in FIG. 3B. Leads are those mutants that lead to an increase in the activity of the protein (in the example: the ten mutants with activities higher, typically between 2 to 10 times or more, generally 6-10 time, than the native activity).

Expression of the Genetic Variants and Phenotypic Characterization

The rep protein acts as an intracellular protein through complex interaction with a molecular network composed by cellular proteins, DNA, AAV proteins and adenoviral proteins (note: some adenovirus proteins have to be present for the rep protein to work). The final outcome of the rep protein activity is the virus offspring composed by infectious rAAV particles. It can be expected that the activity of rep mutants would affect the titer of the rAAV virus coming out of the cells.

As the phenotypic characterization of the rep variants can only be accomplished by assaying its activity from inside mammalian cells, a mammalian cell-based expression system as well as a mammalian cell-based assay was used. The individual rep protein variants were expressed in human 293 HEK cells, by transfection of the individual plasmids constituting the diverse plasmid library. All necessary functions were provided as follows:

(a) the cellular proteins present in the permissive specific 293 HEK cells;

(b) the AAV necessary proteins and DNA were provided by co-transfection of the AAV cap gene as well as a rAAV plasmid vector providing the necessary signaling and substrate ITRs sequences;

(c) the adenovirus (AV) proteins were provided by co-transfection with a plasmid expressing all the AV helper functions.

A library of recombinant viruses with mutant rep encoding genes was generated. Each recombinant, upon introduction into a mammalian cell and expression resulted in production of rAAV infectious particles. The number of infectious particles produced by each recombinant was determined in order to assess the activity of the rep variant that had generated that amount of infectious particles.

The number of infectious particles produced was determined in a cell-based assay in which the activity of a reporter gene, in the exemplified embodiment, the bacterial lacZ gene, or virus replication (Real time PCR) was performed to quantitatively assess the number of viruses. The limiting dilution (titer) for each virus preparation (each coming from a different rep variant) was determined by serial dilution of the viruses produced, followed by infection of appropriate cells (293 HEK or HeLa rep/cap 32 cells) with each dilution for each virus and then by measurement of the activity of the reporter gene for each dilution of each virus. Hill plots (NAUTSCAN™) as described herein (published as International PCT application No. WO 01/44809 based on PCT no PCT/FR00/03503, December, 2000; see EXAMPLES) or a second order polynomial function (Drittanti et al. (2000) Gene Ther. 7: 924-929) was used to analyze the readout data and to calculate the virus titers. Briefly, the titer was calculated from the second order polynomial function by non-linear regression fitting of the experimental data. The point where the polynomial curve reaches its minimum is considered to be the titer of the rAAV preparation. A computer program for calculation of titers has been developed (see Drittanti et al. (2000) Gene Ther. 7: 924-929) to assess the minima.

The TREE method described herein can be used to analyze the readout data and to calculate the virus titers. The results are shown in the EXAMPLE below.

Comparison Between Results of Full-Length Hit Position Analysis Reporter Here and the Literature The experiments identified a number of heretofore unknown mutation loci, which include the hits at positions: 4, 20, 22, 28, 32, 38, 39, 54, 59, 124, 125, 127, 132, 140, 161, 163, 193, 196, 197, 221, 228, 231, 234, 258, 260, 263, 264, 334, 335, 341, 342, 347, 350, 354, 363, 364, 367, 370, 376, 381, 389, 407, 411, 414, 420, 421, 422, 428, 429, 438, 440, 451, 460, 462, 484, 488, 495, 497, 498, 499, 503, 511, 512, 516, 517 and 518 with reference to the amino acids in Rep 78 and Rep 68. Rep 78 is encoded by nucleotides 321-2,186; Rep 68 is encoded by nucleotides 321-1906 and 2228-2252; Rep 52 is encoded by nucleotides 993-2186, and Rep 40 is encoded by amino acids 993-1906 and 2228-2252 of wild-type AAV.

Also among these are mutations that may have multiple effects. Since the Rep coding region is quite complex, some of the mutations may have several effects. Amino acids 542, 598, 600 and 601, which are in the Rep 68 and 40 intron region, are also in the coding region of Rep 78 and 52. Codon 630 is in the coding region of Rep 68 and 40 and non coding region of Rep 78 and 52.

Mutations at 10, 86, 101, 334 and 519 have been previously identified, and mutations, at loci 64, 74, 88, 175, 237, 250 and 429, but with different amino acid substitutions, have been previously reported. In all instances, however, the known mutations reportedly decrease the activity of Rep proteins. Among mutations described herein, are mutations that result in increases in the activity the Rep function as assessed by detecting increased AAV production.

Lead Identification

Based on the results obtained from the assays described herein (i.e. titer of virus produced by each rep variant), each individual rep variant was assigned a specific activity. Those variant proteins displaying the highest titers were selected as leads and are used to produce rAAV.

In further steps, rAAV and Rep proteins that contain a plurality of mutations based on the hits (see Table in the EXAMPLES, listing the hits and lead sites), are produced to produce rAAV and Rep proteins that have activity that is further optimized. Examples of such proteins and AAV containing such proteins are described in the EXAMPLES.

The rAAV rep mutants are used as expression vectors, which, for example, can be used transiently for the production of recombinant AAV stocks. Alternatively, the recombinant plasmids may be used to generate stable packaging cell lines. To create a stable producer cell line, the recombinant vectors expressing the AAV with mutant rep genes, for example, are cotransfected into host cells with a plasmid expressing the neomycin phosphotransferase gene (neor) by transfection methods well known to those skilled in the art, followed by selection for G418 resistance.

Also among the uses of rAAV, particularly the high titer stocks produced herein, is gene therapy for the purpose of transferring genetic information into appropriate host cells for the management and correction of human diseases including inherited and acquired disorders such as cancer and AIDS. The rAAV can be administered to a patient at therapeutically effective doses. A therapeutically effective dose refers to that amount of the compound sufficient to result in amelioration of symptoms of disease.

Gene Therapy

Toxicity and therapeutic efficacy of the rAAV can be determined by standard pharmaceutical procedures in cell cultures or experimental animals, e.g., for determining the $LDS_{50}$ (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. Doses that exhibit large therapeutic indices are preferred. Doses that exhibit toxic side effects may be used, however care should be taken to design a delivery system that targets rAAV to the site of treatment in order to minimize damage to untreated cells and reduce side effects.

The data obtained from cell culture assays and animal studies can be used in formulating a range of dosage for use in humans. The dosage of such rAAV lies preferably within a range of circulating concentrations that include the $ED_{50}$ with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection or a half-maximal inhibition) as determined in cell culture. Such information can be used to more accurately determine useful doses in humans. Levels in plasma may be measured, for example, by high performance liquid chromatography.

The following examples are included for illustrative purposes only and are not intended to limit the scope of the invention. The specific methods exemplified can be practiced with other species. The examples are intended to exemplify generic processes.

EXAMPLE 1

Titering or Assessment of Concentration by a Method Designated Real Time Vector Titering (RTVT™)

This Example is based on the method described in International PCT application No. PCT/FR01/01366, based on French application no 0005852, filed May 9, 2000, and published as International PCT application No. WO 01/186291. This method assesses the titer or concentration of a biological agent (virus, gene transfer vector) in a sample, by measurement of the kinetics of change of a reporter parameter following the exposure of cells to the biological agent.

As noted above, reporter parameters may include, but are not limited to,: gene/transgene expression related to the gene/transgene products, such as enzymatic activity, fluorescence, luminescence, antigen activity, binding to receptors or antibodies, and regulation of gene expression), differential gene expression, viral/vector progeny productivity, toxicity, cytotoxicity, cell proliferation and/or differentiation activity, antiviral activity, morphogenetic activity, pathogenetic activity, therapeutic activity, tumor suppressor activity, oncogenetic activity, pharmacological activity.

Serial Dilution Methods

The assessment of the concentration or titer of biological agents using current approaches needs serial dilutions of the agent. Serial dilutions of the agent are applied to a cell-based reporter system, that elicits an output signal in response to the exposure to the agent. The intensity of the signal is a function of the concentration of the agent. The titer or concentration of the agent is determined as the highest dilution that still elicits a measurable response in the output. The higher the number of dilutions tested, the higher the accuracy of the value obtained for the titer.

This approach requires a set of serial dilutions for every biological agent whose titer needs to be determined. Thus, the application of this approach to the simultaneous titration of a large number of different biological agents is limited by the number of experimental points needed (example: for 30 biological samples: 20 serial dilutions×30 biological agents: 600 experimental points).

The Approach in International PCT Application No. PCT/FR01/01366 Published as International PCT Application No. WO 01/186291

The intensity of the output signal (after exposure of reporter cells to the biological agent) is not only dependent on the concentration of the agent but also on the time after exposure. As time increases, the intensity of the signal increases. The kinetics of change of the intensity over time depends upon the concentration of the agent. Thus, lower concentrations of the agent will require longer times for the intensity to reach a given value that would be reached in shorter times after exposure to higher concentrations of the same agent.

This approach (designated Real Time Virus Titering (RTVT™) uses the following: a reference plot representing the relationship between the concentration of the agent and the time necessary for the intensity to reach a given threshold value is obtained using a reference preparation of biological agent, whose concentration or titer is known. This plot is then used to obtain the concentration of the biological agent under study by entering the time that a dilution of that agent needed for the intensity to reach the threshold value.

Using this approach, there is no need for serial dilutions of the biological agent(s) under study. Once the reference plot (tβ vs c) is obtained, it can be used for the determination of the concentration or titer of any number of biological agents. Only one dilution of the biological agent under study is necessary to obtain the corresponding value of tβ that is then used to obtain the concentration or titer using the reference plot.

Thus, the application of this approach to the simultaneous titration of large numbers of different biological agents is facilitated by the fact that only one dilution of each sample is needed (example: for 30 biological samples: 1 dilution×30 biological agents: 30 experimental points (compared to 600 needed with the current approach). This approach is specially suited for the high throughput assessment of concentration or titer of large numbers of biological agents.

The System

The system includes the following elements:

a preparation of the biological agent (virus, gene transfer vector, protein, . . . ) whose concentration or titer is unknown and has to be determined.

a reporter system including culture of a cell line (or a mixture of cell lines) that reacts to the exposure to the biological agent by displaying a specific output signal.

a master preparation of a reference biological agent, of known concentration or titer, that is able to generate the output signal when the reporter cells are exposed to it.

Practice of the Method

When the reporter cells are exposed to either the biological agent under study or the reference biological agent, an output signal is generated, that can be measured.

The intensity of the output signal is called i; the concentration of the biological agent used is called c, the time of exposure of the cells to the biological agent is called t. The intensity of the output signal (i) is a function of c and t:

i increases as the concentration (c) of the biological agent applied to the cells increases;

i increases as the time of exposure of the cells to the biological agent (t) increases.

If the time t after exposure of the cells to the biological agent is kept constant, then, i will change as a direct function of c.

If the concentration c of the biological agent is kept constant, then, i will be a direct function of t.

$\beta$ is defined here as a threshold value of the intensity of the output signal, arbitrarily defined for every system under study.

t$\beta$ is defined here as the time necessary to reach the threshold $\beta$.

Use of $\beta$ and t$\beta$ to Determine the Concentration or Titer of a Biological Agent The reporter cells are exposed to serial dilutions of a reference biological agent, whose concentration (or titer) is previously known. The intensity of the output signal (i) is measured at several time points (t) for every concentration (serial dilutions) c of the reference biological agent.

i is plotted vs t, and that, for every concentration c used of the reference biological agent.

Using the plots obtained above, and for every concentration c of the reference biological agent, the time (t$\beta$) necessary for the intensity of the output signal to reach a threshold value $\beta$ is obtained.

With the data obtained above, t$\beta$ is plotted vs c.

This plot represents the time necessary for the intensity of the output signal to reach the threshold value $\beta$ as a function of the concentration of the biological agent used. This is a standard plot and will be used to determine the unknown concentration of the biological agent under study by measuring the time that a given dilution of it needs to give an output signal whose intensity equals the threshold $\beta$.

The reporter cells are exposed to a dilution of the biological agent under study (whose concentration or titer is to be determined). The intensity of the output signal (i) is measured over time until it reaches the threshold value $\beta$. The time necessary for i to reach the value $\beta$ is recorded as t$\beta$.

The t$\beta$ value recorded above is entered into the standard plot obtained above and the corresponding c value is obtained.

This c value represents the concentration or titer of the biological agent under study.

Example of the Real Time Virus Titering RTVT™ Titering Method

Rat-2 cells were infected with serial dilutions of a reference preparation of a retroviral vector carrying the green fluorescent protein (GFP) gene (vector pSI-EGFPI see, Ropp et al. (1995) *Cytometry* 21:309-317). At increasing times after infection, the level of expression of the transgene was determined (as the level of fluorescence due to the GFP gene) as the output signal.

TABLE 3 represents the values obtained:

| Concentration (1 = $10^6$ particles/ml) | Time after infection (hrs) | Output signal fluorescence |
|---|---|---|
| 0.1 | 16 | 20.4 |
|  | 24 | 30.1 |
|  | 40 | 95.1 |
|  | 48 | 138.7 |
|  | 64 | 157.3 |
| 0.25 | 16 | 26.8 |
|  | 24 | 48.5 |
|  | 40 | 173.3 |
|  | 48 | 228.2 |
|  | 64 | 191.7 |
| 0.5 | 16 | 38.1 |
|  | 24 | 72 |
|  | 40 | 198.7 |
|  | 48 | 296.2 |
|  | 64 | 203.7 |

The threshold value of $\beta=100$ was arbitrarily selected for this example. The time (t$\beta$) necessary for the output signal to reach the threshold $\beta$, for every concentration is shown in table 4.

TABLE 4

| Concentration (1 = $10^6$ particles/ml) | t$\beta$ (hrs) |
|---|---|
| 0.1 | 42 |
| 0.25 | 31 |

A plot of t$\beta$ versus concentration for the reference virus shows that the concentration and t$\beta$ exhibit a clearly defined relationship, that allows for the calculation of the concentration (c) of a sample, if the corresponding t$\beta$ of that sample is known.

EXAMPLE 2

Tagged Replication and Expression Enhancement (TREE) for Titering

As discussed above, TREE is a method for titering and standardization of preparations of viruses, vectors, antibodies, libraries, proteins, genes and any other moiety that is detectable based upon a output signal, such as fluorescence. The TREE method is an improvement of the Real Time Virus Titering (RTVT) method (see, International PCT application No. PCT/FR01/01366 published as International PCT application No. WO 01/186291). It is performed with a reporter moiety, such as a reporter virus (with a known titer) and the test sample (with unknown titer). The reporter, such as a reporter virus, has a readily detectable output signal that can be measured as a function of time. The effect of the moiety, such as a virus, of unknown titer is assessed. The moiety whose titer is assessed either increases or decreases the output signal as a function of time. This change in signal is used to assess the amount or concentration of the moiety of unknown concentration, and hence its titer.

The method is exemplified herein using an AAV system for the determination of the titer of an AAV vector and an AAV-reporter vector as a competitor and wild type Adenovirus as helper virus. One of skill in the art readily can adapt the method to other systems, including other viruses, and other moieties for which a reporter system can be developed. Other such moieties include, but are not limited to, viral vectors, plasmids, libraries, proteins, antibodies, vaccines, genes, and nucleic acid molecules.

Materials and Methods

1. Cells and Viruses

HeLa rep-cap32 cells, a HeLa derived cell line (kindly provided by P. Moullier, Laboratoire de Thérapie Génique, CHU, Nantes; see, Salvetti et al. (1998) *Hum Gene Ther* 20:695-706; Chadeuf et al. (2000) *J Gene Med* 2:260-268) was grown in DMEM with 10% fetal calf serum. These cells were plated 24 h before infection at a density of $1\times10^4$ cells in single well of 96-well plates. rAAV-LacZ ($10^{10}$ ip/ml), rAAV-GFP ($10^9$ ip/ml) vectors and Human Adenovirus type 5 (Ad5) ($10^{11}$ pfu/ml) were from CHU, Nantes.

Hela rep-cap32 cells had been produced by cotransfecting plasmid pspRC, which harbors the AAV rep-cap genome with the ITRs deleted (bp 190 to 4484 of wild-type AAV), with plasmid PGK-Neo, conferring resistance to G418 on Hela cells (see, Chadeuf et al. (2000) *J. Gene Med.* 2:260-268 and Salvetti et al. (1998(*Hum Gene Ther.* 9:695-706). Hela rep-cap 32 cells are a packaging line that harbor one copy of the genome with the ITRs deleted (see, also Tessier et al. (2001) *J. Virol.* 75:375-383).

Plasmid pspRC contains the AAV genome (positions 190-4,484 bp) with the ITRs deleted and was obtained by excising the rep-cap fragment (XbaI fragment) from the well-known vector psub201 (Samulski et al. (1987) *J Virol* 61:3096-3101; also called pSSV9) by XbaI digestion and inserting it into the XbaI site of plasmid pSP72 (Promega). Plasmid psub201 (see, e.g., U.S. Pat. No. 5,753,500) is a modified full-length AAV type 2 genomic clone contains all of the AAV type 2 wild-type coding regions and cis acting terminal repeats.

2. Infection and Measurement

Four serial dilutions of a rAAV-LacZ (0.01, 0.0075, 0.005 and 0.0025 µl, see Table 2 below, designated samples 1-4, respectively) were made and used for co-infection of HeLa rep-cap32 cells together with 8 different Ad5 multiplicity of infection (MOI; from 0.1 to 100/cell) and with $10^{-3}$ ml ($10^6$ infectious particles (ip)) or $10^{-4}$ ml ($10^5$ ip) rAAV-GFP viral vector. All the samples were done in triplicate. After infection, the plates were read at different times, from 34.5 h to 80 h (every 30 minutes).

rAAV-GFP is an SSV9-derived vector; SSV9 is a clone containing the entire adeno-associated virus (AAV) genome inserted into the PvuII site of plasmid pEMBL (see, Du et al. (1996) *Gene Ther* 3:254-261). The rAAV-GFP and rAAV-LacZ plasmids are SSV9 with a GFP or LacZ gene under control of the cytomegalovirus (CMV) immediate-early promoter. All the samples were done in triplicate.

3. Process

Figure 2A:
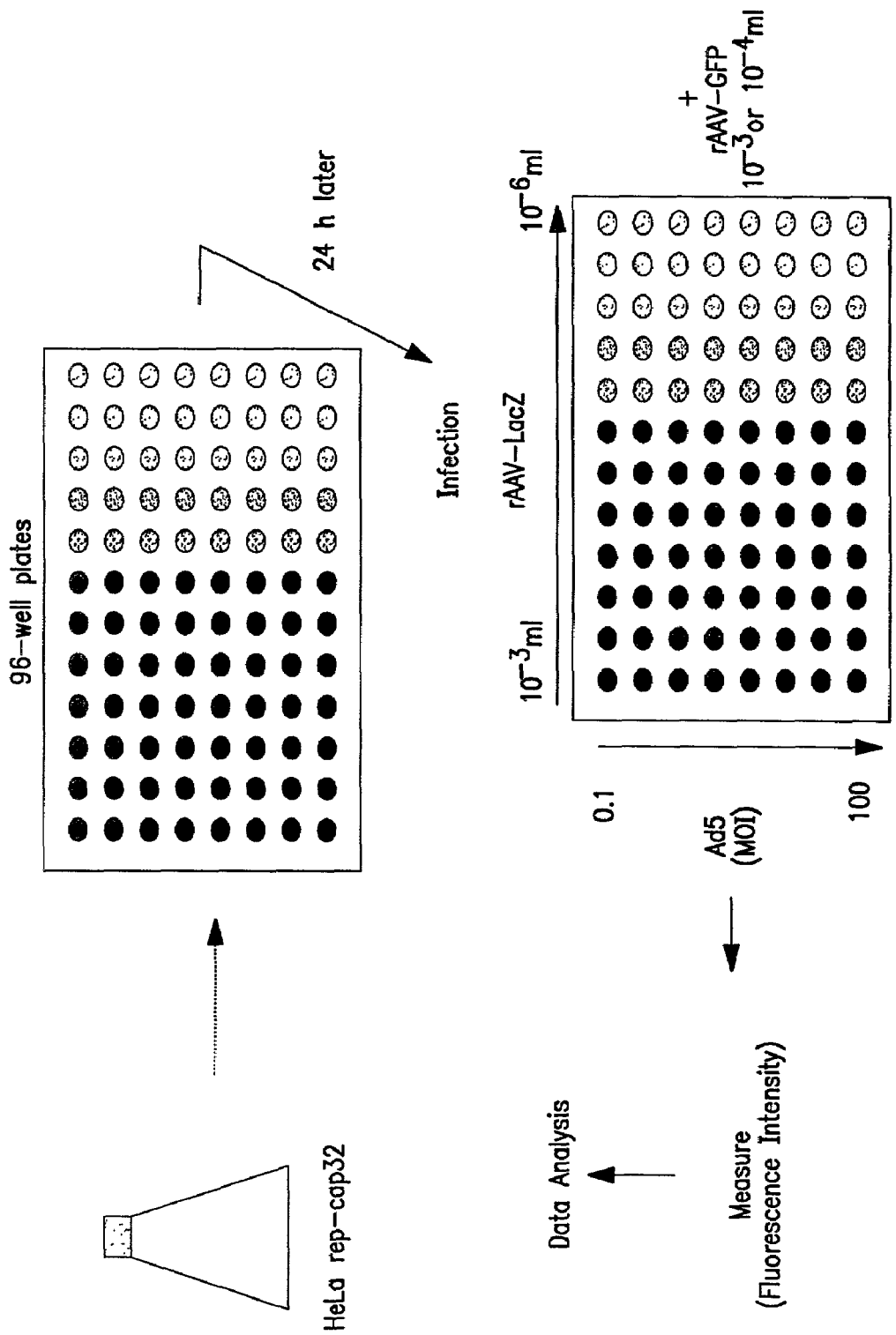
FIG. 2A depicts an exemplary titering process (in this instance the TREE™ for titering AAV) in a 96 well format.
Figure 2B:
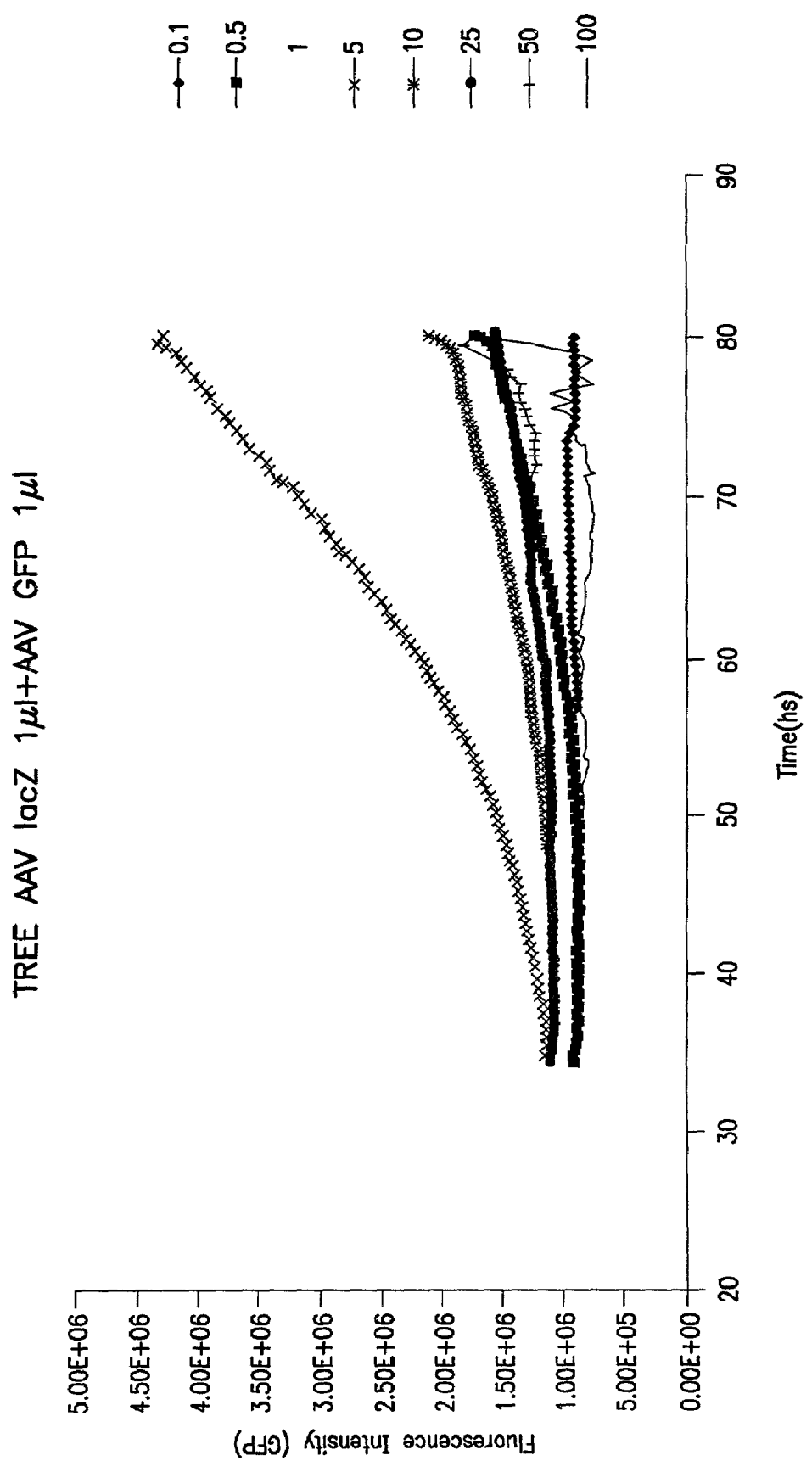
FIG. 2B shows the results and analysis of a titering process performed using the TREE™ procedure.

FIG. 2 shows the overall procedure in 96 well format. Cells were plated 24 h before infection. Co-infection of rAAV-GFP with serial dilutions of rAAV-LacZ together with Ad5 (different MOI), were done. Then the plates were read at different times using the Analyst AD&HT micro plate-reader (LJL BioSystems).

4. Analysis

For this kinetic technique, Fluorescence Intensity (FI) of the infected cells is measured as a function of the time. Serial dilutions of the AAV-competitor vector AAV-lacZ vector, which decreases the fluorescence signal, are performed. For this example, fluorescence was measured for AAV-GFP with $10^6$ ip and $10^5$ ip and then $10^6$ ip of the AAV-GFP reporter virus in the serial dilutions of the competitor virus, AAV-lacZ vector in a 96-well format (samples 1-4, see Table below). Measurements were taken of each well and curves of FI (of the GFP) versus time (hrs) were obtained (see FIG. 2B).

An arbitrary one value for FI (see FIG. 2B, $6 \times 10^6$ FI units), typically, though not necessarily, near the greatest separation among the curves so that the numbers are readily discernable, was selected. The point at which each of the curves intersect this value is beta time (t$\beta$) for that combination of amounts of reporter plus dilution of the virus of unknown titer. t$\beta$, taken from the FI vs. Time (hrs) curves, for each sample containing a dilution of the unknown plus $10^6$ ip of the reporter virus is set forth in column 3 of Table 2 below.

Figure 2C:
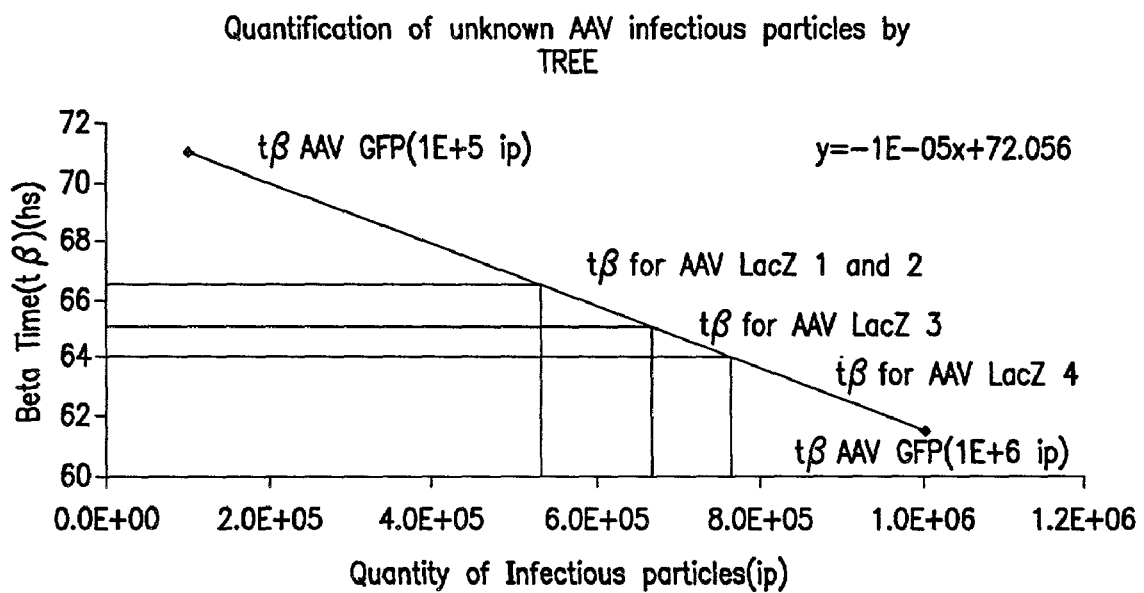
FIG. 2C shows an exemplary calibration curve for the calculation of the titer using the TREE™ method.

To determine the titer of the test virus, the t$\beta$ for the AAV GFP (reporter virus) is plotted versus quantity of ip (i.e a straight line between the t$\beta$ for the $10^6$ ip and the $10^5$ ip) (FIG. 2C). For any t$\beta$ of the unknown virus, the quantity of ip can be determined from this curve. The beta time (t$\beta$) of each sample (in this case for the different dilutions of rAAV LacZ mixed with $10^6$ infectious particles of rAAV-GFP) is determined, and then the residual number of infectious particles of rAAV-GFP for each sample. The difference between $10^6$ ip of rAAV-GFP put in each sample and the number of ip detected by fluorescence in the same well is the actual quantity of rAAV-GFP competed (consumed) by the unknown rAAV (in this case rAAV-LacZ). This number is determined for each dilution. The quantity rAAV-GFP consumed is the same quantity of unknown rAAV in the sample. This quantity is present in one volume of unknown rAAV, which in this example is 1 ml. Based upon this, the infectious titer of the unknown rAAV is determined. The results are shown in Table 2.

TABLE 2

AAV LacZ titration by TREE titration

| Sample | volume (μl) | t$\beta$ (hrs) | Residual AAV-GFP | Consumed AAV-GFP | AAV LacZ Concentration (i.p./$10^{-2}$ μl) |
|---|---|---|---|---|---|
| 1 | $10.0 \times 10^{-3}$ | 66.5 | $5.56 \times 10^5$ | $4.44 \times 10^5$ | $4.44 \times 10^5$ |
| 2 | $7.5 \times 10^{-3}$ | 66.5 | $5.56 \times 10^5$ | $4.44 \times 10^5$ | $5.93 \times 10^5$ |
| 3 | $5.0 \times 10^{-3}$ | 65 | $7.06 \times 10^5$ | $2.94 \times 10^5$ | $5.88 \times 10^5$ |
| 4 | $2.5 \times 10^{-3}$ | 64 | $8.06 \times 10^5$ | $1.94 \times 10^5$ | $7.76 \times 10^5$ |

The average titer using this method was $6.01 \times 10^{10}$ ip/ml ($6.01 \times 10^7$ ip/μl = $6.01 \times 10^5$ ip/0.01 μl). The standard deviation was $1.37 \times 10^{10}$ ip/ml with an error of ±23%.

EXAMPLE 3

Hill Analysis of the Screening Assay Output

It is important to have reliable methods for screening and/or evaluating the performance of a set of biological agents, such as a library of viral or non-viral recombinant vectors, vaccines, recombinant proteins and antibodies, in a complex biological system, such as living target cells When developing such agents, for example gene therapy vectors and other agents for therapeutic use, it is necessary to be able to evaluate and compare performance among candidates.

The progress of gene transfer into gene therapy depends upon the capacity to develop gene transfer vectors into therapeutic drugs. Clinically relevant vectors need to be efficient and safe, in reaching and infecting target cells and in ensuring a persistent level of expression of the therapeutic gene with a minimum of adverse effects. The availability of standardized quantitative methods, suitable for an accurate and objective assessment of titer, performance and safety, is necessary for the pharmaceutical development of gene vectors as drugs.

Any method for assessment is contemplated herein as long as it is adapted for use in a high throughput format. Of particular interest is the Hill equation based method of International PCT application No. WO 01/44809 (International PCT application No. PCT/FR00/03503, based on French application FR 9915884).

Two widely used parameters that provide quantitative information about the potential performance of a gene transfer vector preparation are the titer of physical particles and the titer of infectious particles. Vector preparations with high titer of infectious particles and low physical particles/infectious particles ratio are considered to be of higher quality.

The titer in physical particles(pp) (see, e.g., Mittereder et al. (1996) *J. Virol.* 70:7498-7509; Atkinson et al. (1998) *Nucl. Acids Res.* 26:2821-2823; Kechli et al. (1998) *Hum. Gene Ther.* 9:587-590; and Nelson et al. (1998) *Hum. Gene Ther.* 9:2401-2405), which represents the total number of vector particles, is usually evaluated from the vector content by detecting the nucleic acid contents (nucleic acids hybridization and $OD_{260}$ respectively for AAV and AdV), detecting viral protein content (for example, reverse transcriptase (RT) activity and p24 content for MLV and HIV, respectively).

Among the physical particles (pp), there are particles potentially active in performing transduction (ip, infectious particles), as well as particles that are inactive (nip, non-infectious particles) (Ruffing et al. (1994) *J. Gen. Virol.* 75:3385-3392; Kechli et al. (1998) *Hum. Gene Ther.* 9:587-590.). The pp and the ip/nip ratio, are features of the packaging system, the manufacturing process and the vector itself.

The infectious particles (ip) (infectious units, transducing units, etc.) are evidenced by the changes observed in the infected cells (vector DNA replication, provirus integration, cell lysis, transgene expression and other observable parameters). Infectious particles (ip) measures the number of particles effective in performing a process whose output is being measured; not all particles participate or are capable of participating in all processes.

The precise assessment of ip is not straightforward. Existing methods are mainly based on serial dilution experiments followed by either linear extrapolation or asymptote approximates. The titer of infectious particles (ip: infectious unity, transduction unity) (see, e.g., Mittereder et al. (1996) *J. Virol.* 70:7498-7509; Weitzman et al. (1996) *J. Virol.* 70:1845-1854; Salvetti et al. (1998) *Hum. Gene Ther.* 9:695-706) is evaluated by the studying observed changes in infected cells, such as viral replication, provirus integration, cellular lysis and transgene expression, using methods based on serial dilutions, followed either by a linear extrapolation or an asymptotic approximation. Thus, ip measures the number of active particles in the measured process; it includes physical particle (pp) and inactive particles (nip or non-infectious particles).

In order to resolve the problem of the titer determination and the comparison of different recombinant viruses used in gene therapy, the variation of the particles/infectious power ratio has been used (see, e.g., Atkinson et al. (1998) *Nucl. Acids Res.* 26:2821-2823; and International PCT application No. WO 99/11764, which describe a method that uses step of amplification viral genetic material in a host cellular line, preparation of vectors of unknown titer obtained by serial dilution and an internal check of known titer). In particular, the method uses cells infected with a viral preparation in the different wells of a microtiter plate, viral genome replication in the host cells, nucleic acid hybridization and determination of the relative amount of replicated viral nucleic acid in each well.

All of these methods measure the physical particles (pp) titer and/or measure infectious particles (ip) titer in order to evaluate a gene transfer vector. A high quality vector preparation is one with an high titer of infectious particles and a low pp/ip ratio. These parameters provide quantitative information on the performance of a gene transfer vector. Because of the inaccuracy of the procedures used for assessing pp and especially ip, these parameters are not informative enough to precisely define the features of a gene therapy vector nor those of a particular preparation thereof. The actual procedures used for pp and ip evaluation change with the vector type, are not very reproducible nor exact, so these parameters do not contain enough information to allow a very fine definition of vector characteristics and performances.

Hill Equation-Based Analyses

In this method complex biological processes, including those involving the response of cells (in vitro and in vivo) to biological agents, such as, for example, cells, viruses, vaccines, viral and non-viral gene vectors, antibodies, antigens, proteins in general and plasmids, are characterized using the formal analysis first introduced by Hill (see, Hill (1910) *J. Physiol.* 40:4P; Hill (1913) *I. Biochem. J.* 7:471-480). International PCT application No. WO 01/44809 (based on PCT/FR00/03503, priority claimed to French application FR 9915884) describes the use of the Hill equation (see, Hill (1910) *J. Physiol.* 40:4P; Hill (1913) *I. Biochem. J.* 7:471-480; see, International PCT application No. PCT/FR00/03503) for analysis and characterization of the biological and/or pharmacological activity of biological agents (viruses, vectors or cells) on biological assay systems in vitro (cell-based) or in vivo.

A number of useful parameters, derived from the Hill equation, are scored and used to quantify relevant features of the biological agent, of the cells, as well as of the biological process or reaction involved.

In particular, methods for calculation and analysis of the parameters of biological and pharmacological activity of native, attenuated, modified or recombinant viruses, vaccines, recombinant viral and non-viral gene transfer vectors, cells, antibodies and protein factors in in vitro (cell-based) or in vivo assays are described. This method is adapted for high throughput processes and is sufficiently accurate to allow a very fine definition of vector characteristics and performances.

International PCT application No. WO 01/44809 provides, a standard process for evaluating the interaction between any biological agent, such as a gene therapy vector, with a complex biological system (living target cells). It provides a screening process for a pool of complex biological agents, in order to select test agents that have a desired property, activity, structure or whatever is being sought.

Different biological agents and assay systems (cells) are compared and ranked out on the basis of their performance, assessed through the Hill parameters. Thus, the accurate analysis and comparison of the biological response of complex assay systems (in vitro and in vivo) to complex biological agents is achieved experimentally. The Hill-based analysis ($\pi$, $\kappa$, $\tau$, $\epsilon$, $\eta$, $\theta$) is used for a variety of purposes, including, but not limited to:

i) validation and optimization of the manufacturing processes used to obtain the biological agents;

ii) development and optimization of the components of the biological agents (proteins, genomes, genetic units);

iii) development and optimization of assays and analytical tests for the characterization of the biological agents.

The method includes the steps of:

(a) preparation, for each biological agent, of a sample scale, obtained by a serial dilution of the biological agent at a R1 concentration, (b) incubation of each sample of the dilution scale obtained in (a), with the target cells at a constant concentration R2, (c) determination of the P product from the reaction R1+R2, at a t moment, in each the sample; and (d) realization of a theoretical curve H from the experimental points R1 and P, for each biological agent by iterative approximation of parameters of the reaction R1+R2→P, at the t moment, in accordance with this equation:

$$P = P_{max}(\pi R1)^r / (\kappa + (\pi R1)^r) \quad r=1, \ldots, n \tag{2}$$

in which:

R1 represents the biological agent concentration in a sample from the scale;

R2 is concentration of target cells (in vitro or in vivo)

P (output) represents the product from the reaction R1+R2 at a t moment;

$P_{max}$ represents the reaction maximal capacity;

$\kappa$ represents, at a constant R2 concentration, the resistance of the biological system for responding to the biological agent (resistance constant R2);

r represents a coefficient that depends on R1 and corresponds to the Hill coefficient; and $\pi$ represents the intrinsic power of the R1 biological agent to induce a response in the biological system (P production at the t moment), and (e) sorting the $\kappa$ and $\pi$ values obtained in (d) for each biological agent and the biological agent, and then ranking according to the values thereof.

Using the parameters ($\pi$, $\kappa$, $\tau$, $\theta$, $\epsilon$, $\eta$) the activity of a biological agent on a complex biological system, as well as its intrinsic features can be fully characterized and compared. In addition, different biological systems either in vitro cell-based) or in vivo can be compared.

Hill Equation

The Hill Equation $$P = \sum_{r=1}^{r=n} P_{max} \cdot R1^r / (K + (R1)^r) \quad R2 \text{ constant} \tag{1}$$

where R1, P, $P_{max}$ and K represent, respectively, the concentration of the reagent R1, the concentration of the product, the maximal capacity of the reaction and the 'affinity' constant between R1 and R2. The Hill's coefficient (r) is a function of R1. The coefficient r is equal to 1 when independent non-interactive binding sites are involved between R1 and R2, such as in reactions that follow kinetics described by Michaelis-Menten; and r varies from 1 to n for systems where the sites involved in the interaction between the R1 and R2 are not independent from each other, and the affinity for R1 at any R2 binding site varies as a function of either i) the degree of occupancy of other R2 sites; ii) the concentration of R1 itself or iii) the concentration of other (positive or negative) regulators.

The Hill equation, thus, is a general formalization that describes the interaction reaction between molecules. It expresses the amount of product formed as a function of the concentration of the reagents and of the affinity constant of the system. Originally developed for the study of the dissociation between haemoglobin and oxygen, the Hill equation covers the formal Michaelis-Menten analysis of enzyme kinetics, the analysis of ligand-receptor binding and of the allosteric protein systems.

According to Hill, for a simple reaction like

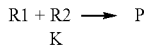

where the affinity between R1 and R2 changes with concentration of each, the Hill equation describes the accumulation of the product P as a function of the concentration of one of the reagents (R1) and of the intrinsic properties (K) of the system.

This equation can be applied to complex biological systems. For example, the response of the cells to infection (P), can be analyzed by applying an Hill-type equation. The amount of cells growing in vitro (R2) are infected with increasing concentrations of recombinant viruses (R1), and (P) is monitored. A Hill equation is iteratively fitted to the experimental data.

For analyses of viral output as exemplified herein,

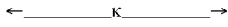

virus+cell→transduced cell→output (viral genome replication), Equation (1) is specifically reformulated as:

$$P = P_{max}(\pi R1)^r / (k + (\pi R1)^r) \quad r = 1, \ldots, n \quad (2)$$

where P, $P_{max}$, R1, $\pi$, r and $\kappa$, as described above, represent, respectively, the output signal (P) (the level of viral gene expression, or the level of virus replication), the maximal output signal (Pmax), the initial concentration (R1) of infectious viral particles (those susceptible to trigger the process leading to P), the potency of the vector ($\pi$; a factor that affects the concentration of the vector (R1) by its specific strength or activity, the Hill's coefficient (r) and the constant of resistance of the reaction or process ($\kappa$).

The Constant of Resistance $\kappa$

The concept of $\kappa$ is analogous to those of dissociation, kinetics, equilibrium or affinity constants concepts for simple chemical and biological reactions. $\kappa$ is a feature of the process (reaction) and of the biological system tested (cell type). $\kappa$ is a key parameter for the characterization of the assay system and the assessment of its performance as a test for the reaction under study.

$\kappa$ measures the internal resistance offered by the process or reaction triggered by the biological agent, to proceed to P. $\kappa$ is specific to a particular process or reaction tested. In addition $\kappa$ is specific to the particular biological system tested. Different cell lines and types will display different $\kappa$ for the same reaction. Moreover, factors affecting the performance of a cell to accomplish the reaction (like contaminants, toxic agents, etc.) affect $\kappa$ in that cell.

Variations in $\kappa$ affect equation (2) by shifting the curve to the right or to the left, according to whether the value of $\kappa$ increases or decreases, respectively. All curves differing only in $\kappa$ are parallel each other. $\kappa$ finds its direct and practical application in i) assay development and validation and ii) assessment of the susceptibility or sensitivity of different cell types or tissues to undertake the reaction under study and to be affected by it.

The Potency $\pi$ $\pi$ measures the intrinsic potency of the biological agent to accomplish P against the resistance ($\kappa$) offered by the reaction process. For every infectious virus particle (R1) added to the assay, the actual activity of the virus added is given by $\pi R1$. In order to report an output P, the potency $\pi$ has to push forward the reaction inside the cell against $\kappa$. $\pi$ is specific to the particular biological agent for the reaction under study. $\pi$ is a feature of the biological agent.

Different versions or variants of the biological agent will display different $\pi$ for the same reaction. Thus, mutations, conformational changes or other modifications on the biological agent are expected to change its $\pi$ for a given reaction process.

The concept of $\pi$ is analogous to that of chemical activity by opposite to concentration for simple compounds. $\pi$ is a correction factor that affects the concentration (R1) of the biological agent to indicate its actual strength or activity for a given reaction process.

Variations in $\pi$ affect equation (2) by shifting the curve to the right or to the left, according to whether the value of $\pi$ decreases or increases, respectively. Curves differing only in $\pi$ are not parallel each other. The slope of the curve given by equation (2) increases as $\pi$ increases.

$\pi$ is a key parameter for the characterization of the biological agent and the assessment of its performance to accomplish the reaction under study. $\pi$ finds its direct and practical application in i) biological agent optimization and development as it allows to compare the relative potency of variants of the agent.

$\pi$ is a valuable tool in the field of vaccine, gene transfer vector and antibody development, for the comparison between two or more different agents or different versions of the same agent, for performance. Two agents, for instance, may elicit equivalent potencies for gene transfer, while their potencies for immunogenicity be different. The use of $\pi$, a quantitative and accurate parameter for assessing potency, will allow for ranking the candidates according to their potency (i.e., for gene transfer, gene expression, immunogenicity and other such properties and activities) and to make rational decisions about the relative value of the agent leads.

The Efficiency $\epsilon$ $\epsilon$ measures the maximal global efficiency of the reaction process when a biological agent characterized by a given $\pi$ value interacts with a biological system characterized by a given $\kappa$. $\epsilon$ is specific to the particular couple biological agent ($\pi$)/biological system ($\kappa$) for the reaction under study. $\epsilon$ is a feature of the global reaction process and intervening reagents. Changes in either $\pi$, $\kappa$, or both, will lead to changes in $\epsilon$.

The efficiency of the reaction process described by equation (2) is given by the increase in the output P that can be obtained by increasing the input R1. Thus, the first derivative of P with respect to R1, or the slope of the curve described by equation (2), gives the global efficiency of the reaction at every R1 input. The maximal global efficiency, or $\epsilon$, is given directly by either the slope at the inflection point of the curve described by equation (2) or by the maximum of its derivative $\delta P / \delta R1$. The slope of the curve given by equation (2) and the maximum of $\delta P / \delta R1$ increase as $\epsilon$ increases.

$\epsilon$ is a key parameter for the characterization of the efficiency global process, considering the assay conditions and reagents all together. It is therefore useful for assay optimization once $\pi$ and $\kappa$ have been fixed and to detect changes in $\pi$ when $\kappa$ is kept constant or, inversely, changes in $\kappa$ while $\pi$ is kept unchanged.

The Heterogeneity Index $\eta$ $\eta$ measures the internal heterogeneity of the reaction process under study. Complex processes include a huge chain of individual and casual events inside a multidimensional network of interrelated and interregulated biological reactions. Thus, the constant of resistance (κ) for the particular reaction process under study is a macroscopic indicator of the global resistance of that process (κ=a1κ1+a2κ2+ ... anκn/n). If the contribution of the individual microscopic constants of resistance (a1κ1, a2κ2, ... anκn) for the individual steps involved in the process were homogeneous and no thresholds were present from one step to the next, then, no discontinuities in the increase of the Hill coefficient (i.e. in the change of κ) with R1 should be observed. The existence of a major heterogeneity among the κi values corresponding to the microscopic individual steps (i.e. the existence of thresholds for the intermediate steps) might lead to a macroscopic discontinuity in the system. Heterogeneity would cause a change in the rate of variation of the Hill coefficient and, which would require a jump in the macroscopic value of κ in order for equation (2) to fit the data.

The presence of internal heterogeneity in the reaction process can be detected by the appearance of steps in the rate of change of the Hill coefficient, corresponding to the Hill curve that fits the experimental data. η_ is defined as an index of heterogeneity and its value corresponds to the number of steps in the rate of variation of the Hill coefficient (one step, η=1; two steps, η=2; n steps, η=n).

η is a key parameter for the dissection and detailed analysis of the reaction process. It is useful for the independent optimization and development of every one of the steps identified by η.

As mentioned, the presence of steps in the rate of change of η translates in an abrupt discontinuity in κ. Therefore, every step is determined by a different macroscopic constant of resistance κ. Systems with η=2, can thus be described by a Hill equation in which κ takes two different values (κ1 and κ2), according to the R1 interval considered. One part of the curve is described by κ1 and the other by κ2.

Hill curves describing reaction processes characterized by η=2, are hybrids generated from two parallel Hill curves differing only in κ. The transition from one curve to the other may alter the smooth change in the slope of the resulting Hill curve.

The Apparent Titer τ

In the Hill equation (2), when R1 increases, r increases from 1 to 2, 3, 4 ... and P approaches its $P_{max}$ value. On the other direction, on the contrary, R1 can only decrease up to a minimal point ($R1_{min}$), at which r and P reach their minimal values. The Hill sigmoidal curve is not symmetric, only the right arm is asymptotic (towards $P_{max}$). On the left arm, the curve has an origin at $R1_{min}$; the empirical curve does not fit the data for values below $R1_{min}$.

From a biological point of view, the fact that P does not exist for R1 below $R1_{min}$, means that there is no 'product' when the concentration of 'substrate' is lower than $R1_{min}$; e.g. that the system is not responsive to concentrations below $R1_{min}$. The minimal concentration of R1 that the system can detect and report is $R1_{min}$.

In terms of biological agents, $R1_{min}$ represents the minimal amount that can elicit a response in a given reporter system, and it is represented by τ. The titer defined this way, is neither an asymptote value nor a value approached by extrapolation, but a precise parameter of the Hill equation, at the very mathematical origin of the curve.

τ measures the limiting dilution or apparent titer of the biological reagent. The value of τ is determined by the limit of sensitivity of the biological assay system and of method used for the measurement of the product P; that is why it is said to be apparent titer.

τ is specific to the batch or stock of the biological reagent tested. τ represents the apparent concentration of the biological agent and is expressed in units per volume, e.g. the maximal dilution of the biological agent that leads to the production of P. τ is given by the maximal R1 for which the Hill coefficient reaches its minimal value (the Hill coefficient becomes constant at a value equal or close to 1). The concept of τ corresponds to that of titer, of general use for viruses, antibodies and vectors. Variations in τ affect equation (2) by shifting the curve to the right or to the left, according to whether the value of τ decreases or increases, respectively.

τ is a key parameter that measures the 'apparent' concentration of a stock of the biological agent, which is necessary for whatever use it will be given.

The Absolute Titer θ

θ is a the parameter that measures the absolute concentration (titer) of a stock or batch of the biological agent. The value of θ is not determined by nor dependent on the limit of sensitivity of the biological assay system or of the method used for the measurement of the product P; that is why it is said to be absolute titer. θ is specific to the batch or stock of the biological reagent tested. It represents the real physical concentration of the biological agent and is expressed in units per volume, e.g. the maximal dilution of the biological agent that leads to the production of P.

θ is given by the following equation $$\theta\pi = \tau/s \quad (3),$$

where s is the sensitivity of the detection method. Therefore, for agents detected using the same method, the following expression is valid:

$$\theta 1\pi 1/\tau 1 = \theta 2\pi 2/\tau 2 = \theta n\pi n/\tau n = \text{constant} \quad (4)$$

Using equation (4), the ratio of the absolute titer θ, corresponding to two biological agent preparations, can be obtained from their respective π and τ. Variations in θ affect the equation (2) by shifting the curve to the right or to the left and/or by changing its slope.

Compensation Between π and κ

π and κ may appear to compensate to generate two different Hill curves (one differing in π and the other one differing in κ) that would apparently fit with the same experimental data. As π and κ have opposite effects, two Hill curves; in which the increase in π is compensated by the decrease in κ, and vice versa, may seem to represent the same curve, which could make it difficult to determine whether two Hill curves are different because a change in π or in κ.

Detailed analysis of the Hill curves indicates that π and κ do not compensate very well. Although curves differing in compensatory values of either π or κ may vary close each other, they do not fit exactly in any of the two regions of highest curvature (before and after the inflection point). This dispersion is caused by the fact that π, but not κ, changes the slope at the inflection point of the Hill curve. Therefore, ε, which is the slope of the Hill curve at the inflection point, can be used to easily differentiate between two Hill curves that apparently compensate for π and κ.

Conclusions

The application of the Hill analysis to resolve complex biological processes is effective for the precise and objective understanding of processes like virus or vaccine action, entry, genome replication, transgene expression, vector/transgene immunogenicity, cytotoxicity and other such parameters. The analysis is independent of the virus vaccine, vector and protein type involved and from the output parameter and variable measured, such as the internalized vector DNA, transgene mRNA level and transgene product activity.

As in the field of chemical pharmaceuticals, the structure of the potential drug (in this case the biological agent) must be optimized to a maximal possible intrinsic potency. In analytical development, the goal is to search for better performing reporter systems (the lowest possible κ), as analytical tool. Two different systems characterized by constants κA and κB, respectively, can be compared (using the same biological agent) for their relative resistance or performance.

Complex systems involving the interaction of biological agents, such as viruses, vaccines, gene transfer vectors, antibodies proteins and living cells (either in vitro or in vivo) can be analyzed using the Hill equation. A complex succession of unitary processes, each of them susceptible to be individually analyzed by the Hill equation, as a global process, can be also described by the same equation as its constitutive steps.

EXAMPLE 4

Materials and Methods

Cells 293 human embryo kidney (HEK) cells, obtained from ATCC, were cultured in Dulbecco's modified Eagle's medium containing 4.5 g/l glucose (DMEM; GIBGO-BRL) 10% fetal bovine serum (FBS, Hyclone). Hela rep-cap 32 cells, described above, were obtained from Anna Salvetti (CHU, Nantes) and cultured in the medium described above.

Plasmids pNB-Adeno, which encodes the entire E2A and E4 regions and VA RNA I and II genes of Adenovirus type 5, was constructed by ligating into the polylinker of multiple cloning site of pBSII KS (+/−) (Stratagene, San Diego, USA) the SalI-HindIII fragment (9842-11555 nt) of Adenovirus type 5 and the BamHI-ClaI fragment (21563-35950) of pBR325. All fragments of adenovirus gene were obtained from the plasmid pBHG-10 (Microbix, Ontario, Canada). pNB-AAV encodes the genes rep and cap of AAV-2 and was constructed by ligation of XbaI-XbaI PCR fragment containing the genome of AAV-2 from nucleotide 200 to 4480 into XbaI site of polylinker MOS of pBSIIKS(+/−). The PCR fragment was obtained from pAV1 (ATCC, USA). Plasmid pNB-AAV was derived from plasmid pVA1l, which contains the AAV genomic region, rep and cap. pNB-AAV does not contain the AAV ITR's present in pAV1. pAAV-CMV(nls)LacZ was provided by Dr Anna Salvetti (CHU, Nantes). Plasmid pCMV(nls)LacZ (rAAV vector plasmid) and pNB-Adeno were prepared in DH5a E. coli and purified by Nucleobond AX PC500 Kit (Macherey-Nagel), according to standard procedures. Plasmid pAAV-CMV(nls)LacZ is derived from plasmid psub201 by deleting the rep-cap region with SnaB I and replacing it with an expression cassette harboring the cytomegalovirus (CMV) immediate early promoter (407 bp), the nuclear localized β-galactosidase gene and the bovine growth hormone polyA signal (324 bp) (see, Chadeuf et al. (2000) J. Gene Med. 2:260-268. pAAV-CMV(nls)LacZ was provided by Dr Anna Salvetti.

Virus

Wild type adenovirus (AV) type 5 stock, originally provided by Dr Philippe Moullier (CHU, Nantes), was produced accordingly to standard procedures.

Construction of Rep Mutant Libraries 25 pmol of each mutagenic primer was placed into a 96 PCR well plate. 15 μl of reaction mix (0.25 pmol of pNB-AAV), 25 pmol of the selection primer (changing one non-essential unique restriction site to a new restriction site), 2 μl of 10× mutagenesis buffer (100 mM Tris-acetate pH7.5, 100 mM MgOAc and 500 mM KOAc pH7.5) was added into each well. The samples were incubated at 98° C. for 5 minutes and then immediately incubated for 5 minutes on ice. Finally, the plate was placed at room temperature for 30 minutes.

The primer extension and ligation reactions of the new strands were completed by adding to each sample: 7 μl of nucleotide mix (2.86 mM each nucleotide and 1.43× mutagenesis buffer) and 3 μl of a fresh 1:10 enzyme dilution mix (0.025 U/μl of native T7 DNA polymerase and 1 U/μl of T4 DNA ligase were diluted in 20 mM Tris HCl pH7.5, 10 mM KCl, 10 mM β-mercaptoethanol, 1 mM DTT, 0.1 mM EDTA and 50% glycerol). Samples were incubated at 37° C. for 1 hour. The T4 DNA ligase was inactivated by incubating the reactions at 72° C. for 15 minutes to prevent re-ligation of the digested strands during the digestion of the parental plasmid (pNB-AAV).

Each mutagenesis reaction was digested with restriction enzyme to eliminate parental plasmids: 30 μl solution containing 3 μl of 10× enzyme digestion buffer and 10 units of restriction enzyme were added to each mutagenesis reaction and incubated at 37° C. for at least 3 hours.

90 μl of the E. coli XLmutS competent cells (Stratagene, San Diego Calif.; supplemented with 1.5 μl of β-mercaptoethanol to a final concentration of 25 mM) were aliquoted into prechilled deep-well plates. The plates were incubated on ice for 10 minutes and swirling gently every 2 minutes.

A fraction of the reactions that had been digested with restriction enzyme (1/10 of the total volume) was added to the deep well plates. The plates were swirled gently prior to incubation on ice for 30 minutes. A heat pulse was performed in a 42° C. water bath for 45 seconds, the transformation mixture was incubated on ice for 2 minutes and 0.45 ml of preheated SOC medium (2% (w/v) tryptone, 0.5% (w/v) yeast extract, 8.5 mM NaCl, 2.5 mM KCl, 10 mM $MgCl_2$ and 20 mM glucose at pH 7) was added. The plates were incubated at 37° C. for 1 hour with shaking.

To enrich for mutant plasmids, 1 ml of 2×YT broth medium (YT medium is 0.5% yeast extract, 0.5% NaCl, 0.8% bacto-tryptone), supplemented with 100 μg/ml of ampicillin, was added to each transformation mixture and the cultures were grown overnight at 37° C. with shaking. Plasmid DNA isolation was performed from each mutant culture using standard procedure described in Nucleospin Multi-96 Plus Plasmid Kit (Macherey-Nagel). Five hundred μg of the resulting isolated DNA was digested with 10 units of the selection restriction enzyme in a total volume of 30 μl containing 3 μl of 10× enzyme digestion buffer for overnight at 37° C.

A fraction of the digested reactions (1/10 of the total volume) were transformed into 40 μl of *Epicurian coli* XL1-Blue competent cells supplemented with 0.68 μl of β-mercaptoethanol to a final concentration of 25 mM. After heat pulse, 0.45 ml of SOC was added and the transformation mixtures were incubated for 1 hour at 37° C. with shaking before to be plate on LB-ampicillin agar plates. The agar plates were incubated overnight at 37° C. and the colonies obtained were picked up and grown overnight at 37° C. into deep-well plates.

Four clones per reaction were screened for the presence of the mutation using restriction enzyme specific to the new restriction site introduced into the mutated plasmid with the selection primer. The cDNA from selected clones was also sequenced to confirm the presence of the expected mutation.

Monitoring rAAV Production rAAV from each of the above wells, were produced by triple transfection on 293 HEK cells. $3 \times 10^4$ cells were seeded into each well of 96 micro-well plate and cultured for 24 hours before transfection. Transfection was made on cells at about 70% confluency. 25 kDa PEI (poly-ethylene-imine, Sigma-Aldrich) was used for the triple transfection step. Equimolar amounts of the three plasmids AV helper plasmid (pNB-Adeno), AAV helper plasmid (pNB-AAV or a mutant clone rep plasmid) and vector plasmid (pAAV-CMV(nls) LacZ) were mixed with 10 mM PEI by gently shaking. The mixture was the added to the medium culture on the cells. 60 hours after transfection, the culture medium was replaced with 100 µl of lysis buffer (50 mM Hepes, pH 7.4; 150 mM NaCl; 1 m MgCl$_2$; 1 mM CaCl$_2$; 0.01% CHAPS). After one cycle of freeze-thawing the cellular lysate was filtered through a millipore filter 96 well plate and stored at 80° C.

rAAV Infection Particles (ip)

Titers of rAAV vector particles were determined on HeLa rep/cap 32 cells using standard dRA (serial dilution replication assay) test. Cells were plated 24 hours before infection at a density of 1×10$^4$ cells in 96-well plates. Serial dilutions of the rAAV preparation were made between 1 and 1×10$^6$ µl and used for co-infection of the HeLa rep/cap 32 cells together with wt-AV type 5 (MOI 25). 48 hours after infection the ip were measured by real time PCR or by the quantification of biological activity of the transgene.

Real Time PCR

Infected HeLa rep/cap 32 cells were lysed with 50 µl of solution (50 mM Hepes, pH 7.4; 150 mM NaCl). After one cycle of freeze-thawing 50 µl of Proteinase K (10 mg/ml) and the lysate were incubated one hour at 55° C. The enzyme was inactivated by incubation 10 min at 96° C.

For real time PCR, 0.2 µl of lysate was taken. Final volume of the reaction was 10 µl in 384 well plate using an Applied Biosystem Prism 7900. The primers and fluorescence probe set corresponding to the CMV promoter were as follows: CMV 1 primer 5'-TGCCAAGTACGCCCCCTAT-3' (SEQ ID No. 733) (0.2 µM) and CMV 2 primer 5'-AGGTCATG-TACTGGGCATAATGC-3' (SEQ ID No. 734) (0.2 µM); probe VIC-Tamra 5'-TCAATGACGGTAAATGGC-CCGCCT-3' (SEQ ID No. 735) (0.1 µM). dRA plots were obtained by plotting the DNA copy number (obtained by real time PCR) vs. the dilution of the rAAV preparation.

β-Galactosidase Activity

After 48 hours of infection, cells were treated with trypsin, and 100 µl of reaction solution (GalScreen Kit, Tropix) was added and incubated for one hour at 26° C. Luminescence was measured in NorthStar (Tropix) HTS station. dRA plots were obtained plotting the intensity of β-Galatosidase activity vs. the dilution of the rAAV preparation.

Mathematical Model for Results Analysis

Results were analyzed using the Hill equation-based analysis (designated NautScan™; see, Patent no 9915884, 1999, France; published as International PCT application No. WO 01/44809 (PCT no PCT/FR00/03503, December, 2000, see EXAMPLE above). Briefly, data were processed using a Hill equation-based model that allows extraction of key feature indicators of performance for each individual mutant. Mutants were ranked based on the values of their individual performance and those at the top of the ranking list were selected as Leads.

Results

Generation of Diversity

To identify candidate amino acid (aa) positions on the rep protein involved in rep protein activity an Ala-scan was performed on the rep sequence. For this, each amino acid in the rep protein sequence was replaced with Alanine. To do this sets of rAAV that encode mutant rep proteins in which each differs from wild type by replacement of one amino acid with Ala, were generated. Each set of rAAV was individually introduced into cells in a well of a microtiter plate, under conditions for expression of the rep protein. The amount of virus that could be produced from each variant was measured as described below. Briefly, activity of Rep was assessed by determining the amount of AAV or rAAV produced using infection assays on HeLa Rep-cap 32 cells and by measurement of AAV DNA replication using Real Time PCR, or by assessing transgene (β-galactosidase) expression. The relative activity of each individual mutant compared to the native protein was assessed and "hits" identified. Hit positions are the positions in the mutant proteins that resulted in an alteration (selected to be at least about 20%), in this instance all resulted in a decrease, in the amount of virus produced compared to the activity of the native (wildtype) gene (see FIG. 3A).

The hits were then used for identification of leads (see, FIG. 3B). Assays for Rep activity were performed as described for identification of the hit positions. Hit positions on Rep proteins and the effect of specific amino acids on the productivity of AAV-2 summarized in the following table:

| Hit position | replacing amino acid (effect) | |
|---|---|---|
| 4 (ttt) F | (gct) A (decrease) | |
| 10 (aag) K | (gcg) A (decrease) | |
| 20 (ccc) P | (gcc) A (decrease) | |
| 22 (att) I | (gct) A (decrease) | |
| 28 (tgg) W | (gcg) A (decrease) | |
| 32 (gag) E | (gcg) A (decrease) | |
| 38 (ccg) P | (gcg) A (decrease) | |
| 39 (cca) P | (gca) A (decrease) | |
| 54 (ctg) L | (gct) A (decrease) | |
| 59 (ctg) L | (gcg) A (decrease) | |
| 64 (ctg) L | (gcg) A (decrease) | |
| 74 (ccg) P | (gcg) A (decrease) | |
| 86 (gag) E | (gcg) A (decrease) | |
| 88 (tac) Y | (gcc) A (decease) | |
| 101 (aaa) K | (gca) A (decrease) | |
| 124 (atc) I | (gcc) A (decrease) | |
| 125 (gag) E | (gcg) A (decrease) | |
| 127 (act) T | (gct) A (decrease) | |
| 132 (ttc) F | (gcc) A (decrease) | |
| 140 (ggc) G | (gcc) A (decrease) | |
| 161 (acc) T | (gcc) A (decrease) | |
| 163 (cct) P | (gct) A (decrease) | |
| 175 (tat) Y | (gct) A (decrease) | |
| 193 (ctg) L | (gcg) A (decrease) | |
| 196 (gtg) V | (gcg) A (decrease) | |
| 197 (tcg) S | (gcc) A (decrease) | |
| 221 (tca) S | (gca) A (decrease) | |
| 228 (gtc) V | (gcg) A (decrease) | |
| 231 (ctc) L | (gcc) A (decrease) | |
| 234 (aag) K | (gcg) A (decrease) | |
| 237 (acc) T | (gcc) A (decrease) | |
| 250 (tac) Y | (gcc) A (decrease) | |
| 258 (aac) N | (gcc) A (decrease) | |
| 260 (cgg) R | (gcg) A (decrease) | |
| 263 (atc) I | (gcc) A (decrease) | |
| 264 (aag) K | (gcg) A (decrease) | |
| 334 (ggg) G | (gcg) A (decrease) | |
| 335 (cct) V | (gct) A (decrease) | |
| 337 (act) T | (gct) A (decrease) | |
| 341 (acc) T | (gcc) A (decrease) | |
| 342 (aac) N | (gcc) A (decrease) | |
| 347 (ata) I | (gca) A (decrease) | |
| 350 (act) T | (gct) A (decrease | (aat) N (increase) |
| 354 (tac) Y | (gcc) A (decrease) | |
| 363 (aac) N | (gcc) A (decrease) | |
| 364 (ttt) F | (gct) A (decrease) | |
| 367 (aac) N | (gcc) A (decrease) | |
| 370 (gtc) V | (gcc) A (decrease) | |
| 376 (tgg) W | (gcg) A (decrease) | |
| 381 (aag) K | (gcg) A (decrease) | |

-continued

| Hit position | replacing amino acid (effect) | |
|---|---|---|
| 382 (atg) M | (gcg) A (decrease) | |
| 389 (tcg) S | (gcg) A (decrease) | |
| 407 (tcc) S | (gcc) A (decrease) | |
| 411 (ata) I | (gca) A (decrease) | |
| 414 (act) T | (gct) A (decrease) | |
| 420 (tcc) S | (gct) A (decrease) | |
| 421 (aac) N | (gcc) A (decrease) | |
| 422 (acc) T | (gcc) A (decrease) | |
| 424 (atg) M | (gcg) A (decrease) | |
| 428 (att) I | (gct) A (decrease) | |
| 429 (gac) D | (gcc) A (decrease) | |
| 438 (cag) Q | (gcg) A (decrease) | |
| 440 (ccg) P | (gcg) A (decrease) | |
| 451 (acc) T | (gcc) A (decrease) | |
| 460 (aag) K | (gcg) A (decrease) | |
| 462 (acc) T | (gcc) A (decrease) | (ata) I (increase) |
| 484 (ttc) F | (gcc) A (decrease) | |
| 488 (aag) K | (gcg) A (decrease) | |
| 495 (ccc) P | (gcc) A (decrease) | |
| 497 (ccc) P | (gcc) A (decrease) | (cga) R (increase) |
| 497 (ccc) P | (gcc) A (decrease) | (ctc) L (increase) |
| 497 (ccc) P | (gcc) A (decrease) | (tac) Y (increase) |
| 498 (agt) S | (gct) A (decrease) | |
| 499 (gac) D | (gcc) A (decrease) | |
| 503 (agt) S | (gcg) A (decrease) | |
| 511 (tca) S | (gca) A (decrease) | |
| 512 (gtt) V | (gct) A (decrease) | |
| 516 (tcg) S | (gcg) A (decrease) | |
| 517 (acg) T | (gct) A (decrease) | (aac) N (increase) |
| 518 (tca) S | (gca) A (decrease) | |
| 519 (gac) D | (gcg) A (decrease) | |
| 542 (ctg) L | (gcg) A (decrease) | (tcg) S (increase) |
| 548 (aga) R | (gca) A (decrease) | (agc) S (increase) |
| 598 (gga) G | (gca) A (decrease) | (gac) D (increase) |
| 598 (gga) G | (gca) A (decrease) | (agc) S (increase) |
| 600 (gtg) V | (gcg) A (decrease) | (ccg) P (increase) |
| 601 (cca) P | (gca) A (decrease) | |
| Hit position (within intron) | replacing sequence (effect) | |
| 630 (tgc) | gcg (decrease) | cgc or tca or cct (increase) |

The hits in other AAV serotypes (see, also FIGS. 5A and 5B) are as follows:

| HIT POSITION | | | | | | |
|---|---|---|---|---|---|---|
| AAV-2 | AAV-1 | AAV-3 | AAV-3B | AAV-4 | AAV-6 | AAV-5 |
| 4 | 4 | 4 | 4 | 4 | 4 | 4 |
| 10 | 10 | 10 | 10 | 10 | 10 | 10 |
| 20 | 20 | 20 | 20 | 20 | 20 | 20 |
| 22 | 22 | 22 | 22 | 22 | 22 | 22 |
| 29 | 29 | 29 | 29 | 29 | 29 | 29 |
| 32 | 32 | 32 | 32 | 32 | 32 | 32 |
| 38 | 38 | 38 | 38 | 38 | 38 | 38 |
| 39 | 39 | 39 | 39 | 39 | 39 | 39 |
| 54 | 54 | 54 | 54 | 54 | 54 | 54 |
| 59 | 59 | 59 | 59 | 59 | 59 | 59 |
| 64 | 64 | 64 | 64 | 64 | 64 | 64 |
| 74 | 74 | 74 | 74 | 74 | 74 | |
| 86 | 86 | 86 | 86 | 86 | 86 | 85 |
| 88 | 88 | 88 | 88 | 88 | 88 | 87 |
| 101 | 101 | 101 | 101 | 101 | 101 | 100 |
| 124 | 124 | 124 | 124 | 124 | 124 | 123 |
| 125 | 125 | 125 | 125 | 125 | 125 | 124 |
| 127 | 127 | 127 | 127 | 127 | 127 | 126 |
| 132 | 132 | 132 | 132 | 132 | 132 | 131 |
| 140 | 140 | 140 | 140 | 140 | 140 | |
| 161 | 161 | 161 | 161 | 161 | 161 | 158 |
| 163 | 163 | 163 | 163 | 163 | 163 | 160 |
| 175 | 175 | 175 | 175 | 175 | 175 | 172 |
| 193 | 193 | 193 | 193 | 193 | 193 | 190 |

-continued

| HIT POSITION | | | | | | |
|---|---|---|---|---|---|---|
| AAV-2 | AAV-1 | AAV-3 | AAV-3B | AAV-4 | AAV-6 | AAV-5 |
| 196 | 196 | 196 | 196 | 196 | 196 | 193 |
| 197 | 197 | 197 | 197 | 197 | 197 | 194 |
| 221 | 221 | 221 | 221 | 221 | 221 | 217 |
| 228 | 228 | 228 | 228 | 228 | 228 | 224 |
| 231 | 231 | 231 | 231 | 231 | 231 | 227 |
| 234 | 234 | 234 | 234 | 234 | 234 | 230 |
| 237 | 237 | 237 | 237 | 237 | 237 | 233 |
| 250 | 250 | 250 | 250 | 250 | 250 | 246 |
| 258 | 258 | 258 | 258 | 258 | 258 | 254 |
| 260 | 260 | 260 | 260 | 260 | 260 | 256 |
| 263 | 263 | 263 | 263 | 263 | 263 | 259 |
| 264 | 264 | 264 | 264 | 264 | 264 | 260 |
| 334 | 334 | 334 | 334 | 334 | 334 | 330 |
| 335 | 335 | 335 | 335 | 335 | 335 | 331 |
| 337 | 337 | 337 | 337 | 337 | 337 | 333 |
| 341 | 341 | 341 | 341 | 341 | 341 | 337 |
| 342 | 342 | 342 | 342 | 342 | 342 | 338 |
| 347 | 347 | 347 | 347 | 347 | 347 | 342 |
| 350 | 350 | 350 | 350 | 350 | 350 | 346 |
| 354 | 354 | 354 | 354 | 354 | 354 | 350 |
| 363 | 363 | 363 | 363 | 363 | 363 | 359 |
| 364 | 364 | 364 | 364 | 364 | 364 | 360 |
| 367 | 367 | 367 | 367 | 367 | 367 | 363 |
| 370 | 370 | 370 | 370 | 370 | 370 | 366 |
| 376 | 376 | 376 | 376 | 376 | 376 | 372 |
| 381 | 381 | 381 | 381 | 381 | 381 | 377 |
| 382 | 382 | 382 | 382 | 382 | 382 | 378 |
| 389 | 389 | 389 | 389 | 389 | 389 | 385 |
| 407 | 407 | 407 | 407 | 407 | 407 | 403 |
| 411 | 411 | 411 | 411 | 411 | 411 | 407 |
| 414 | 414 | 414 | 414 | 414 | 414 | 410 |
| 420 | 420 | 420 | 420 | 420 | 420 | 416 |
| 421 | 421 | 421 | 421 | 421 | 421 | 417 |
| 422 | 422 | 422 | 422 | 422 | 422 | 418 |
| 424 | 424 | 424 | 424 | 424 | 424 | 420 |
| 428 | 428 | 428 | 428 | 428 | 428 | 424 |
| 429 | 429 | 429 | 429 | 429 | 429 | 425 |
| 438 | 438 | 438 | 438 | 438 | 438 | 434 |
| 440 | 440 | 440 | 440 | 440 | 440 | 436 |
| 451 | 451 | 451 | 451 | 451 | 451 | 447 |
| 460 | 460 | 460 | 460 | 460 | 460 | 456 |
| 462 | 462 | 462 | 462 | 462 | 462 | 458 |
| 484 | 484 | 484 | 484 | 484 | 484 | 480 |
| 488 | 488 | 488 | 488 | 488 | 488 | 484 |
| 495 | 495 | 495 | 495 | 495 | 495 | 491 |
| 497 | 497 | 497 | 497 | 497 | 497 | 493 |
| 498 | 498 | 498 | 498 | 498 | 498 | 494 |
| 499 | 499 | 499 | 499 | 499 | 499 | 495 |
| 503 | 503 | 503 | 503 | 503 | 503 | 499 |
| 511 | 511 | 511 | 511 | 511 | 511 | 529 |
| 512 | 512 | 512 | 512 | 512 | 512 | 530 |
| 516 | 516 | 516 | 516 | 516 | 516 | 534 |
| 517 | 517 | 517 | 517 | 517 | 517 | 535 |
| 518 | 518 | 518 | 518 | 518 | 518 | 536 |
| 519 | 519 | 519 | 519 | 519 | 519 | 537 |
| 542 | 543 | 542 | 542 | 542 | 543 | 561 |
| 548 | 549 | 548 | 548 | 548 | 549 | 567 |
| 598 | 599 | 600 | 600 | 599 | 599 | |
| 600 | 602 | 603 | 603 | 602 | 602 | 589 |
| 601 | 603 | 604 | 604 | 603 | 603 | 590 |

Sets of nucleic acids encoding the rep protein were generated. The rep proteins encoded by these sets of nucleic acid molecules were those in which each amino acid position identified as a "hit" in the ala-scan step, were each sequentially replaced by all remaining 18 amino acids using site directed mutagenesis. Each mutant was designed, generated, processed and analyzed physically separated from the others in addressable arrays. No mixtures, pools, nor combinatorial processing were used.

As in the first round (alanine scan), a library of mutant rAAV was generated in which each individual mutant was independently and individually generated in a independent reaction and such that each mutant contains only a single amino acid change and this for each amino acid residue. Again, each resulting mutant rep protein was then expressed and the amount of virus produced in cells assessed and compared to the native protein.

Lead Identification

Since rep proteins that result in increased virus production are of interest, those mutants that lead to an increase in the amount of virus produced (2 to 10 times the native activity), were selected as "leads." Ten such mutants were identified.

Based on the results obtained from the assays described above (i.e. titer of virus produced by each rep variant), each individual rep variant was assigned a specific activity. Those variant proteins displaying the highest titers were selected as leads (see Table above). Leads include: amino acid replacement of T by N at Hit position 350; T by I at Hit position 462; P by R at Hit position 497; P by L at Hit position 497; P by Y at Hit position 497; T by N at Hit position 517; G by S at Hit position 598; G by D at Hit position 598; V by P at Hit position 600.

Also provided are combinations of the above mutant Rep 78, 68, 52, 40 proteins, nucleic acids encoding the proteins, and recombinant AAV (any serotype) containing the mutation at the indicated position or corresponding position for serotypes other than AAV-2, including any set forth in the following table and corresponding SEQ ID Nos. Each amino acid sequence is set forth in a separate sequence ID listing; for each mutation or combination thereof there is a single SEQ ID setting forth the unspliced nucleic acid sequence for Rep78/68, which for all mutations from amino acid 228 on, includes the corresponding Rep 52 and Rep 40 encoding sequence as well.

Amino Acid Sequences of Exemplary Mutant Rep Proteins

| Seq no. | gene  | position(s) | codon(s) |
|---------|-------|-------------|----------|
| seq.1   | rep78 | 4           | GCT      |
| seq.2   | rep68 | 4           | GCT      |
| seq.3   | rep78 | 10          | GCG      |
| seq.4   | rep68 | 10          | GCG      |
| seq.5   | rep78 | 20          | GCC      |
| seq.6   | rep68 | 20          | GCC      |
| seq.7   | rep78 | 22          | GCT      |
| seq.8   | rep68 | 22          | GCT      |
| seq.9   | rep78 | 29          | GCG      |
| seq.10  | rep68 | 29          | GCG      |
| seq.11  | rep78 | 38          | GCG      |
| seq.12  | rep68 | 38          | GCG      |
| seq.13  | rep78 | 39          | GCA      |
| seq.14  | rep68 | 39          | GCA      |
| seq.15  | rep78 | 53          | GCT      |
| seq.16  | rep68 | 53          | GCT      |
| seq.17  | rep78 | 59          | GCG      |
| seq.18  | rep68 | 59          | GCG      |
| seq.19  | rep78 | 64          | GCT      |
| seq.20  | rep68 | 64          | GCT      |
| seq.21  | rep78 | 74          | GCG      |
| seq.22  | rep68 | 74          | GCG      |
| seq.23  | rep78 | 86          | GCG      |
| seq.24  | rep68 | 86          | GCG      |
| seq.25  | rep78 | 88          | GCC      |
| seq.26  | rep68 | 88          | GCC      |
| seq.27  | rep78 | 101         | GCA      |
| seq.28  | rep68 | 101         | GCA      |
| seq.29  | rep78 | 124         | GCC      |
| seq.30  | rep68 | 124         | GCC      |
| seq.31  | rep78 | 125         | GCG      |
| seq.32  | rep68 | 125         | GCG      |
| seq.33  | rep78 | 127         | GCT      |
| seq.34  | rep68 | 127         | GCT      |
| seq.35  | rep78 | 132         | GCC      |
| seq.36  | rep68 | 132         | GCC      |
| seq.37  | rep78 | 140         | GCC      |
| seq.38  | rep68 | 140         | GCC      |
| seq.39  | rep78 | 161         | GCC      |
| seq.40  | rep68 | 161         | GCC      |
| seq.41  | rep78 | 163         | GCT      |
| seq.42  | rep68 | 163         | GCT      |
| seq.43  | rep78 | 175         | GCT      |
| seq.44  | rep68 | 175         | GCT      |
| seq.45  | rep78 | 193         | GCG      |
| seq.46  | rep68 | 193         | GCG      |
| seq.47  | rep78 | 196         | GCC      |
| seq.48  | rep68 | 196         | GCC      |
| seq.49  | rep78 | 197         | GCC      |
| seq.50  | rep68 | 197         | GCC      |
| seq.51  | rep78 | 221         | GCA      |
| seq.52  | rep68 | 221         | GCA      |
| seq.53  | rep78 | 228         | GCG      |
| seq.54  | rep52 | 228         | GCG      |

-continued

| | | | |
|---|---|---|---|
| seq.55 | rep68 | 228 | GCG |
| seq.56 | rep40 | 228 | GCG |
| seq.57 | rep78 | 231 | GCC |
| seq.58 | rep52 | 231 | GCC |
| seq.59 | rep68 | 231 | GCC |
| seq.60 | rep40 | 231 | GCC |
| seq.61 | rep78 | 234 | GCG |
| seq.62 | rep52 | 234 | GCG |
| seq.63 | rep68 | 234 | GCG |
| seq.64 | rep40 | 234 | GCG |
| seq.65 | rep78 | 237 | GCC |
| seq.66 | rep52 | 237 | GCC |
| seq.67 | rep68 | 237 | GCC |
| seq.68 | rep40 | 237 | GCC |
| seq.69 | rep78 | 250 | GCC |
| seq.70 | rep52 | 250 | GCC |
| seq.71 | rep68 | 250 | GCC |
| seq.72 | rep40 | 250 | GCC |
| seq.73 | rep78 | 258 | GCC |
| seq.74 | rep52 | 258 | GCC |
| seq.75 | rep68 | 258 | GCC |
| seq.76 | rep40 | 258 | GCC |
| seq.77 | rep78 | 260 | GCG |
| seq.78 | rep52 | 260 | GCG |
| seq.79 | rep68 | 260 | GCG |
| seq.80 | rep40 | 260 | GCG |
| seq.81 | rep78 | 263 | GCC |
| seq.82 | rep52 | 263 | GCC |
| seq.83 | rep68 | 263 | GCC |
| seq.84 | rep40 | 263 | GCC |
| seq.85 | rep78 | 264 | GCG |
| seq.86 | rep52 | 264 | GCG |
| seq.87 | rep68 | 264 | GCG |
| seq.88 | rep40 | 264 | GCG |
| seq.89 | rep78 | 334 | GCG |
| seq.90 | rep52 | 334 | GCG |
| seq.91 | rep68 | 334 | GCG |
| seq.92 | rep40 | 334 | GCG |
| seq.93 | rep78 | 335 | GCT |
| seq.94 | rep52 | 335 | GCT |
| seq.95 | rep68 | 335 | GCT |
| seq.96 | rep40 | 335 | GCT |
| seq.97 | rep78 | 337 | GCT |
| seq.98 | rep52 | 337 | GCT |
| seq.99 | rep68 | 337 | GCT |
| seq.100 | rep40 | 337 | GCT |
| seq.101 | rep78 | 341 | GCC |
| seq.102 | rep52 | 341 | GCC |
| seq.103 | rep68 | 341 | GCC |
| seq.104 | rep40 | 341 | GCC |
| seq.105 | rep78 | 342 | GCC |
| seq.106 | rep52 | 342 | GCC |
| seq.107 | rep68 | 342 | GCC |
| seq.108 | rep40 | 342 | GCC |
| seq.109 | rep78 | 347 | GCA |
| seq.110 | rep52 | 347 | GCA |
| seq.111 | rep68 | 347 | GCA |
| seq.112 | rep40 | 347 | GCA |
| seq.113 | rep78 | 350 | AAT |
| seq.114 | rep52 | 350 | AAT |
| seq.115 | rep68 | 350 | AAT |
| seq.116 | rep40 | 350 | AAT |
| seq.117 | rep78 | 350 | GCT |
| seq.118 | rep52 | 350 | GCT |
| seq.119 | rep68 | 350 | GCT |
| seq.120 | rep40 | 350 | GCT |
| seq.121 | rep78 | 354 | GCC |
| seq.122 | rep52 | 354 | GCC |
| seq.123 | rep68 | 354 | GCC |
| seq.124 | rep40 | 354 | GCC |
| seq.125 | rep78 | 363 | GCC |
| seq.126 | rep52 | 363 | GCC |
| seq.127 | rep68 | 363 | GCC |
| seq.128 | rep40 | 363 | GCC |
| seq.129 | rep78 | 364 | GCT |
| seq.130 | rep52 | 364 | GCT |
| seq.131 | rep68 | 364 | GCT |
| seq.132 | rep40 | 364 | GCT |
| seq.133 | rep78 | 367 | GCC |

-continued

| | | | |
|---|---|---|---|
| seq.134 | rep52 | 367 | GCC |
| seq.135 | rep68 | 367 | GCC |
| seq.136 | rep40 | 367 | GCC |
| seq.137 | rep78 | 370 | GCC |
| seq.138 | rep52 | 370 | GCC |
| seq.139 | rep68 | 370 | GCC |
| seq.140 | rep40 | 370 | GCC |
| seq.141 | rep78 | 376 | GCG |
| seq.142 | rep52 | 376 | GCG |
| seq.143 | rep68 | 376 | GCG |
| seq.144 | rep40 | 376 | GCG |
| seq.145 | rep78 | 381 | GCG |
| seq.146 | rep52 | 381 | GCG |
| seq.147 | rep68 | 381 | GCG |
| seq.148 | rep40 | 381 | GCG |
| seq.149 | rep78 | 382 | GCG |
| seq.150 | rep52 | 382 | GCG |
| seq.151 | rep68 | 382 | GCG |
| seq.152 | rep40 | 382 | GCG |
| seq.153 | rep78 | 389 | GCG |
| seq.154 | rep52 | 389 | GCG |
| seq.155 | rep68 | 389 | GCG |
| seq.156 | rep40 | 389 | GCG |
| seq.157 | rep78 | 407 | GCC |
| seq.158 | rep52 | 407 | GCC |
| seq.159 | rep68 | 407 | GCC |
| seq.160 | rep40 | 407 | GCC |
| seq.161 | rep78 | 411 | GCA |
| seq.162 | rep52 | 411 | GCA |
| seq.163 | rep68 | 411 | GCA |
| seq.164 | rep40 | 411 | GCA |
| seq.165 | rep78 | 414 | GCT |
| seq.166 | rep52 | 414 | GCT |
| seq.167 | rep68 | 414 | GCT |
| seq.168 | rep40 | 414 | GCT |
| seq.169 | rep78 | 420 | GCT |
| seq.170 | rep52 | 420 | GCT |
| seq.171 | rep68 | 420 | GCT |
| seq.172 | rep40 | 420 | GCT |
| seq.173 | rep78 | 421 | GCC |
| seq.174 | rep52 | 421 | GCC |
| seq.175 | rep68 | 421 | GCC |
| seq.176 | rep40 | 421 | GCC |
| seq.177 | rep78 | 422 | GCC |
| seq.178 | rep52 | 422 | GCC |
| seq.179 | rep68 | 422 | GCC |
| seq.180 | rep40 | 422 | GCC |
| seq.181 | rep78 | 424 | GCG |
| seq.182 | rep52 | 424 | GCG |
| seq.183 | rep68 | 424 | GCG |
| seq.184 | rep40 | 424 | GCG |
| seq.185 | rep78 | 428 | GCT |
| seq.186 | rep52 | 428 | GCT |
| seq.187 | rep68 | 428 | GCT |
| seq.188 | rep40 | 428 | GCT |
| seq.189 | rep78 | 429 | GCC |
| seq.190 | rep52 | 429 | GCC |
| seq.191 | rep68 | 429 | GCC |
| seq.192 | rep40 | 429 | GCC |
| seq.193 | rep78 | 438 | GCG |
| seq.194 | rep52 | 438 | GCG |
| seq.195 | rep68 | 438 | GCG |
| seq.196 | rep40 | 438 | GCG |
| seq.197 | rep78 | 440 | GCG |
| seq.198 | rep52 | 440 | GCG |
| seq.199 | rep68 | 440 | GCG |
| seq.200 | rep40 | 440 | GCG |
| seq.201 | rep78 | 451 | GCC |
| seq.202 | rep52 | 451 | GCC |
| seq.203 | rep68 | 451 | GCC |
| seq.204 | rep40 | 451 | GCC |
| seq.205 | rep78 | 460 | GCG |
| seq.206 | rep52 | 460 | GCG |
| seq.207 | rep68 | 460 | GCG |
| seq.208 | rep40 | 460 | GCG |
| seq.209 | rep78 | 462 | GCC |
| seq.210 | rep52 | 462 | GCC |
| seq.211 | rep68 | 462 | GCC |
| seq.212 | rep40 | 462 | GCC |

-continued

| | | | |
|---|---|---|---|
| seq.213 | rep78 | 462 | ATA |
| seq.214 | rep52 | 462 | ATA |
| seq.215 | rep68 | 462 | ATA |
| seq.216 | rep40 | 462 | ATA |
| seq.217 | rep78 | 484 | GCC |
| seq.218 | rep52 | 484 | GCC |
| seq.219 | rep68 | 484 | GCC |
| seq.220 | rep40 | 484 | GCC |
| seq.221 | rep78 | 488 | GCG |
| seq.222 | rep52 | 488 | GCG |
| seq.223 | rep68 | 488 | GCG |
| seq.224 | rep40 | 488 | GCG |
| seq.225 | rep78 | 495 | GCC |
| seq.226 | rep52 | 495 | GCC |
| seq.227 | rep68 | 495 | GCC |
| seq.228 | rep40 | 495 | GCC |
| seq.229 | rep78 | 497 | GCC |
| seq.230 | rep52 | 497 | GCC |
| seq.231 | rep68 | 497 | GCC |
| seq.232 | rep40 | 497 | GCC |
| seq.233 | rep78 | 497 | CGA |
| seq.234 | rep52 | 497 | CGA |
| seq.235 | rep68 | 497 | CGA |
| seq.236 | rep40 | 497 | CGA |
| seq.237 | rep78 | 497 | CTC |
| seq.238 | rep52 | 497 | CTC |
| seq.239 | rep68 | 497 | CTC |
| seq.240 | rep40 | 497 | CTC |
| seq.241 | rep78 | 497 | TAC |
| seq.242 | rep52 | 497 | TAC |
| seq.243 | rep68 | 497 | TAC |
| seq.244 | rep40 | 497 | TAC |
| seq.245 | rep78 | 498 | GCT |
| seq.246 | rep52 | 498 | GCT |
| seq.247 | rep68 | 498 | GCT |
| seq.248 | rep40 | 498 | GCT |
| seq.249 | rep78 | 499 | GCC |
| seq.250 | rep52 | 499 | GCC |
| seq.251 | rep68 | 499 | GCC |
| seq.252 | rep40 | 499 | GCC |
| seq.253 | rep78 | 503 | GCG |
| seq.254 | rep52 | 503 | GCG |
| seq.255 | rep68 | 503 | GCG |
| seq.256 | rep40 | 503 | GCG |
| seq.257 | rep78 | 510 | GCA |
| seq.258 | rep52 | 510 | GCA |
| seq.259 | rep68 | 510 | GCA |
| seq.260 | rep40 | 510 | GCA |
| seq.261 | rep78 | 511 | GCA |
| seq.262 | rep52 | 511 | GCA |
| seq.263 | rep68 | 511 | GCA |
| seq.264 | rep40 | 511 | GCA |
| seq.265 | rep78 | 512 | GCT |
| seq.266 | rep52 | 512 | GCT |
| seq.267 | rep68 | 512 | GCT |
| seq.268 | rep40 | 512 | GCT |
| seq.269 | rep78 | 516 | GCG |
| seq.270 | rep52 | 516 | GCG |
| seq.271 | rep68 | 516 | GCG |
| seq.272 | rep40 | 516 | GCG |
| seq.273 | rep78 | 517 | GCT |
| seq.274 | rep52 | 517 | GCT |
| seq.275 | rep68 | 517 | GCT |
| seq.276 | rep40 | 517 | GCT |
| seq.277 | rep78 | 517 | AAC |
| seq.278 | rep52 | 517 | AAC |
| seq.279 | rep68 | 517 | AAC |
| seq.280 | rep40 | 517 | AAC |
| seq.281 | rep78 | 518 | GCA |
| seq.282 | rep52 | 518 | GCA |
| seq.283 | rep68 | 518 | GCA |
| seq.284 | rep40 | 518 | GCA |
| seq.285 | rep78 | 519 | GCG |
| seq.286 | rep52 | 519 | GCG |
| seq.287 | rep68 | 519 | GCG |
| seq.288 | rep40 | 519 | GCG |
| seq.289 | rep78 | 598 | GCA |
| seq.290 | rep52 | 598 | GCA |
| seq.291 | rep78 | 598 | GAC |

-continued

| | | | |
|---|---|---|---|
| seq.292 | rep52 | 598 | GAC |
| seq.293 | rep78 | 598 | AGC |
| seq.294 | rep52 | 598 | AGC |
| seq.295 | rep78 | 600 | GCG |
| seq.296 | rep52 | 600 | GCG |
| seq.297 | rep78 | 600 | CCG |
| seq.298 | rep52 | 600 | CCG |
| seq.299 | rep78 | 601 | GCA |
| seq.300 | rep52 | 601 | GCA |
| seq.301 | rep78 | 335 420 495 | GCT GCC GCC |
| seq.302 | rep52 | 335 420 495 | GCT GCC GCC |
| seq.303 | rep68 | 335 420 495 | GCT GCC GCC |
| seq.304 | rep40 | 335 420 495 | GCT GCC GCC |
| seq.305 | rep78 | 39 140 | GCA GCC |
| seq.306 | rep68 | 39 140 | GCA GCC |
| seq.307 | rep78 | 279 428 451 | GCC GCT GCC |
| seq.308 | rep52 | 279 428 451 | GCC GCT GCC |
| seq.309 | rep68 | 279 428 451 | GCC GCT GCC |
| seq.310 | rep40 | 279 428 451 | GCC GCT GCC |
| seq.311 | rep78 | 125 237 600 | GCG GCC GCG |
| seq.312 | rep52 | 125 237 600 | GCG GCC GCG |
| seq.313 | rep68 | 125 237 600 | GCG GCC GCG |
| seq.314 | rep40 | 125 237 600 | GCG GCC GCG |
| seq.315 | rep78 | 163 259 | GCT GCG |
| seq.316 | rep52 | 163 259 | GCT GCG |
| seq.317 | rep68 | 163 259 | GCT GCG |
| seq.318 | rep40 | 163 259 | GCT GCG |
| seq.319 | rep78 | 17 127 189 | GCG GCT GCG |
| seq.320 | rep68 | 17 127 189 | GCG GCT GCG |
| seq.321 | rep78 | 350 428 | GCT GCT |
| seq.322 | rep52 | 350 428 | GCT GCT |
| seq.323 | rep68 | 350 428 | GCT GCT |
| seq.324 | rep40 | 350 428 | GCT GCT |
| seq.325 | rep78 | 54 338 495 | GCC GCC GCC |
| seq.326 | rep52 | 54 338 495 | GCC GCC GCC |
| seq.327 | rep68 | 54 338 495 | GCC GCC GCC |
| seq.328 | rep40 | 54 338 495 | GCC GCC GCC |
| seq.329 | rep78 | 350 420 | GCT GCC |
| seq.330 | rep52 | 350 420 | GCT GCC |
| seq.331 | rep68 | 350 420 | GCT GCC |
| seq.332 | rep40 | 350 420 | GCT GCC |
| seq.333 | rep78 | 189 197 518 | GCG GCG GCA |
| seq.334 | rep52 | 189 197 518 | GCG GCG GCA |
| seq.335 | rep68 | 189 197 518 | GCG GCG GCA |
| seq.336 | rep40 | 189 197 518 | GCG GCG GCA |
| seq.337 | rep78 | 468 516 | GCC GCG |
| seq.338 | rep52 | 468 516 | GCC GCG |
| seq.339 | rep68 | 468 516 | GCC GCG |
| seq.340 | rep40 | 468 516 | GCC GCG |
| seq.341 | rep78 | 127 221 350 54 140 | GCT GCA GCT GCC GCC |
| seq.342 | rep52 | 127 221 350 54 140 | GCT GCA GCT GCC GCC |
| seq.343 | rep68 | 127 221 350 54 140 | GCT GCA GCT GCC GCC |
| seq.344 | rep40 | 127 221 350 54 140 | GCT GCA GCT GCC GCC |
| seq.345 | rep78 | 221 285 | GCA GCG |
| seq.346 | rep52 | 221 285 | GCA GCG |
| seq.347 | rep68 | 221 285 | GCA GCG |
| seq.348 | rep40 | 221 285 | GCA GCG |
| seq.349 | rep78 | 23 495 | GCT GCC |
| seq.350 | rep52 | 23 495 | GCT GCC |
| seq.351 | rep68 | 23 495 | GCT GCC |
| seq.352 | rep40 | 23 495 | GCT GCC |
| seq.353 | rep78 | 20 54 420 495 | GCC GCC GCC GCC |
| seq.354 | rep52 | 20 54 420 495 | GCC GCC GCC GCC |
| seq.355 | rep68 | 20 54 420 495 | GCC GCC GCC GCC |
| seq.356 | rep40 | 20 54 420 495 | GCC GCC GCC GCC |
| seq.357 | rep78 | 412 612 | GCC GCG |
| seq.358 | rep52 | 412 612 | GCC GCG |
| seq.359 | rep68 | 412 612 | GCC GCG |
| seq.360 | rep40 | 412 612 | GCC GCG |
| seq.361 | rep78 | 197 412 | GCG GCC |
| seq.362 | rep52 | 197 412 | GCG GCC |
| seq.363 | rep68 | 197 412 | GCG GCC |
| seq.364 | rep40 | 197 412 | GCG GCC |
| seq.365 | rep78 | 412 495 511 | GCC GCC GCA |
| seq.366 | rep52 | 412 495 511 | GCC GCC GCA |

-continued

| | | | |
|---|---|---|---|
| seq.367 | rep68 | 412 495 511 | GCC GCC GCA |
| seq.368 | rep40 | 412 495 511 | GCC GCC GCA |
| seq.369 | rep78 | 98 422 | GCC GCC |
| seq.370 | rep52 | 98 422 | GCC GCC |
| seq.371 | rep68 | 98 422 | GCC GCC |
| seq.372 | rep40 | 98 422 | GCC GCC |
| seq.373 | rep78 | 17 127 189 | GCG GCT GCG |
| seq.374 | rep68 | 17 127 189 | GCG GCT GCG |
| seq.375 | rep78 | 20 54 495 | GCC GCC GCC |
| seq.376 | rep52 | 20 54 495 | GCC GCC GCC |
| seq.377 | rep68 | 20 54 495 | GCC GCC GCC |
| seq.378 | rep40 | 20 54 495 | GCC GCC GCC |
| seq.379 | rep78 | 259 54 | GCG GCC |
| seq.380 | rep52 | 259 54 | GCG GCC |
| seq.381 | rep68 | 259 54 | GCG GCC |
| seq.382 | rep40 | 259 54 | GCG GCC |
| seq.383 | rep78 | 335 399 | GCT GCG |
| seq.384 | rep52 | 335 399 | GCT GCG |
| seq.385 | rep68 | 335 399 | GCT GCG |
| seq.386 | rep40 | 335 399 | GCT GCG |
| seq.387 | rep78 | 221 432 | GCA GCA |
| seq.388 | rep52 | 221 432 | GCA GCA |
| seq.389 | rep68 | 221 432 | GCA GCA |
| seq.390 | rep40 | 221 432 | GCA GCA |
| seq.391 | rep78 | 259 516 | GCG GCG |
| seq.392 | rep52 | 259 516 | GCG GCG |
| seq.393 | rep68 | 259 516 | GCG GCG |
| seq.394 | rep40 | 259 516 | GCG GCG |
| seq.395 | rep78 | 495 516 | GCC GCG |
| seq.396 | rep52 | 495 516 | GCC GCG |
| seq.397 | rep68 | 495 516 | GCC GCG |
| seq.398 | rep40 | 495 516 | GCC GCG |
| seq.399 | rep78 | 414 14 | GCT GCC |
| seq.400 | rep52 | 414 14 | GCT GCC |
| seq.401 | rep68 | 414 14 | GCT GCC |
| seq.402 | rep40 | 414 14 | GCT GCC |
| seq.403 | rep78 | 74 402 495 | GCG GCC GCC |
| seq.404 | rep52 | 74 402 495 | GCG GCC GCC |
| seq.405 | rep68 | 74 402 495 | GCG GCC GCC |
| seq.406 | rep40 | 74 402 495 | GCG GCC GCC |
| seq.407 | rep78 | 228 462 497 | GCC GCC GCC |
| seq.408 | rep52 | 228 462 497 | GCC GCC GCC |
| seq.409 | rep68 | 228 462 497 | GCC GCC GCC |
| seq.410 | rep40 | 228 462 497 | GCC GCC GCC |
| seq.411 | rep78 | 290 338 | GCG GCC |
| seq.412 | rep52 | 290 338 | GCG GCC |
| seq.413 | rep68 | 290 338 | GCG GCC |
| seq.414 | rep40 | 290 338 | GCG GCC |
| seq.415 | rep78 | 140 511 | GCC GCA |
| seq.416 | rep52 | 140 511 | GCC GCA |
| seq.417 | rep68 | 140 511 | GCC GCA |
| seq.418 | rep40 | 140 511 | GCC GCA |
| seq.419 | rep78 | 86 378 | GCG GCG |
| seq.420 | rep52 | 86 378 | GCG GCG |
| seq.421 | rep68 | 86 378 | GCG GCG |
| seq.422 | rep40 | 86 378 | GCG GCG |
| seq.423 | rep78 | 54 86 | GCC GCG |
| seq.424 | rep68 | 54 86 | GCC GCG |
| seq.425 | rep78 | 54 86 | GCC GCG |
| seq.426 | rep68 | 54 86 | GCC GCG |
| seq.427 | rep78 | 214 495 140 | GCG GCC GCC |
| seq.428 | rep52 | 214 495 140 | GCG GCC GCC |
| seq.429 | rep68 | 214 495 140 | GCG GCC GCC |
| seq.430 | rep40 | 214 495 140 | GCG GCC GCC |
| seq.431 | rep78 | 495 511 | GCC GCA |
| seq.432 | rep52 | 495 511 | GCC GCA |
| seq.433 | rep68 | 495 511 | GCC GCA |
| seq.434 | rep40 | 495 511 | GCC GCA |
| seq.435 | rep78 | 495 54 | GCC GCC |
| seq.436 | rep52 | 495 54 | GCC GCC |
| seq.437 | rep68 | 495 54 | GCC GCC |
| seq.438 | rep40 | 495 54 | GCC GCC |
| seq.439 | rep78 | 197 495 | GCG GCC |
| seq.440 | rep52 | 197 495 | GCG GCC |
| seq.441 | rep68 | 197 495 | GCG GCC |
| seq.442 | rep40 | 197 495 | GCG GCC |
| seq.443 | rep78 | 261 20 | GCC GCC |
| seq.444 | rep52 | 261 20 | GCC GCC |
| seq.445 | rep68 | 261 20 | GCC GCC |

-continued

```
seq.446  rep40      261  20            GCC GCC
seq.447  rep78       54  20            GCC GCC
seq.448  rep68       54  20            GCC GCC
seq.449  rep78      197 420            GCG GCC
seq.450  rep52      197 420            GCG GCC
seq.451  rep68      197 420            GCG GCC
seq.452  rep40      197 420            GCG GCC
seq.453  rep78       54 338 495        GCC GCC GCC
seq.454  rep52       54 338 495        GCC GCC GCC
seq.455  rep68       54 338 495        GCC GCC GCC
seq.456  rep40       54 338 495        GCC GCC GCC
seq.457  rep78      197 427            GCG GCG
seq.458  rep52      197 427            GCG GCG
seq.459  rep68      197 427            GCG GCG
seq.460  rep40      197 427            GCG GCG
seq.461  rep78       54 228 370 387    GCC GCC GCC GCG
seq.462  rep52       54 228 370 387    GCC GCC GCC GCG
seq.463  rep68       54 228 370 387    GCC GCC GCC GCG
seq.464  rep40       54 228 370 387    GCC GCC GCC GCG
seq.465  rep78      221 289            GCA GCC
seq.466  rep52      221 289            GCA GCC
seq.467  rep68      221 289            GCA GCC
seq.468  rep40      221 289            GCA GCC
seq.469  rep78       54 163            GCC GCT
seq.470  rep68       54 163            GCC GCT
seq.471  rep78      341 407 420        GCC GCC GCC
seq.472  rep52      341 407 420        GCC GCC GCC
seq.473  rep68      341 407 420        GCC GCC GCC
seq.474  rep40      341 407 420        GCC GCC GCC
seq.475  rep78       54 228            GCC GCC
seq.476  rep52       54 228            GCC GCC
seq.477  rep68       54 228            GCC GCC
seq.478  rep40       54 228            GCC GCC
seq.479  rep78       96 125 511        GCA GCG GCA
seq.480  rep52       96 125 511        GCA GCG GCA
seq.481  rep68       96 125 511        GCA GCG GCA
seq.482  rep40       96 125 511        GCA GCG GCA
seq.483  rep78       54 163            GCC GCT
seq.484  rep68       54 163            GCC GCT
seq.485  rep78      197 420            GCG GCC
seq.486  rep52      197 420            GCG GCC
seq.487  rep68      197 420            GCG GCC
seq.488  rep40      197 420            GCG GCC
seq.489  rep78      334 428 499        GCG GCT GCC
seq.490  rep52      334 428 499        GCG GCT GCC
seq.491  rep68      334 428 499        GCG GCT GCC
seq.492  rep40      334 428 499        GCG GCT GCC
seq.493  rep78      197 414            GCG GCT
seq.494  rep52      197 414            GCG GCT
seq.495  rep68      197 414            GCG GCT
seq.496  rep40      197 414            GCG GCT
seq.497  rep78       30  54 127        GCG GCC GCT
seq.498  rep68       30  54 127        GCG GCC GCT
seq.499  rep78       29 260            GCG GCG
seq.500  rep52       29 260            GCG GCG
seq.501  rep68       29 260            GCG GCG
seq.502  rep40       29 260            GCG GCG
seq.503  rep78        4 484            GCT GCC
seq.504  rep52        4 484            GCT GCC
seq.505  rep68        4 484            GCT GCC
seq.506  rep40        4 484            GCT GCC
seq.507  rep78      258 124 132        GCC GCC GCC
seq.508  rep52      258 124 132        GCC GCC GCC
seq.509  rep68      258 124 132        GCC GCC GCC
seq.510  rep40      258 124 132        GCC GCC GCC
seq.511  rep78      231 497            GCC GCC
seq.512  rep52      231 497            GCC GCC
seq.513  rep68      231 497            GCC GCC
seq.514  rep40      231 497            GCC GCC
seq.515  rep78      221 258            GCA GCC
seq.516  rep52      221 258            GCA GCC
seq.517  rep68      221 258            GCA GCC
seq.518  rep40      221 258            GCA GCC
seq.519  rep78      234 264 326        GCG GCG GCC
seq.520  rep52      234 264 326        GCG GCG GCC
seq.521  rep68      234 264 326        GCG GCG GCC
seq.522  rep40      234 264 326        GCG GCG GCC
seq.523  rep78      153 398            AGC GCG
seq.524  rep52      153 398            AGC GCG
```

-continued

| Sequence | | aa position | | codon | |
|---|---|---|---|---|---|
| seq.525 | rep68 | 153 | 398 | AGC | GCG |
| seq.526 | rep40 | 153 | 398 | AGC | GCG |
| seq.527 | rep78 | 53 | 216 | GCG | GCC |
| seq.528 | rep68 | 53 | 216 | GCG | GCC |
| seq.529 | rep78 | 22 | 382 | GCT | GCG |
| seq.530 | rep52 | 22 | 382 | GCT | GCG |
| seq.531 | rep68 | 22 | 382 | GCT | GCG |
| seq.532 | rep40 | 22 | 382 | GCT | GCG |
| seq.533 | rep78 | 231 | 411 | GCC | GCA |
| seq.534 | rep52 | 231 | 411 | GCC | GCA |
| seq.535 | rep68 | 231 | 411 | GCC | GCA |
| seq.536 | rep40 | 231 | 411 | GCC | GCA |
| seq.537 | rep78 | 59 | 305 | GCG | GCC |
| seq.538 | rep52 | 59 | 305 | GCG | GCC |
| seq.539 | rep68 | 59 | 305 | GCG | GCC |
| seq.540 | rep40 | 59 | 305 | GCG | GCC |
| seq.541 | rep78 | 53 | 231 | GCG | GCC |
| seq.542 | rep52 | 53 | 231 | GCG | GCC |
| seq.543 | rep68 | 53 | 231 | GCG | GCC |
| seq.544 | rep40 | 53 | 231 | GCG | GCC |
| seq.545 | rep78 | 258 | 498 | GCC | GCT |
| seq.546 | rep52 | 258 | 498 | GCC | GCT |
| seq.547 | rep68 | 258 | 498 | GCC | GCT |
| seq.548 | rep40 | 258 | 498 | GCC | GCT |
| seq.549 | rep78 | 88 | 231 | GCC | GCC |
| seq.550 | rep52 | 88 | 231 | GCC | GCC |
| seq.551 | rep68 | 88 | 231 | GCC | GCC |
| seq.552 | rep40 | 88 | 231 | GCC | GCC |
| seq.553 | rep78 | 101 | 363 | GCA | GCC |
| seq.554 | rep52 | 101 | 363 | GCA | GCC |
| seq.555 | rep68 | 101 | 363 | GCA | GCC |
| seq.556 | rep40 | 101 | 363 | GCA | GCC |
| seq.557 | rep78 | 354 | 132 | GCC | GCC |
| seq.558 | rep52 | 354 | 132 | GCC | GCC |
| seq.559 | rep68 | 354 | 132 | GCC | GCC |
| seq.560 | rep40 | 354 | 132 | GCC | GCC |
| seq.561 | rep78 | 10 | 132 | GCG | GCC |
| seq.562 | rep68 | 10 | 132 | GCG | GCC |

DNA Sequences

| Sequence | aa position | codon |
|---|---|---|
| seq.563 | 4 | GCT |
| seq.564 | 10 | GCG |
| seq.565 | 20 | GCC |
| seq.566 | 22 | GCT |
| seq.567 | 29 | GCG |
| seq.568 | 38 | GCG |
| seq.569 | 39 | GCA |
| seq.570 | 53 | GCT |
| seq.571 | 59 | GCG |
| seq.572 | 64 | GCT |
| seq.573 | 74 | GCG |
| seq.574 | 86 | GCG |
| seq.575 | 88 | GCC |
| seq.576 | 101 | GCA |
| seq.577 | 124 | GCC |
| seq.578 | 125 | GCG |
| seq.579 | 127 | GCT |
| seq.580 | 132 | GCC |
| seq.581 | 140 | GCC |
| seq.582 | 161 | GCC |
| seq.583 | 163 | GCT |
| seq.584 | 175 | GCT |
| seq.585 | 193 | GCG |
| seq.586 | 196 | GCC |
| seq.587 | 197 | GCC |
| seq.588 | 221 | GCA |
| seq.589 | 228 (Rep78/68) | GCG |
| | 228 (Rep52) | GCG |
| | 228 (Rep 40) | GCG |
| seq.590 | 231 (Rep78/68) | GCC |
| | 231 (Rep 52) | GCC |
| | 231 (Rep 40) | GCC |
| seq.591 | 234 (Rep78/68) | GCG |
| | 234 (Rep 52) | GCG |
| | 234 (Rep 40) | GCG |

-continued

| | | |
|---|---|---|
| seq.592 | 237 (Rep78/68) | GCC |
| | 237 (Rep 52) | GCC |
| | 237 (Rep 40) | GCC |
| seq.593 | 250 (Rep78/68) | GCC |
| | 250 | GCC |
| | 250 | GCC |
| seq.594 | 258 (Rep78/68) | GCC |
| | 258 | GCC |
| | 258 | GCC |
| seq.595 | 260 (Rep78/68) | GCG |
| | 260 | GCG |
| | 260 | GCG |
| seq.596 | 263 (Rep78/68) | GCC |
| | 263 | GCC |
| | 263 | GCC |
| seq.597 | 264 (Rep78/68) | GCG |
| | 264 | GCG |
| | 264 | GCG |
| seq.598 | 334 (Rep78/68) | GCG |
| | 334 | GCG |
| | 334 | GCG |
| seq.599 | 335 (Rep78/68) | GCT |
| | 335 | GCT |
| | 335 | GCT |
| seq.600 | 337 (Rep78/68) | GCT |
| | 337 | GCT |
| | 337 | GCT |
| seq.601 | 341 (Rep78/68) | GCC |
| | 341 | GCC |
| | 341 | GCC |
| seq.602 | 342 (Rep78/68) | GCC |
| | 342 | GCC |
| | 342 | GCC |
| seq.603 | 347 (Rep78/68) | GCA |
| | 347 | GCA |
| | 347 | GCA |
| seq.604 | 350 (Rep78/68) | AAT |
| | 350 | AAT |
| | 350 | AAT |
| seq.605 | 350 (Rep78/68) | GCT |
| | 350 | GCT |
| | 350 | GCT |
| seq.606 | 354 (Rep78/68) | GCC |
| | 354 | GCC |
| | 354 | GCC |
| seq.607 | 363 (Rep78/68) | GCC |
| | 363 | GCC |
| | 363 | GCC |
| seq.608 | 364 (Rep78/68) | GCT |
| | 364 | GCT |
| | 364 | GCT |
| seq.609 | 367 (Rep78/68) | GCC |
| | 367 | GCC |
| | 367 | GCC |
| seq.610 | 370 (Rep78/68) | GCC |
| | 370 | GCC |
| | 370 | GCC |
| seq.611 | 376 (Rep78/68) | GCG |
| | 376 | GCG |
| | 376 | GCG |
| seq.612 | 381 (Rep78/68) | GCG |
| | 381 | GCG |
| | 381 | GCG |
| seq.613 | 382 (Rep78/68) | GCG |
| | 382 | GCG |
| | 382 | GCG |
| seq.614 | 389 (Rep78/68) | GCG |
| | 389 | GCG |
| | 389 | GCG |
| seq.615 | 407 (Rep78/68) | GCC |
| | 407 | GCC |
| | 407 | GCC |
| seq.616 | 411 (Rep78/68) | GCA |
| | 411 | GCA |
| | 411 | GCA |
| seq.617 | 414 (Rep78/68) | GCT |
| | 414 | GCT |
| | 414 | GCT |

-continued

| | | | |
|---|---|---|---|
| seq.618 | 420 | (Rep78/68) | GCT |
| | 420 | | GCT |
| | 420 | | GCT |
| seq.619 | 421 | (Rep78/68) | GCC |
| | 421 | | GCC |
| | 421 | | GCC |
| seq.620 | 422 | (Rep78/68) | GCC |
| | 422 | | GCC |
| | 422 | | GCC |
| seq.621 | 424 | (Rep78/68) | GCG |
| | 424 | | GCG |
| | 424 | | GCG |
| seq.622 | 428 | (Rep78/68) | GCT |
| | 428 | | GCT |
| | 428 | | GCT |
| seq.623 | 429 | (Rep78/68) | GCC |
| | 429 | | GCC |
| | 429 | | GCC |
| seq.624 | 438 | (Rep78/68) | GCG |
| | 438 | | GCG |
| | 438 | | GCG |
| seq.625 | 440 | (Rep78/68) | GCG |
| | 440 | | GCG |
| | 440 | | GCG |
| seq.626 | 451 | (Rep78/68) | GCC |
| | 451 | | GCC |
| | 451 | | GCC |
| seq.627 | 460 | (Rep78/68) | GCG |
| | 460 | | GCG |
| | 460 | | GCG |
| seq.628 | 462 | (Rep78/68) | GCC |
| | 462 | | GCC |
| | 462 | | GCC |
| seq.629 | 462 | (Rep78/68) | ATA |
| | 462 | | ATA |
| | 462 | | ATA |
| seq.630 | 484 | (Rep78/68) | GCC |
| | 484 | | GCC |
| | 484 | | GCC |
| seq.631 | 488 | (Rep78/68) | GCG |
| | 488 | | GCG |
| | 488 | | GCG |
| seq.632 | 495 | (Rep78/68) | GCC |
| | 495 | | GCC |
| | 495 | | GCC |
| seq.633 | 497 | (Rep78/68) | GCC |
| | 497 | | GCC |
| | 497 | | GCC |
| seq.634 | 497 | (Rep78/68) | CGA |
| | 497 | | CGA |
| | 497 | | CGA |
| seq.635 | 497 | (Rep78/68) | CTC |
| | 497 | | CTC |
| | 497 | | CTC |
| seq.636 | 497 | (Rep78/68) | TAC |
| | 497 | | TAC |
| | 497 | | TAC |
| seq.637 | 498 | (Rep78/68) | GCT |
| | 498 | | GCT |
| | 498 | | GCT |
| seq.638 | 499 | (Rep78/68) | GCC |
| | 499 | | GCC |
| | 499 | | GCC |
| seq.639 | 503 | (Rep78/68) | GCG |
| | 503 | | GCG |
| | 503 | | GCG |
| seq.640 | 510 | (Rep78/68) | GCA |
| | 510 | | GCA |
| | 510 | | GCA |
| seq.641 | 511 | (Rep78/68) | GCA |
| | 511 | | GCA |
| | 511 | | GCA |
| seq.642 | 512 | (Rep78/68) | GCT |
| | 512 | | GCT |
| | 512 | | GCT |
| seq.643 | 516 | (Rep78/68) | GCG |
| | 516 | | GCG |
| | 516 | | GCG |

-continued

| | | |
|---|---|---|
| seq.644 | 517 (Rep78/68) | GCT |
| | 517 | GCT |
| | 517 | GCT |
| seq.645 | 517 (Rep78/68) | AAC |
| | 517 | AAC |
| | 517 | AAC |
| seq.646 | 518 (Rep78/68) | GCA |
| | 518 | GCA |
| | 518 | GCA |
| seq.647 | 519 (Rep78/68) | GCG |
| | 519 | GCG |
| | 519 | GCG |
| seq.648 | 598 (Rep78/68) | GCA |
| seq.649 | 600 (Rep78/68) | GCG |
| seq.650 | 601 (Rep78/68) | GCA |
| seq.651 | 335 420 495 | GCT GCC GCC |
| | 335 420 495 | GCT GCC GCC |
| | 335 420 495 | GCT GCC GCC |
| seq.652 | 39 140 | GCA GCC |
| seq.653 | 279 428 451 | GCC GCT GCC |
| | 279 428 451 | GCC GCT GCC |
| | 279 428 451 | GCC GCT GCC |
| seq.654 | 125 237 600 | GCG GCC GCG |
| | 125 237 600 | GCG GCC GCG |
| | 125 237 600 | GCG GCC GCG |
| seq.655 | 163 259 | GCT GCG |
| | 163 259 | GCT GCG |
| | 163 259 | GCT GCG |
| seq.656 | 17 127 189 | GCG GCT GCG |
| seq.657 | 350 428 | GCT GCT |
| | 350 428 | GCT GCT |
| | 350 428 | GCT GCT |
| seq.658 | 54 338 495 | GCC GCC GCC |
| | 54 338 495 | GCC GCC GCC |
| | 54 338 495 | GCC GCC GCC |
| seq.659 | 350 420 | GCT GCC |
| | 350 420 | GCT GCC |
| | 350 420 | GCT GCC |
| seq.660 | 189 197 518 | GCG GCG GCA |
| | 189 197 518 | GCG GCG GCA |
| | 189 197 518 | GCG GCG GCA |
| seq.661 | 468 516 | GCC GCG |
| | 468 516 | GCC GCG |
| | 468 516 | GCC GCG |
| seq.662 | 127 221 350 54 140 | GCT GCA GCT GCC GCC |
| | 127 221 350 54 140 | GCT GCA GCT GCC GCC |
| | 127 221 350 54 140 | GCT GCA GCT GCC GCC |
| seq.663 | 221 285 | GCA GCG |
| | 221 285 | GCA GCG |
| | 221 285 | GCA GCG |
| seq.664 | 23 495 | GCT GCC |
| | 23 495 | GCT GCC |
| | 23 495 | GCT GCC |
| seq.665 | 20 54 420 495 | GCC GCC GCC GCC |
| | 20 54 420 495 | GCC GCC GCC GCC |
| | 20 54 420 495 | GCC GCC GCC GCC |
| seq.666 | 412 612 | GCC GCG |
| | 412 612 | GCC GCG |
| | 412 612 | GCC GCG |
| seq.667 | 197 412 | GCG GCC |
| | 197 412 | GCG GCC |
| | 197 412 | GCG GCC |
| seq.668 | 412 495 511 | GCC GCC GCA |
| | 412 495 511 | GCC GCC GCA |
| | 412 495 511 | GCC GCC GCA |
| seq.669 | 98 422 | GCC GCC |
| | 98 422 | GCC GCC |
| | 98 422 | GCC GCC |
| seq.670 | 17 127 189 | GCG GCT GCG |
| seq.671 | 20 54 495 | GCC GCC GCC |
| | 20 54 495 | GCC GCC GCC |
| | 20 54 495 | GCC GCC GCC |
| seq.672 | 54 163 | GCC GCT |
| seq.673 | 259 54 | GCG GCC |
| | 259 54 | GCG GCC |
| | 259 54 | GCG GCC |
| seq.674 | 335 399 | GCT GCG |
| | 335 399 | GCT GCG |
| | 335 399 | GCT GCG |

-continued

| | | |
|---|---|---|
| seq.675 | 221 432 | GCA GCA |
| | 221 432 | GCA GCA |
| | 221 432 | GCA GCA |
| seq.676 | 259 516 | GCG GCG |
| | 259 516 | GCG GCG |
| | 259 516 | GCG GCG |
| seq.677 | 495 516 | GCC GCG |
| | 495 516 | GCC GCG |
| | 495 516 | GCC GCG |
| seq.678 | 414 14 | GCT GCC |
| | 414 14 | GCT GCC |
| | 414 14 | GCT GCC |
| seq.679 | 74 402 495 | GCG GCC GCC |
| | 74 402 495 | GCG GCC GCC |
| | 74 402 495 | GCG GCC GCC |
| seq.680 | 228 462 497 | GCC GCC GCC |
| | 228 462 497 | GCC GCC GCC |
| | 228 462 497 | GCC GCC GCC |
| seq.681 | 290 338 | GCG GCC |
| | 290 338 | GCG GCC |
| | 290 338 | GCG GCC |
| seq.682 | 140 511 | GCC GCA |
| | 140 511 | GCC GCA |
| | 140 511 | GCC GCA |
| seq.683 | 86 378 | GCG GCG |
| | 86 378 | GCG GCG |
| | 86 378 | GCG GCG |
| seq.684 | 54 86 | GCC GCG |
| | 54 86 | GCC GCG |
| | 54 86 | GCC GCG |
| seq.685 | 214 495 140 | GCG GCC GCC |
| | 214 495 140 | GCG GCC GCC |
| | 214 495 140 | GCG GCC GCC |
| seq.686 | 495 511 | GCC GCA |
| | 495 511 | GCC GCA |
| | 495 511 | GCC GCA |
| seq.687 | 495 54 | GCC GCC |
| | 495 54 | GCC GCC |
| | 495 54 | GCC GCC |
| seq.688 | 197 495 | GCG GCC |
| | 197 495 | GCG GCC |
| | 197 495 | GCG GCC |
| seq.689 | 261 20 | GCC GCC |
| | 261 20 | GCC GCC |
| | 261 20 | GCC GCC |
| seq.690 | 54 20 | GCC GCC |
| seq.691 | 197 420 | GCG GCC |
| | 197 420 | GCG GCC |
| | 197 420 | GCG GCC |
| seq.692 | 54 338 495 | GCC GCC GCC |
| | 54 338 495 | GCC GCC GCC |
| | 54 338 495 | GCC GCC GCC |
| seq.693 | 197 427 | GCG GCG |
| | 197 427 | GCG GCG |
| | 197 427 | GCG GCG |
| seq.694 | 54 228 370 387 | GCC GCC GCC GCG |
| | 54 228 370 387 | GCC GCC GCC GCG |
| | 54 228 370 387 | GCC GCC GCC GCG |
| seq.695 | 221 289 | GCA GCC |
| | 221 289 | GCA GCC |
| | 221 289 | GCA GCC |
| seq.696 | 54 163 | GCC GCT |
| | 54 163 | GCC GCT |
| seq.697 | 341 407 420 | GCC GCC GCC |
| | 341 407 420 | GCC GCC GCC |
| | 341 407 420 | GCC GCC GCC |
| seq.698 | 54 228 | GCC GCC |
| | 54 228 | GCC GCC |
| | 54 228 | GCC GCC |
| seq.699 | 96 125 511 | GCA GCG GCA |
| | 96 125 511 | GCA GCG GCA |
| | 96 125 511 | GCA GCG GCA |
| seq.700 | 197 420 | GCG GCC |
| | 197 420 | GCG GCC |
| | 197 420 | GCG GCC |
| seq.701 | 334 428 499 | GCG GCT GCC |
| | 334 428 499 | GCG GCT GCC |
| | 334 428 499 | GCG GCT GCC |

-continued

| | | |
|---|---|---|
| seq.702 | 197 414 | GCG GCT |
| | 197 414 | GCG GCT |
| | 197 414 | GCG GCT |
| seq.703 | 30 54 127 | GCG GCC GCT |
| seq.704 | 29 260 | GCG GCG |
| | 29 260 | GCG GCG |
| | 29 260 | GCG GCG |
| seq.706 | 4 484 | GCT GCC |
| | 4 484 | GCT GCC |
| | 4 484 | GCT GCC |
| seq.707 | 258 124 132 | GCC GCC GCC |
| | 258 124 132 | GCC GCC GCC |
| | 258 124 132 | GCC GCC GCC |
| seq.708 | 231 497 | GCC GCC |
| | 231 497 | GCC GCC |
| | 231 497 | GCC GCC |
| seq.709 | 221 258 | GCA GCC |
| | 221 258 | GCA GCC |
| | 221 258 | GCA GCC |
| seq.710 | 234 264 326 | GCG GCG GCC |
| | 234 264 326 | GCG GCG GCC |
| | 234 264 326 | GCG GCG GCC |
| seq.711 | 153 398 | AGC GCG |
| | 153 398 | AGC GCG |
| | 153 398 | AGC GCG |
| seq.712 | 53 216 | GCG GCC |
| seq.713 | 22 382 | GCT GCG |
| | 22 382 | GCT GCG |
| | 22 382 | GCT GCG |
| seq.714 | 231 411 | GCC GCA |
| | 231 411 | GCC GCA |
| | 231 411 | GCC GCA |
| seq.715 | 59 305 | GCG GCC |
| | 59 305 | GCG GCC |
| | 59 305 | GCG GCC |
| seq.716 | 53 231 | GCG GCC |
| | 53 231 | GCG GCC |
| | 53 231 | GCG GCC |
| seq.717 | 258 498 | GCC GCT |
| | 258 498 | GCC GCT |
| | 258 498 | GCC GCT |
| seq.718 | 88 231 | GCC GCC |
| | 88 231 | GCC GCC |
| | 88 231 | GCC GCC |
| seq.719 | 101 363 | GCA GCC |
| | 101 363 | GCA GCC |
| | 101 363 | GCA GGC |
| seq.720 | 354 132 | GCC GCC |
| | 354 132 | GCC GCC |
| | 354 132 | GCC GCC |
| seq.726 | 598 | GAC |
| seq.727 | 598 | AGC |
| seq.728 | 600 | CCG |

The above nucleic acid molecules are provided in plasmids, which are introduced into cells to produce the encoded proteins. The analysis revealed the amino acid positions that affect Rep proteins activities. Changes of amino acids at any of the hit positions result in altered protein activity. Hit positions are numbered and referenced starting from amino acid 1 (nucleotide 321 in AAV-2 genome), also codon 1 of the protein Rep78 coding sequence under control of p5 promoter of AAV-2: 4, 20, 22, 29, 32, 38, 39, 54, 59, 124, 125, 127, 132, 140, 161, 163, 193, 196, 197, 221, 228, 231, 234, 258, 260, 263, 264, 334, 335, 337, 342, 347, 350, 354, 363, 364, 367, 370, 376, 381, 389, 407, 411, 414, 420, 421, 422, 424, 428, 438, 440, 451, 460, 462, 484, 488, 495, 497, 498, 499, 503, 511, 512, 516, 517, 518, 542, 548, 598, 600 and 601. The encoded Rep78, Rep68, Rep 52 and Rep 40 proteins and rAAV encoding the mutant proteins are provided. The corresponding nucleic acid molecules, Rep proteins, rAAV and cells containing the nucleic acid molecules or rAAV in which the native proteins are from other AAV serotypes, including, but are not limited to, AAV-1, AAV-3, AAV-3B, AAV-4, AAV-5 and AAV-6.

Other hit positions identified include: 10, 64, 74, 86, 88, 101, 175, 237, 250, 334, 429 and 519.

Also provided are nucleic acid molecules, the rAAV, and the encoded proteins in which the native amino acid at each hit position is replaced with another amino acid, or is deleted, or contains additional amino acids at or adjacent to or near the hit positions. In particular the following nucleic acid molecules and rAAV that encode proteins containing the following amino acid replacements or combinations thereof: T by N at Hit position 350; T by I at Hit position 462; P by R at Hit position 497; P by L at Hit position 497; P by Y at Hit position 497; T by N at Hit position 517; L by S at hit position 542; R by S at hit position 548; G by D at Hit position 598; G by S at Hit position 598; V by P at Hit position 600; in order to increase Rep proteins activities in terms on AAV or rAAV productivity. The corresponding nucleic acid molecules, recombinant Rep proteins from the other serotypes and the resulting rAAV are also provided (see FIG. 5 and the above Table for the corresponding position in AAV-1, AAV-3, AAV-3B, AAV-4, AAV-5 and AAV-6).

Mutant adeno-associated virus (AAV) Rep proteins and viruses encoding such proteins that include mutations at one or more of residues 64, 74, 88, 175, 237, 250 and 429, where residue 1 corresponds to residue 1 of the Rep78 protein encoded by nucleotides 321-323 of the AAV-2 genome, and where the amino acids are replaced as follows: L by A at position 64; P by A at position 74; Y by A at position 88; Y by A at position 175; T by A at position 237; T by A at position 250; D by A at position 429 are provided. Nucleic acid molecules encoding these viruses and the mutant proteins are also provided.

Also provided are nucleic acid molecules produced from any of the above-noted nucleic acid molecules by any directed evolution method, including, but are not limited to, re-synthesis, mutagenesis, recombination and gene shuffling and any way by combining any combination of the molecules, i.e., one, two by one, two by two, . . . n by n, where n is the number of molecules to be combined (i.e., combining all together). The resulting recombinant AAV and encoded proteins are also provided.

Also provided are nucleic acid molecule in which additional amino acids surrounding each hit, such as one, two, three . . . ten or more, amino acids are systematically replaced, such that the resulting Rep protein(s) has increased or decreased activity. Increased activity as assessed by increased recombinant virus production in suitable cells is of particular interest for production of recombinant viruses for use, for example, in gene therapy.

Also provided are combinations of the above noted mutants in which several of the noted amino acids are changed and optionally additional amino acids surrounding each hit, such as one, two, three . . . ten or more, are replaced.

The nucleic acid molecules of SEQ ID Nos. 563-725 and the encoded proteins (SEQ ID Nos. 1-562 and 726-728) are also provided. Recombinant AAV and cells containing the encoding nucleic acids are provided, as are the AAV produced upon replication of the AAV in the cells.

Methods of in vivo or in vitro production of AAV or rAAV using any of the above nucleic acid molecules or cells for intracellular expression of rep proteins or the rep gene mutants are provided. In vitro production is effected using cell free systems, expression or replication and/or virus assembly. In vivo production is effected in mammalian cells that also contain any requisite cis acting elements required for packaging.

Also provided are nucleic acid molecules and rAAV (any serotype) in which position 630 (or the corresponding position in another serotype; see FIG. 5 and the table above) has been changed. Changes at this position and the region around it lead to changes in the activity or in the quantities of the Rep or Cap proteins and/or the amount of AAV or rAAV produced in cells transduced with AAV encoding such mutants. Such mutations include tgc to gcg change (SEQ ID No. 721). Mutations at any position surrounding the codon position 630 that increase or decrease the Rep or Cap proteins quantities or activities are also provided. Methods using the rAAV (any serotype) that contain nucleic acid molecules with a mutation at position 630 or within 1, 2, 3 . . . 10 or more bases thereof for the intracellular expression of rep proteins or the rep gene mutants described herein, for the production of AAV or rAAV (either in vitro, in vivo or ex vivo) are provided. In vitro methods include cell free systems, expression or replication and/or virus assembly.

Also provided are rAAV (and other serotypes with corresponding changes) and nucleic acid molecules encoding an amino acid replacement by N at Hit position 350 of AAV-1, AAV-3, AAV-3B, AAV-4 and AAV-6 or at Hit position 346 of AAV-5; by I at Hit position 462 of AAV-1, AAV-3, AAV-3B, AAV-4 and AAV-6 or at Hit position 458 of AAV-5; by either R, L or Y at Hit position 497 of AAV-1, AAV-3, AAV-3B, AAV-4 and AAV-6 or at Hit position 493 of AAV-5; by N at Hit position 517 of AAV-1, AAV-3, AAV-3B, AAV-4 and AAV-6 or at Hit position 535 of AAV-5; by S at hit position 543 of AAV-1 and AAV-6 or at hit position 542 of AAV-3, AAV-3B and AAV-4 or at hit position 561 of AAV-5; by S at hit position 549 of AAV-1 and AAV-6 or at hit position 548 of AAV-3, AAV-3B and AAV-4 or at hit position 567 of AAV-5; by either D or S at Hit position 599 of AAV-1, AAV-4 and AAV-6 or at Hit position 600 of AAV-3 and AAV-3B; by P at Hit position 602 of AAV-1, AAV-4 and AAV-6 or at hit position 603 of AAV-3 and AAV-3B or at hit position 589 of AAV-5 in order to increase Rep proteins activities as assessed by AAV or rAAV productivity. Methods using such AAV for expression of the encoded proteins and production of AAV are also provided.

Since modifications will be apparent to those of skill in this art, it is intended that this invention be limited only by the scope of the appended claims.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07647184B2). An electronic copy of the "Sequence Listing" will also be available from the USPTO upon request and payment of the fee set forth in 37 CFR 1.19(b)(3).

---

What is claimed is:

1. A high throughput process for the identification of a protein that differs in a predetermined property or activity from a target protein, comprising:
   (a) producing a plurality of separate sets of nucleic acid molecules that encode modified forms of a target protein, wherein:
      the nucleic acid molecules in each set are produced by changing one codon in the target protein to a pre-selected codon, whereby the nucleic acid molecules in each set encode proteins that differ from the encoded proteins in another set by one amino acid;
      a sufficient number of sets of nucleic acid molecules are produced so that each encoded amino acid residue in the encoded protein is replaced with a pre-selected amino acid along the full-length of the encoded protein so that all positions along the full-length of the protein are individually modified for screening, and each nucleic acid molecule encodes a protein that differs by one amino acid from the target protein; and all nucleic acid molecules in a set encode the same modified protein;

(b) individually introducing each set of nucleic acid molecules into host cells to produce an addressable array of host cells, whereby the identity of each set of nucleic acid molecules in host cells of each locus in the array is known, wherein the cells of each locus of the addressable array contain the same modified nucleic acid molecules;

(c) expressing the encoded proteins, whereby a plurality of separate sets of proteins encoded by the nucleic acid molecules are produced and all positions along the full-length of the protein are individually modified, wherein:

all of the encoded proteins in each set have the same modification; and the proteins in each set differ from the proteins in another set by one amino acid and from the target protein by one amino acid; and (d) individually screening each set of encoded proteins to identify one or more proteins that have a predetermined property that differs from the target, wherein:

each identified protein is designated a hit;

each hit contains a mutation designated a hit position; and the predetermined property or activity is selected from among a chemical, a physical and a biological property or an activity of the target protein;

(e) modifying the nucleic acid molecules that encode the hits to produce sets of nucleic acid molecules that encode modified hits, wherein:

the modified hits are produced by systematically and individually replacing each codon that is a hit position with a codon encoding another amino acid to produce nucleic acid molecules each differing by at least one codon and encoding modified hits; each set of nucleic acid molecules is individually designed and synthesized, whereby:

a sufficient number of sets are produced to produce encoded proteins in which every hit is separately replaced with all other amino acids, and the encoded protein in each set differs from the encoded protein each other set and the target protein by one amino acid;

the identity of each set of nucleic acid molecules in host cells of each locus in the array is known and wherein the cells of each locus of the addressable array contain the same modified nucleic acid molecules;

(f) separately introducing each set of nucleic molecules that encodes the modified hits into cells to produce an addressable array of cells, whereby the identity of each encoded protein at each locus in the array is known and expressing the protein encoded by the introduced nucleic acid molecules; and (g) screening all cells that contain the expressed protein by individually screening each set of cells that contains the nucleic acid molecules that encode the modified hits to identify one or more nucleic acid molecules that encode (s) a protein or the coded protein that has/have the pre-determined property or activity that differs from the target protein and has properties that differ from the original hits, wherein each such protein is designated a lead, wherein each and all of steps (a)-(g) are performed in an automated high throughput format whereby each molecule is individually designed, produced, screened and tested in the high throughput format.

2. The process of claim 1, wherein each set of nucleic acid molecules is individually designed and synthesized.

3. The process of claim 2, wherein each set is deposited at a locus on a solid support configured as an array.

4. The process of claim 1, wherein the array comprises a solid support with loci for containing or retaining cells; and each locus contains one set of cells.

5. The process of claim 1, wherein the array comprises a solid support with wells for containing or retaining cells; and each well contains one set of cells.

6. The process of claim 1, wherein the nucleic acid molecules comprise viral vectors; and the cells are eukaryotic cells that are transduced with the vectors.

7. The process of claim 1, wherein the nucleic acid molecules comprise plasmids and the cells are bacterial cells.

8. The method of claim 1, wherein the pre-selected amino acid is selected from among Ala (A), Ser (S), Pro (P) and Gly (G).

9. The method of claim 1, wherein the pre-selected amino acid is selected from among Arg (R), Asn (N), Asp (D), Cys (C), Gln (O), Glu (E), His (H), Ile (I), Leu (L), Lys (K), Met (M), Phe (F), Thr (T), Trp (W), Tyr (Y) and Val (V).

10. The method of claim 1, further comprising:

recombining the nucleic acid molecules encoding the leads;

introducing those nucleic acid molecules into cells; and screening the cells to identify nucleic acid molecules that encode new leads that exhibit a greater change in a property or in an activity than the leads identified in claim 1.

11. The method of claim 10, wherein the recombining is two, three or more up to all of the nucleic acids encoding the leads.

12. The method of claim 10, wherein the recombining is effected by a method selected from among nucleic acid shuffling, recombination, site-directed or random mutagenesis and de novo synthesis.

13. The process of claim 1, wherein the predetermined property or activity is selected from among a chemical, a physical and a biological property or activity of the target protein, wherein the change in a predetermined property comprises a change in an activity of the target protein that is at least about 10%, 20%, 30%, 40% or 50% compared to the unmodified target protein.

14. The process of claim 1, wherein the predetermined property or an activity is selected from among a chemical, a physical and a biological property or an activity of the target protein, wherein the change in the predetermined property or an activity comprises a change in a property or an activity of the target protein that is at least about 75%, 100%, 200%, 500% or 1000% compared to the unmodified target protein.

15. The process of claim 1, wherein:

in step (b) the nucleic acid molecules comprise viral vectors, and the methods further comprises assessing the titer of the viral vectors in each set of cells; and the predetermined property or an activity is selected from among a chemical, a physical and a biological property of the target protein.

16. The method of claim 15, wherein titering is effected by real time virus titering, comprising:

(i) incubating the nucleic acid molecules or a vector (biological agent) comprising the nucleic acid molecules at an initial concentration C, which is the unknown titer, with the host cells at a constant known concentration, D;

(ii) measuring at successive times, an output signal, i;

(iii) determining the time tβ, wherein:

tβ corresponds to i=β;

$\beta_{min} < \beta < \beta_{max}$;

$\beta_{min}$ and $\beta_{max}$ correspond to values of i at the inflection point of the curve i=f(t), for the minimal and maximal values, respectively, of the concentrations of a reference biological agent for which the curve tβ=f(c) is predetermined; and (iv) determining the initial concentration C.

17. The method of claim 15, wherein titering is effected by Tagged Replication and Expression Enhancement, comprising:

(i) incubating with host cells a reporter virus vector with a titering virus of unknown titer, wherein the titering virus increases or decreases the output signal from the reporter virus; and (ii) measuring the output signal of the reporter virus and determining the titer of the reporter virus;

(iii) determining the titer of the interfering virus by comparing the titer of the reporter virus in the presence and absence of the interfering virus.

18. The process of claim 1, wherein the performance of the screened proteins is evaluated by a Hill analysis or by fitting the output signal to a curve representative of the interaction of the target protein and a test compound.

19. The process of claim 18, wherein the Hill analysis, comprises:

(a) preparing a sample of each nucleic acid molecule or a plasmid or vector that comprises each nucleic acid molecule (biological agent), wherein each sample is obtained by a serial dilution of the molecules or vector or plasmid at a concentration R1;

(b) incubating each sample of the dilution obtained in (a) with the host cells (target cells) at a constant concentration R2;

(c) determining a P product from the reaction R1+R2, at a t moment, in each the sample; and (d) preparing a theoretical curve H from the experimental points R1 and P, for each biological agent by iterative approximation of parameters of the reaction R1+R2→P, at the t moment, in accordance with the equation:

$$P = P_{max}(\pi R1)^r / (\kappa + (\pi R1)^r) \quad r=1, \ldots, n \quad (2)$$

in which:

R1 represents the biological agent concentration in a sample from the scale;

R2 is concentration of target cells (in vitro or in vivo)

P (output) represents the product from the reaction R1+R2 at a t moment;

$P_{max}$ represents the reaction maximal capacity;

κ represents, at a constant R2 concentration, the biological system for responding to the biological agent (resistance constant R2);

r represents a dependent coefficient of R1 and corresponds to the Hill coefficient; and π represents the intrinsic power of the R1 biological agent to induce a response in the biological system (P production at the t moment); and (e) sorting the κ and π values obtained in (d) for each protein encoded by the nucleic acid molecules or plasmids or vectors and the cells, and then ranking according to the values thereof.

20. A process of claim 1 that is automated.

21. The process of claim 20 that is computer-controlled.

22. A high throughput process for the identification of a protein that differs in a predetermined property from a target protein, comprising:

(a) producing a population of sets of nucleic acid molecules that encode modified forms of a target protein, wherein:

each encoded modified protein in a set differs from the encoded proteins in each other set and from the target protein by one amino acid;

a sufficient number of sets of nucleic acid molecules are produced so that each encoded amino acid residue in the encoded protein is replaced with a pre-selected amino acid along the full-length of the encoded protein so that all positions along the full-length of the protein are individually modified for screening, and each nucleic acid molecule encodes a protein that differs by one amino acid from the target protein; and the members of each set encode the same modified protein;

(b) individually, but at the same time, introducing each set of nucleic acid molecules into host cells and expressing the encoded protein, wherein:

the host cells are organized in an addressable array, whereby the identity of each nucleic acid molecule at each locus in the array is known;

each set of nucleic acid molecules is introduced into host cells at a different locus of the array, whereby the identity of each set of nucleic acid molecules in host cells at each locus of the array is known, wherein:

the cells of each locus of the addressable array contain the same modified nucleic acid molecules;

all encoded proteins in each set contain the same modification; and the proteins in each set differ from the proteins in another set by one amino acid and from the target protein by one amino acid; and (c) individually, but at the same time, screening the sets of encoded proteins to identify one or more proteins, designated hits, that have a predetermined property that differs from the target protein is/are identified, wherein:

each identified protein is designated a hit;

each hit contains a mutation designated a hit position; and the predetermined property is selected from among a chemical, a physical and a biological property of the target protein;

the nucleic acid molecules comprise viral vectors; and the cells are eukaryotic cells that are transduced with the vectors;

(d) modifying the nucleic acid molecules that encode the hits to produce a set of nucleic acid molecules that encode modified hits, wherein each nucleic acid is in a viral vector;

(e) introducing each set of nucleic acids that encode the modified hits into cells; and (f) individually, but at the same time, screening the sets of cells that contain the nucleic acid molecules that encode the modified hits to identify one or more cells that encodes a protein that has a predetermined property or activity that differs from the target protein and has properties that differ from the original hits, wherein each such protein is designated a lead, wherein each and all of steps (a)-(f) are performed in an automated highthroughput format whereby each molecule is individually designed, produced, screened and tested in the high throughput format.

23. The method of claim 22, wherein at step (f) the titer of the viral vectors in each set of cells is determined.

24. The method of claim 23, wherein the target protein is a protein involved in viral replication.

25. The method of claim 22, wherein the pre-selected amino acid is selected from among Ala (A), Ser (S), Pro (P) and Gly (G).

26. The method of claim 22, wherein the pre-selected amino acid is selected from among encoding Arg (R), Asn (N), Asp (D), Cys (C), Gln (O), Glu (E), His (H), Ile (I), Leu (L), Lys (K), Met (M), Phe (F), Thr (T), Trp (W), Tyr (Y) and Val (V).

* * * * *

UNITED STATES PATENT AND TRADEMARK OFFICE
CERTIFICATE OF CORRECTION

PATENT NO. : 7,647,184 B2
APPLICATION NO. : 10/022249
DATED : January 12, 2010
INVENTOR(S) : Vega et al.

It is certified that error appears in the above-identified patent and that said Letters Patent is hereby corrected as shown below:

IN THE CLAIMS:

Please replace Claim 9 with the following amended Claim:

Column 78, lines 23-26
9. The method of claim 1, wherein the pre-selected amino acid is selected from among Arg (R), Asn (N), Asp (D), Cys (C), Gln (Q), Glu (E), His (H), Ile (I), Leu (L), Lys (K), Met (M), Phe (F), Thr (T), Trp (W), Tyr (Y) and Val (V).

Please replace Claim 15 with the following amended Claim:

Column 78, lines 59-65
15. The process of claim 1, wherein:
in step (b) the nucleic acid molecules comprise viral vectors, and the method further comprises assessing the titer of the viral vectors in each set of cells; and
the predetermined property or an activity is selected from among a chemical, a physical and a biological property of the target protein.

Please replace Claim 19 with the following amended Claim:

Column 79, line 33 to Column 80, line 4
19. The process of claim 18, wherein the Hill analysis, comprises:
(a) preparing a sample of each nucleic acid molecule or a plasmid or vector that comprises each nucleic acid molecule (biological agent), wherein each sample is obtained by a serial dilution of the molecules or vector or plasmid at a concentration R1;
(b) incubating each sample of the dilution obtained in (a) with the host cells (target cells) at a constant concentration R2;
(c) determining a P product from the reaction R1 + R2, at a t moment, in each sample; and
(d) preparing a theoretical curve H from the experimental points R1 and P, for each biological agent by iterative approximation of parameters of the reaction R1 + R2 → P, at the t moment, in accordance with the equation:
$$P = P_{max}(\pi R1)r/(\kappa + (\pi R1)r) \quad r=1,....,n \quad (2)$$
in which:
R1 represents the biological agent concentration in a sample from the scale;
R2 is concentration of target cells (in vitro or in vivo)
P (output) represents the product from the reaction R1 + R2 at a t moment;
Pmax represents the reaction maximal capacity;
κ represents, at a constant R2 concentration, the biological system for responding to the biological agent (resistance constant R2);

CERTIFICATE OF CORRECTION (continued)
U.S. Pat. No. 7,647,184 B2 r represents a dependent coefficient of R1 and corresponds to the Hill coefficient; and π represents the intrinsic power of the R1 biological agent to induce a response in the biological system (P production at the t moment); and (e) sorting the κ and π values obtained in (d) for each protein encoded by the nucleic acid molecules or pl

UNITED STATES PATENT AND TRADEMARK OFFICE
CERTIFICATE OF CORRECTION

Page 1 of 2

PATENT NO. : 7,647,184 B2
APPLICATION NO. : 10/022249
DATED : January 12, 2010
INVENTOR(S) : Vega et al.

It is certified that error appears in the above-identified patent and that said Letters Patent is hereby corrected as shown below:

IN THE CLAIMS:

Please replace Claim 9 with the following amended Claim:

Column 78, lines 23-26
   9.     The method of claim 1, wherein the pre-selected amino acid is selected from among Arg (R), Asn (N), Asp (D), Cys (C), Gln (Q), Glu (E), His (H), Ile (I), Leu (L), Lys (K), Met (M), Phe (F), Thr (T), Trp (W), Tyr (Y) and Val (V).

Please replace Claim 15 with the following amended Claim:

Column 78, lines 59-65
   15.     The process of claim 1, wherein:
  in step (b) the nucleic acid molecules comprise viral vectors, and the method further comprises assessing the titer of the viral vectors in each set of cells; and
the predetermined property or an activity is selected from among a chemical, a physical and a biological property of the target protein.

Please replace Claim 19 with the following amended Claim:

Column 79, line 33 to Column 80, line 4
   19.     The process of claim 18, wherein the Hill analysis, comprises:
  (a) preparing a sample of each nucleic acid molecule or a plasmid or vector that comprises each nucleic acid molecule (biological agent), wherein each sample is obtained by a serial dilution of the molecules or vector or plasmid at a concentration R1;

This certificate supersedes the Certificate of Correction issued April 6, 2010.

Signed and Sealed this
Eighteenth Day of January, 2011

David J. Kappos
*Director of the United States Patent and Trademark Office*

(b) incubating each sample of the dilution obtained in (a) with the host cells (target cells) at a constant concentration R2;

(c) determining a P product from the reaction R1 + R2, at a t moment, in each sample; and (d) preparing a theoretical curve H from the experimental points R1 and P, for each biological agent by iterative approximation of parameters of the reaction R1 + R2 → P, at the t moment, in accordance with the equation:

$$P = P_{max}(\pi R1)^r/(\kappa + (\pi R1)^r) \qquad r=1,\ldots,n \quad (2)$$

in which:

R1 represents the biological agent concentration in a sample from the scale;

R2 is concentration of target cells (in vitro or in vivo)

P (output) represents the product from the reaction R1 + R2 at a t moment;

$P_{max}$ represents the reaction maximal capacity;

κ represents, at a constant R2 concentration, the biological system for responding to the biological agent (resistance constant R2);

r represents a dependent coefficient of R1 and corresponds to the Hill coefficient; and π represents the intrinsic power of the R1 biological agent to induce a response in the biological system (P production at the t moment); and (e) sorting the κ and π values obtained in (d) for each protein encoded by the nucleic acid molecules or plasmids or vectors and the cells, and then ranking according to the values thereof.

Please replace Claim 26 with the following amended Claim:
Column 82, lines 4-8

26. The method of claim 22, wherein the pre-selected amino acid is selected from among Arg (R), Asn (N), Asp (D), Cys (C), Gln (Q), Glu (E), His (H), Ile (I), Leu (L), Lys (K), Met (M), Phe (F), Thr (T), Trp (W), Tyr (Y) and Val (V).